US006756215B1

(12) United States Patent
Wolfraim et al.

(10) Patent No.: US 6,756,215 B1
(45) Date of Patent: Jun. 29, 2004

(54) FUNCTIONALIZED TGF-β FUSION PROTEINS

(75) Inventors: Lawrence A. Wolfraim, Silver Spring, MD (US); John J. Letterio, Bethesda, MD (US)

(73) Assignee: The United States of America as represented by the Secretary of the Department of Health & Human Services, Washington, DC (US)

( * ) Notice: Subject to any disclaimer, the term of this patent is extended or adjusted under 35 U.S.C. 154(b) by 0 days.

(21) Appl. No.: 10/017,372

(22) Filed: Oct. 19, 2001

Related U.S. Application Data

(60) Provisional application No. 60/242,292, filed on Oct. 20, 2000.

(51) Int. Cl.[7] .......................... C07K 7/00; C12P 21/00; C12N 5/00
(52) U.S. Cl. .................. 435/69.1; 435/69.7; 435/252.3; 435/254.2; 435/325; 530/300; 530/350
(58) Field of Search .............................. 435/254.2, 325, 435/252.3, 69.1, 69.4, 69.7; 536/23.1; 514/2; 530/300, 350

(56) References Cited

U.S. PATENT DOCUMENTS

| | | | |
|---|---|---|---|
| 4,703,004 A | 10/1987 | Hopp et al. | |
| 4,851,341 A | 7/1989 | Hopp et al. | |
| 4,886,747 A | 12/1989 | Derynck et al. | |
| 5,221,620 A | * 6/1993 | Purchio et al. | 435/69.7 |
| 5,304,541 A | * 4/1994 | Purchio et al. | 514/12 |
| 5,571,714 A | 11/1996 | Dasch et al. | |
| 5,800,811 A | * 9/1998 | Hall et al. | 424/93.7 |
| 5,827,733 A | * 10/1998 | Lee et al. | 435/325 |
| 5,914,254 A | 6/1999 | Mascarenhas et al. | |
| 5,968,780 A | 10/1999 | Fan et al. | |
| 5,981,177 A | 11/1999 | Demirjian et al. | |
| 5,994,104 A | 11/1999 | Anderson et al. | |
| 6,037,145 A | 3/2000 | Yabuta et al. | |
| 2003/0027218 A1 | * 2/2003 | Yamasaki et al. | 435/7.2 |

FOREIGN PATENT DOCUMENTS

| | | | | |
|---|---|---|---|---|
| WO | PCT/US96/08973 | | 12/1996 | |
| WO | PCT/US99/14981 | | 1/2000 | |
| WO | WO 01/81404 | * | 11/2001 | C07K/14/495 |
| WO | WO 01/81404 A2 | * | 11/2001 | C07K/14/495 |

OTHER PUBLICATIONS

Bork, 2000, Genome Research 10:398–400.*
Skolnick et al., 2000, Trends in Biotech. 18(1): 34–39.*
Doerks et al., 1998, Trends in Genetics 14:248–250.*
Brenner, 1999, Trends in Genetics 15:132–133.*
Bork et al., 1996, Trends in Genetics 12:425–427.*
Wells, 1990, Biochemistry 29:8509–8517.*
Ngo et al., 1994, The Protein Folding Problem and Tertiary Structure Prediction, pp. 492–495.*

Jakowlew et al. (1988) "Nucleotide sequence of chicken transforming growth factor–beta 1 (TGFb 1)." Nucleic Acids Research 16(17): 8730.*
Brunner et al. (Aug. 15, 1989) "Site–directed Mutagenesis of Cysteine Residues in the Pro Region of the Transforming Growt Factor b1 Precursor." The Journal of Biological Chemistry 264(23): 13660–13664.*
Bentz, et al., "Improved local delivery of TGF–β2 by binding to injectable fibrillar collagen via difunctional polyethylene glycol", *J. Biomed. Mater. Res.,* 539–548, 1998.
Böttinger, et al., "The recombinant proregion of transforming growth factor β1 (Latency–associated peptide) inhibits active transforming growth factor β1 in transgenic mice," *Proc. Natl. Acad.,* 93:5877–5882, Jun. 1996.
Byrd, et al., "Mechanisms for high–affinity mannose 6–phosphate ligand binding to the insulin–like growth factor II/mannose 6–phosphate receptor: negative cooperativity and receptor oligomerization," *J. Biol. Chem.,* 1:1–2, Apr. 2000.
Chen and Wahl, "Manipulation of TGF–β to control autoimmune and chronic inflammatory disease", *Microbes and Infection,* 1:1367–1380, 1999.
Dubois, et al., Processing of Transforming Growth Factor β1 Precursor by Human Furin Convertase, *JBC Online,* 270 (18):10618–10624, 1995.
Gray and Mason, "Requirement for Activin A and Transforming Growth Factor–β1 Pro–Regions in Homodimer Assembly", *Science,* 247:1328–1330, Mar. 1990.
Han, et al., "Refolding of a Recombinant Collagen–Targeted TGF–β2 Fusion Protein Expressed in *Escherichia coli*", *Prot. Exp. and Purif.,* 11:169–178, 1997.
Huang, et al., "An Active Site of Transforming Growth Factor–β$_1$ for Growth Inhibition and Stimulation", *J. Biol. Chem.,* 274(39):27754–27758, Sep. 1999.
Khalil, "TGF–β: from latent to active", *Microbes and Infection,* 1:1255–1263, 1999.
Kingsley, "The TGF–β superfamily: new members, new receptors, and new genetic tests of function in different organisms", *Genes & Development,* 8:133–146, 1994.
Madisen, et al., "Expression and Characterization of Recombinant TGF–β2 Proteins Produced in Mammalian Cells", *DNA,* 8(3):205–212, 1989.

(List continued on next page.)

Primary Examiner—Elizabeth Kemmerer
Assistant Examiner—Christopher James Nichols
(74) Attorney, Agent, or Firm—Klarquist Sparkman, LLP

(57) ABSTRACT

This disclosure relates to TGF-β family protein fusions that display substantial native TGF-β family protein function while also having an additional functionality conveyed by the addition of a functionalizing peptide domain. Such functionalizing peptide domain can be a tag peptide (e.g., an epitope tag, a purification tag, a molecular size differentiation tag, etc.) or a passenger or targeting protein. Also provided are methods of making these fusions, as well as methods of using them for diagnosis and diagnosis of various conditions, in measuring and monitoring levels of the fusion molecule in experimental systems and subjects, and in measuring and detecting receptor proteins.

24 Claims, 7 Drawing Sheets

OTHER PUBLICATIONS

Matthews, et al., "A sequential dimerization mechanism for erythropoietin receptor activation", *Proc. Natl. Acad. Sci. USA*, 93:9471–9476, Sep. 1996.

Mehta, et al., "Soluble Monomeric P–Selectin Containing Only the Lectin and Epidermal Growth Factor Domains Binds to P–Selectin Glycoprotein Ligand–1 on Leukocytes", *Blood*, 90 (6):2381–2389, Sep. 1997.

Möller, et al., "Subcellular Localization of Epitope–Tagged Neurotrophins in Neuroendocrine Cells", *J. Neuro. Res.*, 51:463–472, 1998.

Oda, et al. al., "A General Method for Rapid Purification of Soluble Versions of Glycosylphosphatidylinosito-l–Anchored Proteins Expressed in Insect Cells: An Application for Human Tissue–Nonspecific Alkaline Phosphatase", *J. Biochem.*, 126:694–699, 1999.

Pfaffinger and De Rubeis, "Shaker K$^+$ Channel T1 Domain Self–tetramerizes to a Stable Structure", *J. Biol. Chem.*, 270 (48):28595–28600, Sep. 1995.

Qian, et al., "Binding Affinity of Transforming Growth Factor–β for Its Type II Receptor Is Determined by the Column–terminal Region of the Molecule", *J. Biol. Chem.*, 271 (48):30656–30662, 1996.

Reichel, et al., "Epitope–tagged insulin–like growth factor–I expression in muscle", *Dom. Anim. Endocrin.*, 18:337–348, 2000.

Reiss, "TGF–β and cancer", *Microbes and Infection*, 1:1327–1347, 1999.

Sporn, "TGF–β: 20 years and counting", *Microbes and Infection*, 1:1251–1253, 1999.

Tio and Moses., "The Drosophila TGFα homolog Spitz acts in photoreceptor recruitment in the developing retina", *Development*, 124:343–351, 1997.

Tuan, et al., "Engineering, Expression and Renaturation of Targeted TGF–Beta Fusion Proteins", *Conn. Tis. Res.*, 34 (1):1–9, 1996.

Vornlocher, et al., "A 110–Kilodalton Subunit of Translation Initiation Factor eIF3 and an Associated 135–kilodalton Protein Are Encoded by the *Saccharomyces cerevisiae* *TIF32* and *TIF31* Genes", *J. Biol. Chem*, 274 (24):16802–16812, 1999.

Wahl, "Introduction", *Microbes and Infection*, 1:1247–1249, 1999.

Wakefield, et al., "Addition of a C–Terminal Extension Sequence to Transforming Growth Factor β1 Interferes with Biosynthetic Processing and Abolishes Biological Activity", *Growth Factors*, 5:243–253, 1991.

* cited by examiner

FIG 6A

N-FLAG-TGFβ1:

```
                                S  S  R  H  R  R ↓ D  Y  K  D  D  D  D
     2601                 AGCTCCCG GCACCGCCGA GACTACAAGG ATGACGACGA
                          TCGAGGGC CGTGGCGGCT CTGATGTTCC TACTGCTGCT
             K  A  L  D  T  N  Y  C  F  S  S  T  E  K  N  C
     2651    CAAGGCCCTG GATACCAACT ACTGCTTCAG CTCCACGGAG AAGAACTGCT
             GTTCCGGGAC CTATGGTTGA TGACGAAGTC GAGGTGCCTC TTCTTGACGA
             C  V  R  Q  L  Y  I  D  F  R  K  D  L  G  W  K  W
     2701    GCGTGCGGCA GCTCTACATT GACTTCCGGA AGGACCTGGG CTGGAAGTGG
             CGCACGCCGT CGAGATGTAA CTGAAGGCCT TCCTGGACCC GACCTTCACC
```

FIG 6B

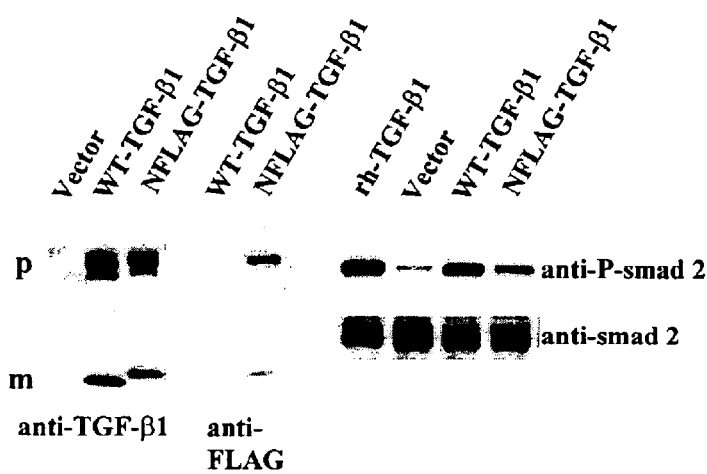

FIG 6C

```
             Q  H  L  H  S  S  R  H  R  R ↓ A  L  D  T  N  D  Y
     2601    CAGCACCTGC ACAGCTCCCG GCACCGCCGA GCCCTGGATA CCAACGACTA
             GTCGTGGACG TGTCGAGGGC CGTGGCGGCT CGGGACCTAT GGTTGCTGAT
        K  D  D  D  K  A  L  D  T  N  Y  C  F  S
     2651 CAAGGATGAC GACGACAAGG CCCTGGATAC CAACTACTGC TTCAGCTCCA
          GTTCCTACTG CTGCTGTTCC GGGACCTATG GTTGATGACG AAGTCGAGGT

Q  H  L  H  S  S  R  H  R  R ↓ A  L  D  T  N  S  Y
     2601    CAGCACCTGC ACAGCTCCCG GCACCGCCGA GCCCTGGATA CCAACAGCTA
             GTCGTGGACG TGTCGAGGGC CGTGGCGGCT CGGGACCTAT GGTTGTCGAT
        P  Y  D  V  P  D  Y  A  S  L  A  L  D  T  N
     2651 CCCATACGAC GTGCCAGACT ACGCATCTCT GGCCCTGGAT ACCAACTACT
          GGGTATGCTG CACGGTCTGA TGCGTAGAGA CCGGGACCTA TGGTTGATGA
```

FIG 6D

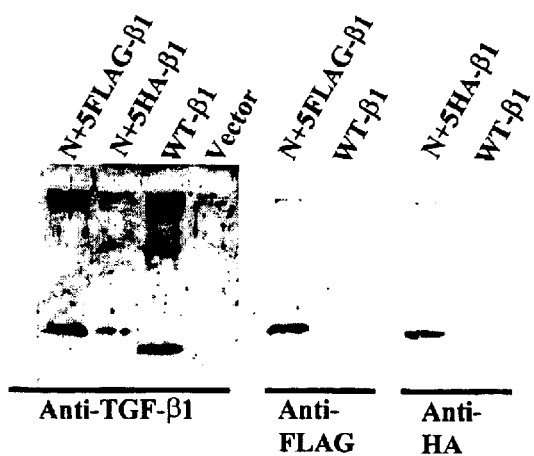

SEQUENCE LISTING

```
<160> NUMBER OF SEQ ID NOS: 39

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
ggagagatct ggtaccgaga tggcgcct                                      28

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2
ataagaattg cggccgcttt aatcgatccc aagtgggctt gg                      42

<210> SEQ ID NO 3
<211> LENGTH: 48
<212> TYPE: DNA
<213> ORGANISM: Artificial Sequence
<220> FEATURE:
<223> OTHER INFORMATION: Primer

<400> SEQUENCE: 3
gactacaagg atgacgacga caaggccctg gataccaact actgcttc                48

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
cttgtcgtcg tcatccttgt agtctcggcg gtgccgggag ctgtg                   45

<210> SEQ ID NO 5
<211> LENGTH: 45
<212> TYPE: DNA
<213> ORGANISM: Artificial Sequence
<220> FEATURE:
<223> OTHER INFORMATION: Primer

<400> SEQUENCE: 5
gactacaagg atgacgacga caggagaaga actgctgcgt gcggc                   45

<210> SEQ ID NO 6
<211> LENGTH: 45
<212> TYPE: DNA
<213> ORGANISM: Artificial Sequence
<220> FEATURE:
```

```
<223> OTHER INFORMATION: Primer

<400> SEQUENCE: 6
cttgtcgtcg tcatccttgt agtctcggcg gtgccgggag ctgtg                    45

<210> SEQ ID NO 7
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 7

Asp Tyr Lys Asp Asp Asp Asp Lys
1               5

<210> SEQ ID NO 8
<211> LENGTH: 1197
<212> TYPE: DNA
<213> ORGANISM: Artificial Sequence
<220> FEATURE:
<223> OTHER INFORMATION: Porcine (Sus scrofa) TGF-beta1/N-terminal FLAG
      Fusion Construct
<220> FEATURE:
<221> NAME/KEY: CDS
<222> LOCATION: (1)..(1197)
<223> OTHER INFORMATION: Protein coding sequence
<220> FEATURE:
<221> NAME/KEY: misc_feature
<222> LOCATION: (278)..(279)
<223> OTHER INFORMATION: Maturation cleavage site (relates to amino acid
      residue nos.)

<400> SEQUENCE: 8 atg gcg cct tcg ggg ctg cgg ctc ttg ccg ctg ctg ccg ctg ctg           48
Met Ala Pro Ser Gly Leu Arg Leu Leu Pro Leu Leu Pro Leu Leu
1               5                   10                  15 tgg ctg cta gtg ctg acg cct ggc cgg ccg gcc gcc gga ctg tcc acc       96
Trp Leu Leu Val Leu Thr Pro Gly Arg Pro Ala Ala Gly Leu Ser Thr
            20                  25                  30 tgc aag acc atc gac atg gag ctg gtg aag cgg aag cgc atc gag gcc      144
Cys Lys Thr Ile Asp Met Glu Leu Val Lys Arg Lys Arg Ile Glu Ala
        35                  40                  45 att cgc ggc cag att ctg tcc aag ctt cgg ctt gcc agc ccc ccg agc      192
Ile Arg Gly Gln Ile Leu Ser Lys Leu Arg Leu Ala Ser Pro Pro Ser
    50                  55                  60 cag ggg gac gtg ccg ccc ggc ccg ctg cct gag gca gta ctg gct ctt      240
Gln Gly Asp Val Pro Pro Gly Pro Leu Pro Glu Ala Val Leu Ala Leu
65                  70                  75                  80 tac aac agt acc cgc gac cgg gta gcc ggg gaa agt gtc gaa ccg gag      288
Tyr Asn Ser Thr Arg Asp Arg Val Ala Gly Glu Ser Val Glu Pro Glu
                85                  90                  95 ccc gag cca gag gcg gac tac tac gcc aag gag gtc acc cgc gtg cta      336
Pro Glu Pro Glu Ala Asp Tyr Tyr Ala Lys Glu Val Thr Arg Val Leu
            100                 105                 110 atg gtg gaa agc ggc aac caa atc tat gat aaa ttc aag ggc acc ccc      384
Met Val Glu Ser Gly Asn Gln Ile Tyr Asp Lys Phe Lys Gly Thr Pro
        115                 120                 125 cac agc tta tat atg ctg ttc aac acg tcg gag ctc cgg gaa gcg gtg      432
His Ser Leu Tyr Met Leu Phe Asn Thr Ser Glu Leu Arg Glu Ala Val
    130                 135                 140 ccg gaa cct gta ttg ctc tct cgg gca gag ctg cgc ctg ctg agg ctc      480
Pro Glu Pro Val Leu Leu Ser Arg Ala Glu Leu Arg Leu Leu Arg Leu
145                 150                 155                 160
```

```
aag tta aaa gtg gag cag cac gtg gag cta tac cag aaa tac agc aat         528
Lys Leu Lys Val Glu Gln His Val Glu Leu Tyr Gln Lys Tyr Ser Asn
            165                 170                 175 gat tcc tgg cgc tac ctc agc aac cgg ctg ctg gcc ccc agt gac tca         576
Asp Ser Trp Arg Tyr Leu Ser Asn Arg Leu Leu Ala Pro Ser Asp Ser
        180                 185                 190 ccg gag tgg ctg tcc ttt gat gtc acc gga gtt gtg cgg cag tgg ctg         624
Pro Glu Trp Leu Ser Phe Asp Val Thr Gly Val Val Arg Gln Trp Leu
    195                 200                 205 acc cgc aga gag gct ata gag ggt ttt cgc ctc agt gcc cac tct tcc         672
Thr Arg Arg Glu Ala Ile Glu Gly Phe Arg Leu Ser Ala His Ser Ser
210                 215                 220 tct gac agc aaa gat aac aca ctc cac gtg gaa att aac ggg ttc aat         720
Ser Asp Ser Lys Asp Asn Thr Leu His Val Glu Ile Asn Gly Phe Asn
225                 230                 235                 240 tct ggc cgc cgg ggt gac ctg gcc acc att cac ggc atg aac cgg ccc         768
Ser Gly Arg Arg Gly Asp Leu Ala Thr Ile His Gly Met Asn Arg Pro
                245                 250                 255 ttc ctg ctc ctc atg gcc acc ccg ctg gag agg gcc cag cac ctg cac         816
Phe Leu Leu Leu Met Ala Thr Pro Leu Glu Arg Ala Gln His Leu His
            260                 265                 270 agc tcc cgg cac cgc cga gac tac aag gat gac gac gac aag gcc ctg         864
Ser Ser Arg His Arg Arg Asp Tyr Lys Asp Asp Asp Asp Lys Ala Leu
        275                 280                 285 gat acc aac tac tgc ttc agc tcc acg gag aag aac tgc tgc gtg cgg         912
Asp Thr Asn Tyr Cys Phe Ser Ser Thr Glu Lys Asn Cys Cys Val Arg
    290                 295                 300 cag ctc tac att gac ttc cgg aag gac ctg ggc tgg aag tgg att cat         960
Gln Leu Tyr Ile Asp Phe Arg Lys Asp Leu Gly Trp Lys Trp Ile His
305                 310                 315                 320 gaa ccc aag ggc tac cat gcc aat ttc tgc ctg ggg ccc tgt ccc tac        1008
Glu Pro Lys Gly Tyr His Ala Asn Phe Cys Leu Gly Pro Cys Pro Tyr
                325                 330                 335 atc tgg agc cta gac act cag tac agc aag gtc ctg gct ctg tac aac        1056
Ile Trp Ser Leu Asp Thr Gln Tyr Ser Lys Val Leu Ala Leu Tyr Asn
            340                 345                 350 cag cac aac ccg ggc gcg tcg gcg gcg ccg tgc tgc gtg ccg cag gcg        1104
Gln His Asn Pro Gly Ala Ser Ala Ala Pro Cys Cys Val Pro Gln Ala
        355                 360                 365 ctg gag cca ctg ccc atc gtg tac tac gtg ggc cgc aag ccc aag gtg        1152
Leu Glu Pro Leu Pro Ile Val Tyr Tyr Val Gly Arg Lys Pro Lys Val
    370                 375                 380 gag cag ctg tcc aac atg atc gtg cgt tcc tgc aag tgc agc tga            1197
Glu Gln Leu Ser Asn Met Ile Val Arg Ser Cys Lys Cys Ser
385                 390                 395

<210> SEQ ID NO 9
<211> LENGTH: 398
<212> TYPE: PRT
<213> ORGANISM: Artificial Sequence
<220> FEATURE:
<223> OTHER INFORMATION: Porcine (Sus scrofa) TGF-beta1/N-terminal FLAG
      Fusion Construct

<400> SEQUENCE: 9

Met Ala Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45
```

```
Ile Arg Gly Gln Ile Leu Ser Lys Leu Arg Leu Ala Ser Pro Pro Ser
 50                  55                  60

Gln Gly Asp Val Pro Gly Pro Leu Pro Glu Ala Val Leu Ala Leu
 65                  70                  75                  80

Tyr Asn Ser Thr Arg Asp Arg Val Ala Gly Glu Ser Val Glu Pro Glu
                 85                  90                  95

Pro Glu Pro Glu Ala Asp Tyr Tyr Ala Lys Glu Val Thr Arg Val Leu
                100                 105                 110

Met Val Glu Ser Gly Asn Gln Ile Tyr Asp Lys Phe Lys Gly Thr Pro
                115                 120                 125

His Ser Leu Tyr Met Leu Phe Asn Thr Ser Glu Leu Arg Glu Ala Val
                130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Ser
                180                 185                 190

Pro Glu Trp Leu Ser Phe Asp Val Thr Gly Val Val Arg Gln Trp Leu
                195                 200                 205

Thr Arg Arg Glu Ala Ile Glu Gly Phe Arg Leu Ser Ala His Ser Ser
210                 215                 220

Ser Asp Ser Lys Asp Asn Thr Leu His Val Glu Ile Asn Gly Phe Asn
225                 230                 235                 240

Ser Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu His
                260                 265                 270

Ser Ser Arg His Arg Arg Asp Tyr Lys Asp Asp Asp Lys Ala Leu
                275                 280                 285

Asp Thr Asn Tyr Cys Phe Ser Ser Thr Glu Lys Asn Cys Cys Val Arg
290                 295                 300

Gln Leu Tyr Ile Asp Phe Arg Lys Asp Leu Gly Trp Lys Trp Ile His
305                 310                 315                 320

Glu Pro Lys Gly Tyr His Ala Asn Phe Cys Leu Gly Pro Cys Pro Tyr
                325                 330                 335

Ile Trp Ser Leu Asp Thr Gln Tyr Ser Lys Val Leu Ala Leu Tyr Asn
                340                 345                 350

Gln His Asn Pro Gly Ala Ser Ala Pro Cys Cys Val Pro Gln Ala
                355                 360                 365

Leu Glu Pro Leu Pro Ile Val Tyr Tyr Val Gly Arg Lys Pro Lys Val
                370                 375                 380

Glu Gln Leu Ser Asn Met Ile Val Arg Ser Cys Lys Cys Ser
385                 390                 395
```

<210> SEQ ID NO 10
<211> LENGTH: 363
<212> TYPE: DNA
<213> ORGANISM: Artificial Sequence
<220> FEATURE:
<223> OTHER INFORMATION: Porcine (Sus scrofa) TGF-beta1/N-terminal FLAG
      Fusion Construct

<400> SEQUENCE: 10
gactacaagg atgacgacga caaggccctg gataccaact actgcttcag ctccacggag    60

```
aagaactgct gcgtgcggca gctctacatt gacttccgga aggacctggg ctggaagtgg      120
attcatgaac ccaagggcta ccatgccaat ttctgcctgg ggccctgtcc ctacatctgg      180
agcctagaca ctcagtacag caaggtcctg gctctgtaca accagcacaa cccgggcgcg      240
tcggcggcgc cgtgctgcgt gccgcaggcg ctggagccac tgcccatcgt gtactacgtg      300
ggccgcaagc ccaaggtgga gcagctgtcc aacatgatcg tgcgttcctg caagtgcagc      360
tga                                                                   363
```

```
<210> SEQ ID NO 11
<211> LENGTH: 120
<212> TYPE: PRT
<213> ORGANISM: Artificial Sequence
<220> FEATURE:
<223> OTHER INFORMATION: Porcine (Sus scrofa) TGF-beta1/N-terminal FLAG
      Fusion Construct
<220> FEATURE:
<221> NAME/KEY: PEPTIDE
<222> LOCATION: (1)..(8)
<223> OTHER INFORMATION: FLAG tag

<400> SEQUENCE: 11
```

```
Asp Tyr Lys Asp Asp Asp Asp Lys Ala Leu Asp Thr Asn Tyr Cys Phe
 1               5                  10                  15

Ser Ser Thr Glu Lys Asn Cys Cys Val Arg Gln Leu Tyr Ile Asp Phe
            20                  25                  30

Arg Lys Asp Leu Gly Trp Lys Trp Ile His Glu Pro Lys Gly Tyr His
        35                  40                  45

Ala Asn Phe Cys Leu Gly Pro Cys Pro Tyr Ile Trp Ser Leu Asp Thr
    50                  55                  60

Gln Tyr Ser Lys Val Leu Ala Leu Tyr Asn Gln His Asn Pro Gly Ala
 65                 70                  75                  80

Ser Ala Ala Pro Cys Cys Val Pro Gln Ala Leu Glu Pro Leu Pro Ile
                85                  90                  95

Val Tyr Tyr Val Gly Arg Lys Pro Lys Val Glu Gln Leu Ser Asn Met
            100                 105                 110

Ile Val Arg Ser Cys Lys Cys Ser
        115                 120
```

```
<210> SEQ ID NO 12
<211> LENGTH: 1197
<212> TYPE: DNA
<213> ORGANISM: Artificial Sequence
<220> FEATURE:
<223> OTHER INFORMATION: Porcine (Sus scrofa) TGF-beta1/FLAG (11/12)
      Fusion Construct
<220> FEATURE:
<221> NAME/KEY: CDS
<222> LOCATION: (1)..(1197)
<223> OTHER INFORMATION: Protein coding sequence
<220> FEATURE:
<221> NAME/KEY: misc_feature
<222> LOCATION: (278)..(279)
<223> OTHER INFORMATION: Maturation cleavage site (relates to amino acid
      residue nos.)

<400> SEQUENCE: 12
```

```
atg gcg cct tcg ggg ctg cgg ctc ttg ccg ctg ctg ccg ctg ctg         48
Met Ala Pro Ser Gly Leu Arg Leu Leu Pro Leu Leu Pro Leu Leu
 1               5                  10                  15 tgg ctg cta gtg ctg acg cct ggc cgg ccg gcc gcc gga ctg tcc acc     96
Trp Leu Leu Val Leu Thr Pro Gly Arg Pro Ala Ala Gly Leu Ser Thr
            20                  25                  30
```

```
tgc aag acc atc gac atg gag ctg gtg aag cgg aag cgc atc gag gcc     144
Cys Lys Thr Ile Asp Met Glu Leu Val Lys Arg Lys Arg Ile Glu Ala
         35                  40                  45 att cgc ggc cag att ctg tcc aag ctt cgg ctt gcc agc ccc ccg agc     192
Ile Arg Gly Gln Ile Leu Ser Lys Leu Arg Leu Ala Ser Pro Pro Ser
 50                  55                  60 cag ggg gac gtg ccg ccc ggc ccg ctg cct gag gca gta ctg gct ctt     240
Gln Gly Asp Val Pro Pro Gly Pro Leu Pro Glu Ala Val Leu Ala Leu
 65                  70                  75                  80 tac aac agt acc cgc gac cgg gta gcc ggg gaa agt gtc gaa ccg gag     288
Tyr Asn Ser Thr Arg Asp Arg Val Ala Gly Glu Ser Val Glu Pro Glu
                 85                  90                  95 ccc gag cca gag gcg gac tac tac gcc aag gag gtc acc cgc gtg cta     336
Pro Glu Pro Glu Ala Asp Tyr Tyr Ala Lys Glu Val Thr Arg Val Leu
            100                 105                 110 atg gtg gaa agc ggc aac caa atc tat gat aaa ttc aag ggc acc ccc     384
Met Val Glu Ser Gly Asn Gln Ile Tyr Asp Lys Phe Lys Gly Thr Pro
        115                 120                 125 cac agc tta tat atg ctg ttc aac acg tcg gag ctc cgg gaa gcg gtg     432
His Ser Leu Tyr Met Leu Phe Asn Thr Ser Glu Leu Arg Glu Ala Val
    130                 135                 140 ccg gaa cct gta ttg ctc tct cgg gca gag ctg cgc ctg ctg agg ctc     480
Pro Glu Pro Val Leu Leu Ser Arg Ala Glu Leu Arg Leu Leu Arg Leu
145                 150                 155                 160 aag tta aaa gtg gag cag cac gtg gag cta tac cag aaa tac agc aat     528
Lys Leu Lys Val Glu Gln His Val Glu Leu Tyr Gln Lys Tyr Ser Asn
                165                 170                 175 gat tcc tgg cgc tac ctc agc aac cgg ctg ctg gcc ccc agt gac tca     576
Asp Ser Trp Arg Tyr Leu Ser Asn Arg Leu Leu Ala Pro Ser Asp Ser
            180                 185                 190 ccg gag tgg ctg tcc ttt gat gtc acc gga gtt gtg cgg cag tgg ctg     624
Pro Glu Trp Leu Ser Phe Asp Val Thr Gly Val Val Arg Gln Trp Leu
        195                 200                 205 acc cgc aga gag gct ata gag ggt ttt cgc ctc agt gcc cac tct tcc     672
Thr Arg Arg Glu Ala Ile Glu Gly Phe Arg Leu Ser Ala His Ser Ser
    210                 215                 220 tct gac agc aaa gat aac aca ctc cac gtg gaa att aac ggg ttc aat     720
Ser Asp Ser Lys Asp Asn Thr Leu His Val Glu Ile Asn Gly Phe Asn
225                 230                 235                 240 tct ggc cgc cgg ggt gac ctg gcc acc att cac ggg atg aac cgg ccc     768
Ser Gly Arg Arg Gly Asp Leu Ala Thr Ile His Gly Met Asn Arg Pro
                245                 250                 255 ttc ctg ctc ctc atg gcc acc ccg ctg gag agg gcc cag cac ctg cac     816
Phe Leu Leu Leu Met Ala Thr Pro Leu Glu Arg Ala Gln His Leu His
            260                 265                 270 agc tcc cgg cac cgc cga gcc ctg gat acc aac tac tgc ttc agc tcc     864
Ser Ser Arg His Arg Arg Ala Leu Asp Thr Asn Tyr Cys Phe Ser Ser
        275                 280                 285 acg gac tac aag gat gac gac gac aag gag aag aac tgc tgc gtg cgg     912
Thr Asp Tyr Lys Asp Asp Asp Asp Lys Glu Lys Asn Cys Cys Val Arg
    290                 295                 300 cag ctc tac att gac ttc cgg aag gac ctg ggc tgg aag tgg att cat     960
Gln Leu Tyr Ile Asp Phe Arg Lys Asp Leu Gly Trp Lys Trp Ile His
305                 310                 315                 320 gaa ccc aag ggc tac cat gcc aat ttc tgc ctg ggg ccc tgt ccc tac    1008
Glu Pro Lys Gly Tyr His Ala Asn Phe Cys Leu Gly Pro Cys Pro Tyr
                325                 330                 335 atc tgg agc cta gac act cag tac agc aag gtc ctg gct ctg tac aac    1056
Ile Trp Ser Leu Asp Thr Gln Tyr Ser Lys Val Leu Ala Leu Tyr Asn
```

```
                         340               345                350
cag cac aac ccg ggc gcg tcg gcg gcg ccg tgc tgc gtg ccg cag gcg         1104
Gln His Asn Pro Gly Ala Ser Ala Ala Pro Cys Cys Val Pro Gln Ala
            355                360                365 ctg gag cca ctg ccc atc gtg tac tac gtg ggc cgc aag ccc aag gtg         1152
Leu Glu Pro Leu Pro Ile Val Tyr Tyr Val Gly Arg Lys Pro Lys Val
370                375                380 gag cag ctg tcc aac atg atc gtg cgt tcc tgc aag tgc agc tga             1197
Glu Gln Leu Ser Asn Met Ile Val Arg Ser Cys Lys Cys Ser
385                390                395

<210> SEQ ID NO 13
<211> LENGTH: 398
<212> TYPE: PRT
<213> ORGANISM: Artificial Sequence
<220> FEATURE:
<223> OTHER INFORMATION: Porcine (Sus scrofa) TGF-beta1/FLAG (11/12)
      Fusion Construct

<400> SEQUENCE: 13

Met Ala Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
50                  55                  60

Gln Gly Asp Val Pro Pro Gly Pro Leu Pro Glu Ala Val Leu Ala Leu
65                  70                  75                  80

Tyr Asn Ser Thr Arg Asp Arg Val Ala Gly Glu Ser Val Glu Pro Glu
                85                  90                  95

Pro Glu Pro Glu Ala Asp Tyr Tyr Ala Lys Glu Val Thr Arg Val Leu
            100                 105                 110

Met Val Glu Ser Gly Asn Gln Ile Tyr Asp Lys Phe Lys Gly Thr Pro
        115                 120                 125

His Ser Leu Tyr Met Leu Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Thr Arg Arg Glu Ala Ile Glu Gly Phe Arg Leu Ser Ala His Ser Ser
        210                 215                 220

Ser Asp Ser Lys Asp Asn Thr Leu His Val Glu Ile Asn Gly Phe Asn
225                 230                 235                 240

Ser Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285
```

```
Thr Asp Tyr Lys Asp Asp Asp Lys Glu Lys Asn Cys Cys Val Arg
    290                 295                 300

Gln Leu Tyr Ile Asp Phe Arg Lys Asp Leu Gly Trp Lys Trp Ile His
305                 310                 315                 320

Glu Pro Lys Gly Tyr His Ala Asn Phe Cys Leu Gly Pro Cys Pro Tyr
                325                 330                 335

Ile Trp Ser Leu Asp Thr Gln Tyr Ser Lys Val Leu Ala Leu Tyr Asn
            340                 345                 350

Gln His Asn Pro Gly Ala Ser Ala Ala Pro Cys Cys Val Pro Gln Ala
        355                 360                 365

Leu Glu Pro Leu Pro Ile Val Tyr Val Gly Arg Lys Pro Lys Val
    370                 375                 380

Glu Gln Leu Ser Asn Met Ile Val Arg Ser Cys Lys Cys Ser
385                 390                 395
```

<210> SEQ ID NO 14
<211> LENGTH: 363
<212> TYPE: DNA
<213> ORGANISM: Artificial Sequence
<220> FEATURE:
<223> OTHER INFORMATION: Porcine (Sus scrofa) TGF-beta1/FLAG (11/12)
      Fusion Construct

<400> SEQUENCE: 14

```
gccctggata ccaactactg cttcagctcc acggactaca aggatgacga cgacaaggag    60
aagaactgct gcgtgcggca gctctacatt gacttccgga aggacctggg ctggaagtgg   120
attcatgaac ccaagggcta ccatgccaat ttctgcctgg ggccctgtcc ctacatctgg   180
agcctagaca ctcagtacaa caaggtcctg gctctgtaca accagcacaa cccgggcgcg   240
tcggcggcgc cgtgctgcgt gccgcaggcg ctggagccac tgcccatcgt gtactacgtg   300
ggccgcaagc ccaaggtgga gcagctgtcc aacatgatcg tgcgttcctg caagtgcagc   360
tga                                                                 363
```

<210> SEQ ID NO 15
<211> LENGTH: 120
<212> TYPE: PRT
<213> ORGANISM: Artificial Sequence
<220> FEATURE:
<223> OTHER INFORMATION: Porcine (Sus scrofa) TGF-beta1/FLAG (11/12)
      Fusion Construct
<220> FEATURE:
<221> NAME/KEY: peptide
<222> LOCATION: (12)..(19)
<223> OTHER INFORMATION: FLAG tag

<400> SEQUENCE: 15

```
Ala Leu Asp Thr Asn Tyr Cys Phe Ser Ser Thr Asp Tyr Lys Asp
1               5                   10                  15

Asp Asp Lys Glu Lys Asn Cys Cys Val Arg Gln Leu Tyr Ile Asp Phe
            20                  25                  30

Arg Lys Asp Leu Gly Trp Lys Trp Ile His Glu Pro Lys Gly Tyr His
        35                  40                  45

Ala Asn Phe Cys Leu Gly Pro Cys Pro Tyr Ile Trp Ser Leu Asp Thr
    50                  55                  60

Gln Tyr Ser Lys Val Leu Ala Leu Tyr Asn Gln His Asn Pro Gly Ala
65                  70                  75                  80

Ser Ala Ala Pro Cys Cys Val Pro Gln Ala Leu Glu Pro Leu Pro Ile
                85                  90                  95
```

-continued

```
Val Tyr Tyr Val Gly Arg Lys Pro Lys Val Glu Gln Leu Ser Asn Met
            100                 105                 110
Ile Val Arg Ser Cys Lys Cys Ser
        115                 120

<210> SEQ ID NO 16
<211> LENGTH: 1612
<212> TYPE: DNA
<213> ORGANISM: Artificial Sequence
<220> FEATURE:
<223> OTHER INFORMATION: Murine (Mus musculus) TGF-beta1/N+5 FLAG
      Fusion Construct
<220> FEATURE:
<221> NAME/KEY: 5'UTR
<222> LOCATION: (1)..(347)
<223> OTHER INFORMATION: 5' untranslated region
<220> FEATURE:
<221> NAME/KEY: CDS
<222> LOCATION: (348)..(1559)
<223> OTHER INFORMATION: Protein coding sequence
<220> FEATURE:
<221> NAME/KEY: misc_feature
<222> LOCATION: (1182)..(1196)
<223> OTHER INFORMATION: Encodes amino acid residues 1-5 of TGF-beta1
<220> FEATURE:
<221> NAME/KEY: misc_feature
<222> LOCATION: (1182)..(1159)
<223> OTHER INFORMATION: Encodes mature fusion protein
<220> FEATURE:
<221> NAME/KEY: misc_feature
<222> LOCATION: (1197)..(1220)
<223> OTHER INFORMATION: Encodes FLAG epitope tag
<220> FEATURE:
<221> NAME/KEY: 3'UTR
<222> LOCATION: (1560)..(1612)
<223> OTHER INFORMATION: 3' untranslated region

<400> SEQUENCE: 16
ccccagcctg cctcttgagt ccctcgcatc ccaggaccct ctctccccg agaggcagat      60 ctccctcgga cctgctggca gtagctcccc tatttaagaa cacccacttt tggatctcag    120
agagcgctca tctcgatttt taccctggtg gtatactgag acaccttggt gtcagagcct    180
caccgcgact cctgctgctt tctccctcaa cctcaaatta ttcaggacta tcacctacct    240
ttccttggga gaccccaccc cacaagccct gcaggggcgg ggcctccgca tcccactttt    300
gccgagggtt cccgctctcc gaagtgccgt ggggcgccgc ctccccc atg ccg ccc      356
                                                 Met Pro Pro
                                                  1 tcg ggg ctg cgg cta ctg ccg ctt ctg ctc cca ctc ccg tgg ctt cta      404
Ser Gly Leu Arg Leu Leu Pro Leu Leu Leu Pro Leu Pro Trp Leu Leu
    5                  10                  15 gtg ctg acg ccc ggg agg cca gcc gcg gga ctc tcc acc tgc aag acc      452
Val Leu Thr Pro Gly Arg Pro Ala Ala Gly Leu Ser Thr Cys Lys Thr
20                  25                  30                  35 atc gac atg gag ctg gtg aaa cgg aag cgc atc gaa gcc atc cgt ggc      500
Ile Asp Met Glu Leu Val Lys Arg Lys Arg Ile Glu Ala Ile Arg Gly
                40                  45                  50 cag atc ctg tcc aaa cta agg ctc gcc agt ccc cca agc cag ggg gag      548
Gln Ile Leu Ser Lys Leu Arg Leu Ala Ser Pro Pro Ser Gln Gly Glu
            55                  60                  65 gta ccg ccc ggc ccg ctg ccc gag gcg gtg ctc gct ttg tac aac agc      596
Val Pro Pro Gly Pro Leu Pro Glu Ala Val Leu Ala Leu Tyr Asn Ser
        70                  75                  80 acc cgc gac cgg gtg gca ggc gag agc gcc gac cca gag ccg gag ccc      644
Thr Arg Asp Arg Val Ala Gly Glu Ser Ala Asp Pro Glu Pro Glu Pro
    85                  90                  95
```

-continued

```
gaa gcg gac tac tat gct aaa gag gtc acc cgc gtg cta atg gtg gac      692
Glu Ala Asp Tyr Tyr Ala Lys Glu Val Thr Arg Val Leu Met Val Asp
100             105                 110                 115 cgc aac aac gcc atc tat gag aaa acc aaa gac atc tca cac agt ata      740
Arg Asn Asn Ala Ile Tyr Glu Lys Thr Lys Asp Ile Ser His Ser Ile
            120                 125                 130 tat atg ttc ttc aat acg tca gac att cgg gaa gca gtg ccc gaa ccc      788
Tyr Met Phe Phe Asn Thr Ser Asp Ile Arg Glu Ala Val Pro Glu Pro
        135                 140                 145 cca ttg ctg tcc cgt gca gag ctg cgc ttg cag aga tta aaa tca agt      836
Pro Leu Leu Ser Arg Ala Glu Leu Arg Leu Gln Arg Leu Lys Ser Ser
    150                 155                 160 gtg gag caa cat gtg gaa ctc tac cag aaa tat agc aac aat tcc tgg      884
Val Glu Gln His Val Glu Leu Tyr Gln Lys Tyr Ser Asn Asn Ser Trp
165                 170                 175 cgt tac ctt ggt aac cgg ctg ctg acc ccc act gat acg cct gag tgg      932
Arg Tyr Leu Gly Asn Arg Leu Leu Thr Pro Thr Asp Thr Pro Glu Trp
180                 185                 190                 195 ctg tct ttt gac gtc act gga gtt gta cgg cag tgg ctg aac caa gga      980
Leu Ser Phe Asp Val Thr Gly Val Val Arg Gln Trp Leu Asn Gln Gly
            200                 205                 210 gac gga ata cag ggc ttt cga ttc agc gct cac tgc tct tgt gac agc     1028
Asp Gly Ile Gln Gly Phe Arg Phe Ser Ala His Cys Ser Cys Asp Ser
        215                 220                 225 aaa gat aac aaa ctc cac gtg gaa atc aac ggg atc agc ccc aaa cgt     1076
Lys Asp Asn Lys Leu His Val Glu Ile Asn Gly Ile Ser Pro Lys Arg
    230                 235                 240 cgg ggc gac ctg ggc acc atc cat gac atg aac cgg ccc ttc ctg ctc     1124
Arg Gly Asp Leu Gly Thr Ile His Asp Met Asn Arg Pro Phe Leu Leu
245                 250                 255 ctc atg gcc acc ccc ctg gaa agg gcc cag cac ctg cac agc tca cgg     1172
Leu Met Ala Thr Pro Leu Glu Arg Ala Gln His Leu His Ser Ser Arg
260                 265                 270                 275 cac cgg aga gcc ctg gat acc aac gac tac aag gat gac gac gac aag     1220
His Arg Arg Ala Leu Asp Thr Asn Asp Tyr Lys Asp Asp Asp Asp Lys
            280                 285                 290 gcc ctg gat acc aac tat tgc ttc agc tcc aca gag aag aac tgc tgt     1268
Ala Leu Asp Thr Asn Tyr Cys Phe Ser Ser Thr Glu Lys Asn Cys Cys
        295                 300                 305 gtg cgg cag ctg tac att gac ttt agg aag gac ctg ggt tgg aag tgg     1316
Val Arg Gln Leu Tyr Ile Asp Phe Arg Lys Asp Leu Gly Trp Lys Trp
    310                 315                 320 atc cac gag ccc aag ggc tac cat gcc aac ttc tgt ctg gga ccc tgc     1364
Ile His Glu Pro Lys Gly Tyr His Ala Asn Phe Cys Leu Gly Pro Cys
325                 330                 335 ccc tat att tgg agc ctg gac aca cag tac agc aag gtc ctt gcc ctc     1412
Pro Tyr Ile Trp Ser Leu Asp Thr Gln Tyr Ser Lys Val Leu Ala Leu
340                 345                 350                 355 tac aac caa cac aac ccg ggc gct tcg gcg tca ccg tgc tgc gtg ccg     1460
Tyr Asn Gln His Asn Pro Gly Ala Ser Ala Ser Pro Cys Cys Val Pro
            360                 365                 370 cag gct ttg gag cca ctg ccc atc gtc tac tac gtg ggt cgc aag ccc     1508
Gln Ala Leu Glu Pro Leu Pro Ile Val Tyr Tyr Val Gly Arg Lys Pro
        375                 380                 385 aag gtg gag cag ttg tcc aac atg att gtg cgc tcc tgc aag tgc agc     1556
Lys Val Glu Gln Leu Ser Asn Met Ile Val Arg Ser Cys Lys Cys Ser
390                 395                 400 tga agccccgccc cgccccgccc ctcccggcag gcccggcccc gccccgccc cgc       1612
```

<210> SEQ ID NO 17
<211> LENGTH: 403
<212> TYPE: PRT
<213> ORGANISM: Artificial Sequence
<220> FEATURE:
<223> OTHER INFORMATION: Murine (Mus musculus) TGF-beta1/N+5 FLAG Fusion Construct

<400> SEQUENCE: 17

```
Met Pro Pro Ser Gly Leu Arg Leu Leu Pro Leu Leu Pro Leu Pro
1               5                   10                  15

Trp Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
                85                  90                  95

Pro Glu Pro Glu Ala Asp Tyr Tyr Ala Lys Glu Val Thr Arg Val Leu
                100                 105                 110

Met Val Asp Arg Asn Asn Ala Ile Tyr Glu Lys Thr Lys Asp Ile Ser
            115                 120                 125

His Ser Ile Tyr Met Phe Phe Asn Thr Ser Asp Ile Arg Glu Ala Val
    130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Asp Tyr Lys Asp Asp
        275                 280                 285

Asp Asp Lys Ala Leu Asp Thr Asn Tyr Cys Phe Ser Ser Thr Glu Lys
290                 295                 300

Asn Cys Cys Val Arg Gln Leu Tyr Ile Asp Phe Arg Lys Asp Leu Gly
305                 310                 315                 320

Trp Lys Trp Ile His Glu Pro Lys Gly Tyr His Ala Asn Phe Cys Leu
                325                 330                 335

Gly Pro Cys Pro Tyr Ile Trp Ser Leu Asp Thr Gln Tyr Ser Lys Val
            340                 345                 350

Leu Ala Leu Tyr Asn Gln His Asn Pro Gly Ala Ser Ala Ser Pro Cys
        355                 360                 365
```

```
Cys Val Pro Gln Ala Leu Glu Pro Leu Pro Ile Val Tyr Tyr Val Gly
        370                 375                 380

Arg Lys Pro Lys Val Glu Gln Leu Ser Asn Met Ile Val Arg Ser Cys
385                 390                 395                 400

Lys Cys Ser

<210> SEQ ID NO 18
<211> LENGTH: 73
<212> TYPE: DNA
<213> ORGANISM: Artificial Sequence
<220> FEATURE:
<223> OTHER INFORMATION: Primer

<400> SEQUENCE: 18
gccctggata ccaacgacta caaggatgac gacgacaagg ccctggatac caactactgc      60
ttcagctcca cgg                                                         73

<210> SEQ ID NO 19
<211> LENGTH: 72
<212> TYPE: DNA
<213> ORGANISM: Artificial Sequence
<220> FEATURE:
<223> OTHER INFORMATION: Primer

<400> SEQUENCE: 19
cttgtcgtcg tcatccttgt agtcgttatc cagggctcgg cggtggtgcc gggagctgtg      60
caggtgctgg gc                                                          72

<210> SEQ ID NO 20
<211> LENGTH: 1624
<212> TYPE: DNA
<213> ORGANISM: Artificial Sequence
<220> FEATURE:
<223> OTHER INFORMATION: Murine (Mus musculus) TGF-beta1/N+5 HA Fusion
      Construct
<220> FEATURE:
<221> NAME/KEY: 5'UTR
<222> LOCATION: (1)..(347)
<223> OTHER INFORMATION: 5' untranslated region
<220> FEATURE:
<221> NAME/KEY: CDS
<222> LOCATION: (348)..(1571)
<223> OTHER INFORMATION: Protein coding sequence
<220> FEATURE:
<221> NAME/KEY: misc_feature
<222> LOCATION: (1182)..(1196)
<223> OTHER INFORMATION: Encodes amino acid residues 1-5 of TGF-beta1
<220> FEATURE:
<221> NAME/KEY: misc_feature
<222> LOCATION: (1182)..(1571)
<223> OTHER INFORMATION: Encodes mature fusion protein
<220> FEATURE:
<221> NAME/KEY: misc_feature
<222> LOCATION: (1197)..(1232)
<223> OTHER INFORMATION: Encodes HA epitope tag
<220> FEATURE:
<221> NAME/KEY: 3'UTR
<222> LOCATION: (1572)..(1624)
<223> OTHER INFORMATION: 3' untranslated region

<400> SEQUENCE: 20
ccccagcctg cctcttgagt ccctcgcatc ccaggaccct ctctccccg agaggcagat       60 ctccctcgga cctgctggca gtagctcccc tatttaagaa cacccacttt tggatctcag     120
agagcgctca tctcgatttt taccctggtg gtatactgag acaccttggt gtcagagcct     180
caccgcgact cctgctgctt tctccctcaa cctcaaatta ttcaggacta tcacctacct     240
```

-continued

```
ttccttggga gaccccaccc cacaagccct gcagggcgg ggcctccgca tcccacctttt      300 gccgagggtt cccgctctcc gaagtgccgt ggggcgccgc ctccccc atg ccg ccc        356
                                                   Met Pro Pro
                                                   1 tcg ggg ctg cgg cta ctg ccg ctt ctg ctc cca ctc ccg tgg ctt cta        404
Ser Gly Leu Arg Leu Leu Pro Leu Leu Leu Pro Leu Pro Trp Leu Leu
    5                  10                  15 gtg ctg acg ccc ggg agg cca gcc gcg gga ctc tcc acc tgc aag acc        452
Val Leu Thr Pro Gly Arg Pro Ala Ala Gly Leu Ser Thr Cys Lys Thr
 20                  25                  30                  35 atc gac atg gag ctg gtg aaa cgg aag cgc atc gaa gcc atc cgt ggc        500
Ile Asp Met Glu Leu Val Lys Arg Lys Arg Ile Glu Ala Ile Arg Gly
                 40                  45                  50 cag atc ctg tcc aaa cta agg ctc gcc agt ccc cca agc cag ggg gag        548
Gln Ile Leu Ser Lys Leu Arg Leu Ala Ser Pro Pro Ser Gln Gly Glu
                     55                  60                  65 gta ccc ccc ggc ccg ctg ccc gag gcg gtg ctc gct ttg tac aac agc        596
Val Pro Pro Gly Pro Leu Pro Glu Ala Val Leu Ala Leu Tyr Asn Ser
             70                  75                  80 acc cgc gac cgg gtg gca ggc gag agc gcc gac cca gag ccg gag ccc        644
Thr Arg Asp Arg Val Ala Gly Glu Ser Ala Asp Pro Glu Pro Glu Pro
 85                  90                  95 gaa gcg gac tac tat gct aaa gag gtc acc cgc gtg cta atg gtg gac        692
Glu Ala Asp Tyr Tyr Ala Lys Glu Val Thr Arg Val Leu Met Val Asp
100                 105                 110                 115 cgc aac aac gcc atc tat gag aaa acc aaa gac atc tca cac agt ata        740
Arg Asn Asn Ala Ile Tyr Glu Lys Thr Lys Asp Ile Ser His Ser Ile
                    120                 125                 130 tat atg ttc ttc aat acg tca gac att cgg gaa gca gtg ccc gaa ccc        788
Tyr Met Phe Phe Asn Thr Ser Asp Ile Arg Glu Ala Val Pro Glu Pro
                135                 140                 145 cca ttg ctg tcc cgt gca gag ctg cgc ttg cag aga tta aaa tca agt        836
Pro Leu Leu Ser Arg Ala Glu Leu Arg Leu Gln Arg Leu Lys Ser Ser
            150                 155                 160 gtg gag caa cat gtg gaa ctc tac cag aaa tat agc aac aat tcc tgg        884
Val Glu Gln His Val Glu Leu Tyr Gln Lys Tyr Ser Asn Asn Ser Trp
165                 170                 175 cgt tac ctt ggt aac cgg ctg ctg acc ccc act gat acg cct gag tgg        932
Arg Tyr Leu Gly Asn Arg Leu Leu Thr Pro Thr Asp Thr Pro Glu Trp
180                 185                 190                 195 ctg tct ttt gac gtc act gga gtt gta cgg cag tgg ctg aac caa gga        980
Leu Ser Phe Asp Val Thr Gly Val Val Arg Gln Trp Leu Asn Gln Gly
                    200                 205                 210 gac gga ata cag ggc ttt cga ttc agc gct cac tgc tct tgt gac agc       1028
Asp Gly Ile Gln Gly Phe Arg Phe Ser Ala His Cys Ser Cys Asp Ser
                215                 220                 225 aaa gat aac aaa ctc cac gtg gaa atc aac ggg atc agc ccc aaa cgt       1076
Lys Asp Asn Lys Leu His Val Glu Ile Asn Gly Ile Ser Pro Lys Arg
            230                 235                 240 cgg ggc gac ctg ggc acc atc cat gac atg aac cgg ccc ttc ctg ctc       1124
Arg Gly Asp Leu Gly Thr Ile His Asp Met Asn Arg Pro Phe Leu Leu
245                 250                 255 ctc atg gcc acc ccc ctg gaa agg gcc cag cac ctg cac agc tca cgg       1172
Leu Met Ala Thr Pro Leu Glu Arg Ala Gln His Leu His Ser Ser Arg
260                 265                 270                 275 cac cgg aga gcc ctg gat acc aac agc tac cca tac gac gtg cca gac       1220
His Arg Arg Ala Leu Asp Thr Asn Ser Tyr Pro Tyr Asp Val Pro Asp
                280                 285                 290 tac gca tct ctg gcc ctg gat acc aac tat tgc ttc agc tcc aca gag       1268
```

-continued

```
                Tyr Ala Ser Leu Ala Leu Asp Thr Asn Tyr Cys Phe Ser Ser Thr Glu
                        295                 300                 305 aag aac tgc tgt gtg cgg cag ctg tac att gac ttt agg aag gac ctg         1316
Lys Asn Cys Cys Val Arg Gln Leu Tyr Ile Asp Phe Arg Lys Asp Leu
        310                 315                 320 ggt tgg aag tgg atc cac gag ccc aag ggc tac cat gcc aac ttc tgt         1364
Gly Trp Lys Trp Ile His Glu Pro Lys Gly Tyr His Ala Asn Phe Cys
        325                 330                 335 ctg gga ccc tgc ccc tat att tgg agc ctg gac aca cag tac agc aag         1412
Leu Gly Pro Cys Pro Tyr Ile Trp Ser Leu Asp Thr Gln Tyr Ser Lys
340                 345                 350                 355 gtc ctt gcc ctc tac aac caa cac aac ccg ggc gct tcg gcg tca ccg         1460
Val Leu Ala Leu Tyr Asn Gln His Asn Pro Gly Ala Ser Ala Ser Pro
                360                 365                 370 tgc tgc gtg ccg cag gct ttg gag cca ctg ccc atc gtc tac tac gtg         1508
Cys Cys Val Pro Gln Ala Leu Glu Pro Leu Pro Ile Val Tyr Tyr Val
                375                 380                 385 ggt cgc aag ccc aag gtg gag cag ttg tcc aac atg att gtg cgc tcc         1556
Gly Arg Lys Pro Lys Val Glu Gln Leu Ser Asn Met Ile Val Arg Ser
                390                 395                 400 tgc aag tgc agc tga agccccgccc cgcccgccc ctcccggcag gcccggcccc          1611
Cys Lys Cys Ser
        405 gcccccgccc cgc                                                           1624
```

<210> SEQ ID NO 21
<211> LENGTH: 407
<212> TYPE: PRT
<213> ORGANISM: Artificial Sequence
<220> FEATURE:
<223> OTHER INFORMATION: Murine (Mus musculus) TGF-beta1/N+5 HA Fusion
      Construct

<400> SEQUENCE: 21

```
Met Pro Pro Ser Gly Leu Arg Leu Leu Pro Leu Leu Leu Pro Leu Pro
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
                85                  90                  95

Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
        115                 120                 125

His Ser Ile Tyr Met Phe Phe Asn Thr Ser Asp Ile Arg Glu Ala Val
    130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190
```

```
Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
        210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Ser Tyr Pro Tyr Asp
        275                 280                 285

Val Pro Asp Tyr Ala Ser Leu Ala Leu Asp Thr Asn Tyr Cys Phe Ser
        290                 295                 300

Ser Thr Glu Lys Asn Cys Cys Val Arg Gln Leu Tyr Ile Asp Phe Arg
305                 310                 315                 320

Lys Asp Leu Gly Trp Lys Trp Ile His Glu Pro Lys Gly Tyr His Ala
                325                 330                 335

Asn Phe Cys Leu Gly Pro Cys Pro Tyr Ile Trp Ser Leu Asp Thr Gln
            340                 345                 350

Tyr Ser Lys Val Leu Ala Leu Tyr Asn Gln His Asn Pro Gly Ala Ser
        355                 360                 365

Ala Ser Pro Cys Cys Val Pro Gln Ala Leu Glu Pro Leu Pro Ile Val
        370                 375                 380

Tyr Tyr Val Gly Arg Lys Pro Lys Val Glu Gln Leu Ser Asn Met Ile
385                 390                 395                 400

Val Arg Ser Cys Lys Cys Ser
                405
```

<210> SEQ ID NO 22
<211> LENGTH: 108
<212> TYPE: DNA
<213> ORGANISM: Artificial Sequence
<220> FEATURE:
<223> OTHER INFORMATION: Primer

<400> SEQUENCE: 22
gccctggata ccaacagcta cccatacgac gtgccagact acgcatctct ggccctggat    60
accaactact gcttcagctc cacggagaag aactgctgcg tgcggcag                108

<210> SEQ ID NO 23
<211> LENGTH: 73
<212> TYPE: DNA
<213> ORGANISM: Artificial Sequence
<220> FEATURE:
<223> OTHER INFORMATION: Primer

<400> SEQUENCE: 23
cagagatgcg tagtctggca cgtcgtatgg gtagctgttg gtatccaggg ctcggcggtg    60
ccgggagctg tgc                                                       73

<210> SEQ ID NO 24
<211> LENGTH: 1284
<212> TYPE: DNA
<213> ORGANISM: Artificial Sequence
<220> FEATURE:
<223> OTHER INFORMATION: Murine (Mus musculus) TGF-beta2/N+5 FLAG Fusion
      Construct

```
<220> FEATURE:
<221> NAME/KEY: CDS
<222> LOCATION: (1)..(1284)
<223> OTHER INFORMATION: Protein coding sequence
<220> FEATURE:
<221> NAME/KEY: misc_feature
<222> LOCATION: (907)..(921)
<223> OTHER INFORMATION: Encodes amino acid residues 1-5 of TGF-beta2
<220> FEATURE:
<221> NAME/KEY: misc_feature
<222> LOCATION: (907)..(1284)
<223> OTHER INFORMATION: Encodes mature fusion protein
<220> FEATURE:
<221> NAME/KEY: misc_feature
<222> LOCATION: (922)..(945)
<223> OTHER INFORMATION: Encodes FLAG epitope tag

<400> SEQUENCE: 24 atg cac tac tgt gtg ctg agc acc ttt ttg ctc ctg cat ctg gtc ccg      48
Met His Tyr Cys Val Leu Ser Thr Phe Leu Leu Leu His Leu Val Pro
1               5                   10                  15 gtg gcg ctc agt ctg tct acc tgc agc acc ctc gac atg gat cag ttt      96
Val Ala Leu Ser Leu Ser Thr Cys Ser Thr Leu Asp Met Asp Gln Phe
            20                  25                  30 atg cgc aag agg atc gag gcc atc cgc ggg cag atc ctg agc aag ctg     144
Met Arg Lys Arg Ile Glu Ala Ile Arg Gly Gln Ile Leu Ser Lys Leu
        35                  40                  45 aag ctc acc agc ccc ccg gaa gac tat ccg gag ccg gat gag gtc ccc     192
Lys Leu Thr Ser Pro Pro Glu Asp Tyr Pro Glu Pro Asp Glu Val Pro
    50                  55                  60 ccg gag gtg att tcc atc tac aac agt acc agg gac tta ctg cag gag     240
Pro Glu Val Ile Ser Ile Tyr Asn Ser Thr Arg Asp Leu Leu Gln Glu
65                  70                  75                  80 aag gca agc cgg agg gca gcc gcc tgc gag cgc gag cgg agc gag cag     288
Lys Ala Ser Arg Arg Ala Ala Ala Cys Glu Arg Glu Arg Ser Glu Gln
                85                  90                  95 gag tac tac gcc aag gag gtt tat aaa atc gac atg ccg tcc cac ctc     336
Glu Tyr Tyr Ala Lys Glu Val Tyr Lys Ile Asp Met Pro Ser His Leu
            100                 105                 110 ccc tcc gaa aat gcc atc ccg ccc act ttc tac aga ccc tac ttc aga     384
Pro Ser Glu Asn Ala Ile Pro Pro Thr Phe Tyr Arg Pro Tyr Phe Arg
        115                 120                 125 atc gtc cgc ttt gat gtc tca aca atg gag aaa aat gct tcg aat ctg     432
Ile Val Arg Phe Asp Val Ser Thr Met Glu Lys Asn Ala Ser Asn Leu
    130                 135                 140 gtg aag gca gag ttc agg gtc ttc cgc ttg caa aac ccc aaa gcc aga     480
Val Lys Ala Glu Phe Arg Val Phe Arg Leu Gln Asn Pro Lys Ala Arg
145                 150                 155                 160 gtg gcc gag cag cgg att gaa ctg tat cag atc ctt aaa tcc aaa gac     528
Val Ala Glu Gln Arg Ile Glu Leu Tyr Gln Ile Leu Lys Ser Lys Asp
                165                 170                 175 tta aca tct ccc acc cag cgc tac atc gat agc aag gtt gtg aaa acc     576
Leu Thr Ser Pro Thr Gln Arg Tyr Ile Asp Ser Lys Val Val Lys Thr
            180                 185                 190 aga gcg gag ggt gaa tgg ctc tcc ttc gac gtg aca gac gct gtg cag     624
Arg Ala Glu Gly Glu Trp Leu Ser Phe Asp Val Thr Asp Ala Val Gln
        195                 200                 205 gag tgg ctt cac cac aaa gac agg aac ctg ggg ttt aaa ata agt tta     672
Glu Trp Leu His His Lys Asp Arg Asn Leu Gly Phe Lys Ile Ser Leu
    210                 215                 220 cac tgc ccc tgc tgt acc ttc gtg ccg tct aat aat tac atc atc ccg     720
His Cys Pro Cys Cys Thr Phe Val Pro Ser Asn Asn Tyr Ile Ile Pro
225                 230                 235                 240
```

```
aat aaa agc gaa gag ctc gag gcg aga ttt gca ggt att gat ggc acc      768
Asn Lys Ser Glu Glu Leu Glu Ala Arg Phe Ala Gly Ile Asp Gly Thr
            245                 250                 255 tct aca tat gcc agt ggt gat cag aaa act ata aag tcc act agg aaa      816
Ser Thr Tyr Ala Ser Gly Asp Gln Lys Thr Ile Lys Ser Thr Arg Lys
        260                 265                 270 aaa acc agt ggg aag acc cca cat ctc ctg cta atg ttg ttg ccc tcc      864
Lys Thr Ser Gly Lys Thr Pro His Leu Leu Leu Met Leu Leu Pro Ser
    275                 280                 285 tac aga ctg gag tca caa cag tcc agc cgg cgg aag aag cgc gct ttg      912
Tyr Arg Leu Glu Ser Gln Gln Ser Ser Arg Arg Lys Lys Arg Ala Leu
290                 295                 300 gat gct gcc gac tac aag gat gac gac gac aag gct ttg gat gct gcc      960
Asp Ala Ala Asp Tyr Lys Asp Asp Asp Asp Lys Ala Leu Asp Ala Ala
305                 310                 315                 320 tac tgc ttt aga aat gtg cag gat aat tgc tgc ctt cgc cct ctt tac     1008
Tyr Cys Phe Arg Asn Val Gln Asp Asn Cys Cys Leu Arg Pro Leu Tyr
                325                 330                 335 att gat ttt aag agg gat ctt gga tgg aaa tgg atc cat gaa ccc aaa     1056
Ile Asp Phe Lys Arg Asp Leu Gly Trp Lys Trp Ile His Glu Pro Lys
            340                 345                 350 ggg tac aat gct aac ttc tgt gct ggg gca tgc cca tat cta tgg agt     1104
Gly Tyr Asn Ala Asn Phe Cys Ala Gly Ala Cys Pro Tyr Leu Trp Ser
        355                 360                 365 tca gac act caa cac acc aaa gtc ctc agc ctg tac aac acc ata aat     1152
Ser Asp Thr Gln His Thr Lys Val Leu Ser Leu Tyr Asn Thr Ile Asn
    370                 375                 380 ccc gaa gct tcc gct tcc cct tgc tgt gtg tcc cag gat ctg gaa cca     1200
Pro Glu Ala Ser Ala Ser Pro Cys Cys Val Ser Gln Asp Leu Glu Pro
385                 390                 395                 400 ctg acc att ctc tat tac att gga aat acg ccc aag atc gaa cag ctt     1248
Leu Thr Ile Leu Tyr Tyr Ile Gly Asn Thr Pro Lys Ile Glu Gln Leu
                405                 410                 415 tcc aat atg att gtc aag tct tgt aaa tgc agc taa                     1284
Ser Asn Met Ile Val Lys Ser Cys Lys Cys Ser
            420                 425

<210> SEQ ID NO 25
<211> LENGTH: 427
<212> TYPE: PRT
<213> ORGANISM: Artificial Sequence
<220> FEATURE:
<223> OTHER INFORMATION: Murine (Mus musculus) TGF-beta2/N+5 FLAG Fusion
      Construct

<400> SEQUENCE: 25

Met His Tyr Cys Val Leu Ser Thr Phe Leu Leu Leu His Leu Val Pro
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Asp Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Glu Gln
                85                  90                  95

Glu Tyr Tyr Ala Lys Glu Val Tyr Lys Ile Asp Met Pro Ser His Leu
            100                 105                 110
```

```
Pro Ser Glu Asn Ala Ile Pro Pro Thr Phe Tyr Arg Pro Tyr Phe Arg
        115                 120                 125

Ile Val Arg Phe Asp Val Ser Thr Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Ala Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
        180                 185                 190

Arg Ala Glu Gly Glu Trp Leu Ser Phe Asp Val Thr Asp Ala Val Gln
        195                 200                 205

Glu Trp Leu His His Lys Asp Arg Asn Leu Gly Phe Lys Ile Ser Leu
210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Ala Ser Gly Asp Gln Lys Thr Ile Lys Ser Thr Arg Lys
        260                 265                 270

Lys Thr Ser Gly Lys Thr Pro His Leu Leu Leu Met Leu Leu Pro Ser
        275                 280                 285

Tyr Arg Leu Glu Ser Gln Gln Ser Ser Arg Arg Lys Lys Arg Ala Leu
290                 295                 300

Asp Ala Ala Asp Tyr Lys Asp Asp Asp Lys Ala Leu Asp Ala Ala
305                 310                 315                 320

Tyr Cys Phe Arg Asn Val Gln Asp Asn Cys Cys Leu Arg Pro Leu Tyr
                325                 330                 335

Ile Asp Phe Lys Arg Asp Leu Gly Trp Lys Trp Ile His Glu Pro Lys
        340                 345                 350

Gly Tyr Asn Ala Asn Phe Cys Ala Gly Ala Cys Pro Tyr Leu Trp Ser
        355                 360                 365

Ser Asp Thr Gln His Thr Lys Val Leu Ser Leu Tyr Asn Thr Ile Asn
370                 375                 380

Pro Glu Ala Ser Ala Ser Pro Cys Cys Val Ser Gln Asp Leu Glu Pro
385                 390                 395                 400

Leu Thr Ile Leu Tyr Tyr Ile Gly Asn Thr Pro Lys Ile Glu Gln Leu
                405                 410                 415

Ser Asn Met Ile Val Lys Ser Cys Lys Cys Ser
        420                 425

<210> SEQ ID NO 26
<211> LENGTH: 1303
<212> TYPE: DNA
<213> ORGANISM: Artificial Sequence
<220> FEATURE:
<223> OTHER INFORMATION: Murine (Mus musculus) TGF-beta2/N+5 HA Fusion
      Construct
<220> FEATURE:
<221> NAME/KEY: 5'UTR
<222> LOCATION: (1)..(7)
<223> OTHER INFORMATION: 5' untranslated region
<220> FEATURE:
<221> NAME/KEY: CDS
<222> LOCATION: (8)..(1303)
<223> OTHER INFORMATION: Protein coding sequence
<220> FEATURE:
<221> NAME/KEY: misc_feature
```

-continued

```
<222> LOCATION: (914)..(928)
<223> OTHER INFORMATION: Encodes amino acid residues 1-5 of TGF-beta2
<220> FEATURE:
<221> NAME/KEY: misc_feature
<222> LOCATION: (914)..(1303)
<223> OTHER INFORMATION: Encodes mature fusion protein
<220> FEATURE:
<221> NAME/KEY: misc_feature
<222> LOCATION: (929)..(964)
<223> OTHER INFORMATION: Encodes HA epitope tag

<400> SEQUENCE: 26 taaaaac atg cac tac tgt gtg ctg agc acc ttt ttg ctc ctg cat ctg       49
        Met His Tyr Cys Val Leu Ser Thr Phe Leu Leu Leu His Leu
        1               5                   10 gtc ccg gtg gcg ctc agt ctg tct acc tgc agc acc ctc gac atg gat       97
Val Pro Val Ala Leu Ser Leu Ser Thr Cys Ser Thr Leu Asp Met Asp
15              20                  25                  30 cag ttt atg cgc aag agg atc gag gcc atc cgc ggg cag atc ctg agc      145
Gln Phe Met Arg Lys Arg Ile Glu Ala Ile Arg Gly Gln Ile Leu Ser
            35                  40                  45 aag ctg aag ctc acc agc ccc ccg gaa gac tat ccg gag ccg gat gag      193
Lys Leu Lys Leu Thr Ser Pro Pro Glu Asp Tyr Pro Glu Pro Asp Glu
        50                  55                  60 gtc ccc ccg gag gtg att tcc atc tac aac agt acc agg gac tta ctg      241
Val Pro Pro Glu Val Ile Ser Ile Tyr Asn Ser Thr Arg Asp Leu Leu
65              70                  75 cag gag aag gca agc cgg agg gca gcc gcc tgc gag cgc gag cgg agc      289
Gln Glu Lys Ala Ser Arg Arg Ala Ala Ala Cys Glu Arg Glu Arg Ser
            80                  85                  90 gag cag gag tac tac gcc aag gag gtt tat aaa atc gac atg ccg tcc      337
Glu Gln Glu Tyr Tyr Ala Lys Glu Val Tyr Lys Ile Asp Met Pro Ser
95              100                 105                 110 cac ctc ccc tcc gaa aat gcc atc ccg ccc act ttc tac aga ccc tac      385
His Leu Pro Ser Glu Asn Ala Ile Pro Pro Thr Phe Tyr Arg Pro Tyr
            115                 120                 125 ttc aga atc gtc cgc ttt gat gtc tca aca atg gag aaa aat gct tcg      433
Phe Arg Ile Val Arg Phe Asp Val Ser Thr Met Glu Lys Asn Ala Ser
        130                 135                 140 aat ctg gtg aag gca gag ttc agg gtc ttc cgc ttg caa aac ccc aaa      481
Asn Leu Val Lys Ala Glu Phe Arg Val Phe Arg Leu Gln Asn Pro Lys
            145                 150                 155 gcc aga gtg gcc gag cag cgg att gaa ctg tat cag atc ctt aaa tcc      529
Ala Arg Val Ala Glu Gln Arg Ile Glu Leu Tyr Gln Ile Leu Lys Ser
160                 165                 170 aaa gac tta aca tct ccc acc cag cgc tac atc gat agc aag gtt gtg      577
Lys Asp Leu Thr Ser Pro Thr Gln Arg Tyr Ile Asp Ser Lys Val Val
175             180                 185                 190 aaa acc aga gcg gag ggt gaa tgg ctc tcc ttc gac gtg aca gac gct      625
Lys Thr Arg Ala Glu Gly Glu Trp Leu Ser Phe Asp Val Thr Asp Ala
            195                 200                 205 gtg cag gag tgg ctt cac cac aaa gac agg aac ctg ggg ttt aaa ata      673
Val Gln Glu Trp Leu His His Lys Asp Arg Asn Leu Gly Phe Lys Ile
        210                 215                 220 agt tta cac tgc ccc tgc tgt acc ttc gtg ccg tct aat aat tac atc      721
Ser Leu His Cys Pro Cys Cys Thr Phe Val Pro Ser Asn Asn Tyr Ile
            225                 230                 235 atc ccg aat aaa agc gaa gag ctc gag gcg aga ttt gca ggt att gat      769
Ile Pro Asn Lys Ser Glu Glu Leu Glu Ala Arg Phe Ala Gly Ile Asp
        240                 245                 250 ggc acc tct aca tat gcc agt ggt gat cag aaa act ata aag tcc act      817
Gly Thr Ser Thr Tyr Ala Ser Gly Asp Gln Lys Thr Ile Lys Ser Thr
```

-continued

```
                    255                 260                 265                 270
agg aaa aaa acc agt ggg aag acc cca cat ctc ctg cta atg ttg ttg        865
Arg Lys Lys Thr Ser Gly Lys Thr Pro His Leu Leu Leu Met Leu Leu
                275                 280                 285 ccc tcc tac aga ctg gag tca caa cag tcc agc cgg cgg aag aag cgc        913
Pro Ser Tyr Arg Leu Glu Ser Gln Gln Ser Ser Arg Arg Lys Lys Arg
            290                 295                 300 gct ttg gat gct gcc agc tac cca tac gac gtg cca gac tac gca tct        961
Ala Leu Asp Ala Ala Ser Tyr Pro Tyr Asp Val Pro Asp Tyr Ala Ser
        305                 310                 315 ctg gct ttg gat gct gcc tac tgc ttt aga aat gtg cag gat aat tgc       1009
Leu Ala Leu Asp Ala Ala Tyr Cys Phe Arg Asn Val Gln Asp Asn Cys
    320                 325                 330 tgc ctt cgc cct ctt tac att gat ttt aag agg gat ctt gga tgg aaa       1057
Cys Leu Arg Pro Leu Tyr Ile Asp Phe Lys Arg Asp Leu Gly Trp Lys
335                 340                 345                 350 tgg atc cat gaa ccc aaa ggg tac aat gct aac ttc tgt gct ggg gca       1105
Trp Ile His Glu Pro Lys Gly Tyr Asn Ala Asn Phe Cys Ala Gly Ala
                355                 360                 365 tgc cca tat cta tgg agt tca gac act caa cac acc aaa gtc ctc agc       1153
Cys Pro Tyr Leu Trp Ser Ser Asp Thr Gln His Thr Lys Val Leu Ser
            370                 375                 380 ctg tac aac acc ata aat ccc gaa gct tcc gct tcc cct tgc tgt gtg       1201
Leu Tyr Asn Thr Ile Asn Pro Glu Ala Ser Ala Ser Pro Cys Cys Val
        385                 390                 395 tcc cag gat ctg gaa cca ctg acc att ctc tat tac att gga aat acg       1249
Ser Gln Asp Leu Glu Pro Leu Thr Ile Leu Tyr Tyr Ile Gly Asn Thr
    400                 405                 410 ccc aag atc gaa cag ctt tcc aat atg att gtc aag tct tgt aaa tgc       1297
Pro Lys Ile Glu Gln Leu Ser Asn Met Ile Val Lys Ser Cys Lys Cys
415                 420                 425                 430 agc taa                                                                 1303
Ser
```

<210> SEQ ID NO 27
<211> LENGTH: 431
<212> TYPE: PRT
<213> ORGANISM: Artificial Sequence
<220> FEATURE:
<223> OTHER INFORMATION: Murine (Mus musculus) TGF-beta2/N+5 HA Fusion
      Construct

<400> SEQUENCE: 27

```
Met His Tyr Cys Val Leu Ser Thr Phe Leu Leu Leu His Leu Val Pro
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Asp Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Glu Gln
                85                  90                  95

Glu Tyr Tyr Ala Lys Glu Val Tyr Lys Ile Asp Met Pro Ser His Leu
            100                 105                 110

Pro Ser Glu Asn Ala Ile Pro Pro Thr Phe Tyr Arg Pro Tyr Phe Arg
        115                 120                 125
```

```
Ile Val Arg Phe Asp Val Ser Thr Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Ala Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val Gln
        195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Ala Ser Gly Asp Gln Lys Thr Ile Lys Ser Thr Arg Lys
            260                 265                 270

Lys Thr Ser Gly Lys Thr Pro His Leu Leu Leu Met Leu Leu Pro Ser
        275                 280                 285

Tyr Arg Leu Glu Ser Gln Gln Ser Ser Arg Arg Lys Lys Arg Ala Leu
    290                 295                 300

Asp Ala Ala Ser Tyr Pro Tyr Asp Val Pro Asp Tyr Ala Ser Leu Ala
305                 310                 315                 320

Leu Asp Ala Ala Tyr Cys Phe Arg Asn Val Gln Asp Asn Cys Cys Leu
                325                 330                 335

Arg Pro Leu Tyr Ile Asp Phe Lys Arg Asp Leu Gly Trp Lys Trp Ile
            340                 345                 350

His Glu Pro Lys Gly Tyr Asn Ala Asn Phe Cys Ala Gly Ala Cys Pro
        355                 360                 365

Tyr Leu Trp Ser Ser Asp Thr Gln His Thr Lys Val Leu Ser Leu Tyr
    370                 375                 380

Asn Thr Ile Asn Pro Glu Ala Ser Ala Ser Pro Cys Cys Val Ser Gln
385                 390                 395                 400

Asp Leu Glu Pro Leu Thr Ile Leu Tyr Tyr Ile Gly Asn Thr Pro Lys
                405                 410                 415

Ile Glu Gln Leu Ser Asn Met Ile Val Lys Ser Cys Lys Cys Ser
            420                 425                 430

<210> SEQ ID NO 28
<211> LENGTH: 1272
<212> TYPE: DNA
<213> ORGANISM: Artificial Sequence
<220> FEATURE:
<223> OTHER INFORMATION: Murine (Mus musculus) TGF-beta3/N+5 FLAG Fusion
      Construct
<220> FEATURE:
<221> NAME/KEY: CDS
<222> LOCATION: (1)..(1272)
<223> OTHER INFORMATION: Protein coding sequence
<220> FEATURE:
<221> NAME/KEY: misc_feature
<222> LOCATION: (895)..(909)
<223> OTHER INFORMATION: Encodes amino acid residues 1-5 of TGF-beta3
<220> FEATURE:
<221> NAME/KEY: misc_feature
<222> LOCATION: (895)..(1272)
<223> OTHER INFORMATION: Encodes mature fusion protein
<220> FEATURE:
```

-continued

<221> NAME/KEY: misc_feature
<222> LOCATION: (910)..(933)
<223> OTHER INFORMATION: Encodes FLAG epitope tag

<400> SEQUENCE: 28

| | | | | | | | | | | | | | | | | |
|---|---|---|---|---|---|---|---|---|---|---|---|---|---|---|---|---|
| atg | cac | ttg | caa | agg | gct | ctg | gta | gtc | ctg | gcc | ctg | ctg | aac | ttg | gcc | 48 |
| Met | His | Leu | Gln | Arg | Ala | Leu | Val | Val | Leu | Ala | Leu | Leu | Asn | Leu | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aca | atc | agc | ctc | tct | ctg | tcc | act | tgc | acc | acg | ttg | gac | ttc | ggc | cac | 96 |
| Thr | Ile | Ser | Leu | Ser | Leu | Ser | Thr | Cys | Thr | Thr | Leu | Asp | Phe | Gly | His | |
| | | | 20 | | | | | 25 | | | | | 30 | | | |

| | | | | | | | | | | | | | | | | |
|---|---|---|---|---|---|---|---|---|---|---|---|---|---|---|---|---|
| atc | aag | aag | aag | agg | gtg | gaa | gcc | att | agg | gga | cag | atc | ttg | agc | aag | 144 |
| Ile | Lys | Lys | Lys | Arg | Val | Glu | Ala | Ile | Arg | Gly | Gln | Ile | Leu | Ser | Lys | |
| | | | 35 | | | | | 40 | | | | | 45 | | | |

| | | | | | | | | | | | | | | | | |
|---|---|---|---|---|---|---|---|---|---|---|---|---|---|---|---|---|
| ctc | agg | ctc | acc | agc | ccc | cct | gag | cca | tcg | gtg | atg | acc | cac | gtc | ccc | 192 |
| Leu | Arg | Leu | Thr | Ser | Pro | Pro | Glu | Pro | Ser | Val | Met | Thr | His | Val | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| tat | cag | gtc | ctg | gca | ctt | tac | aac | agc | acc | cgg | gag | ttg | ctg | gaa | gag | 240 |
| Tyr | Gln | Val | Leu | Ala | Leu | Tyr | Asn | Ser | Thr | Arg | Glu | Leu | Leu | Glu | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | cac | ggg | gag | agg | gag | gaa | ggc | tgc | act | cag | gag | acc | tcg | gag | tct | 288 |
| Met | His | Gly | Glu | Arg | Glu | Glu | Gly | Cys | Thr | Gln | Glu | Thr | Ser | Glu | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| gag | tac | tat | gcc | aaa | gag | atc | cat | aaa | ttc | gac | atg | atc | cag | gga | ctg | 336 |
| Glu | Tyr | Tyr | Ala | Lys | Glu | Ile | His | Lys | Phe | Asp | Met | Ile | Gln | Gly | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gcg | gag | cac | aat | gaa | ctg | gcc | gtc | tgc | ccc | aaa | gga | att | acc | tct | aag | 384 |
| Ala | Glu | His | Asn | Glu | Leu | Ala | Val | Cys | Pro | Lys | Gly | Ile | Thr | Ser | Lys | |
| | | | 115 | | | | | 120 | | | | | 125 | | | |

| | | | | | | | | | | | | | | | | |
|---|---|---|---|---|---|---|---|---|---|---|---|---|---|---|---|---|
| gtt | ttt | cgt | ttc | aat | gtg | tcc | tca | gtg | gag | aaa | aat | gga | acc | aat | ctg | 432 |
| Val | Phe | Arg | Phe | Asn | Val | Ser | Ser | Val | Glu | Lys | Asn | Gly | Thr | Asn | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| ttc | cgg | gca | gag | ttc | cgg | gtc | ttg | cgg | gtg | ccc | aac | ccc | agc | tcc | aag | 480 |
| Phe | Arg | Ala | Glu | Phe | Arg | Val | Leu | Arg | Val | Pro | Asn | Pro | Ser | Ser | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgc | aca | gag | cag | aga | att | gag | ctc | ttc | cag | ata | ctt | cga | ccg | gat | gag | 528 |
| Arg | Thr | Glu | Gln | Arg | Ile | Glu | Leu | Phe | Gln | Ile | Leu | Arg | Pro | Asp | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| cac | ata | gcc | aag | cag | cgc | tac | ata | ggt | ggc | aag | aat | ctg | ccc | aca | agg | 576 |
| His | Ile | Ala | Lys | Gln | Arg | Tyr | Ile | Gly | Gly | Lys | Asn | Leu | Pro | Thr | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| ggc | acc | gct | gaa | tgg | ctg | tct | ttc | gat | gtc | act | gac | act | gtg | cgc | gag | 624 |
| Gly | Thr | Ala | Glu | Trp | Leu | Ser | Phe | Asp | Val | Thr | Asp | Thr | Val | Arg | Glu | |
| | | | 195 | | | | | 200 | | | | | 205 | | | |

| | | | | | | | | | | | | | | | | |
|---|---|---|---|---|---|---|---|---|---|---|---|---|---|---|---|---|
| tgg | ctg | ttg | agg | aga | gag | tcc | aac | ttg | ggt | ctg | gaa | atc | agc | atc | cac | 672 |
| Trp | Leu | Leu | Arg | Arg | Glu | Ser | Asn | Leu | Gly | Leu | Glu | Ile | Ser | Ile | His | |
| | 210 | | | | | 215 | | | | | 220 | | | | | |

| | | | | | | | | | | | | | | | | |
|---|---|---|---|---|---|---|---|---|---|---|---|---|---|---|---|---|
| tgt | cca | tgt | cac | acc | ttt | cag | ccc | aat | gga | gac | ata | ctg | gaa | aat | gtt | 720 |
| Cys | Pro | Cys | His | Thr | Phe | Gln | Pro | Asn | Gly | Asp | Ile | Leu | Glu | Asn | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cat | gag | gtg | atg | gaa | atc | aaa | ttc | aaa | gga | gtg | gac | aat | gaa | gat | gac | 768 |
| His | Glu | Val | Met | Glu | Ile | Lys | Phe | Lys | Gly | Val | Asp | Asn | Glu | Asp | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| cat | ggc | cgt | gga | gac | ctg | ggg | cgt | ctc | aag | aag | caa | aag | gat | cac | cac | 816 |
| His | Gly | Arg | Gly | Asp | Leu | Gly | Arg | Leu | Lys | Lys | Gln | Lys | Asp | His | His | |
| | | | 260 | | | | | 265 | | | | | 270 | | | |

| | | | | | | | | | | | | | | | | |
|---|---|---|---|---|---|---|---|---|---|---|---|---|---|---|---|---|
| aac | cca | cac | ctg | atc | ctc | atg | atg | atc | ccc | cca | cac | cga | ctg | gac | agc | 864 |
| Asn | Pro | His | Leu | Ile | Leu | Met | Met | Ile | Pro | Pro | His | Arg | Leu | Asp | Ser | |
| | | | 275 | | | | | 280 | | | | | 285 | | | |

| | | | | | | | | | | | | | | | | |
|---|---|---|---|---|---|---|---|---|---|---|---|---|---|---|---|---|
| cca | ggc | cag | ggc | agt | cag | agg | aag | aag | agg | gcc | ctg | gac | acc | aat | gac | 912 |

```
Pro Gly Gln Gly Ser Gln Arg Lys Lys Arg Ala Leu Asp Thr Asn Asp
    290                 295                 300 tac aag gat gac gac gac aag gcc ctg gac acc aat tac tgc ttc cgc       960
Tyr Lys Asp Asp Asp Asp Lys Ala Leu Asp Thr Asn Tyr Cys Phe Arg
305                 310                 315                 320 aac ctg gag gag aac tgc tgt gta cgc ccc ctt tat att gac ttc cgg      1008
Asn Leu Glu Glu Asn Cys Cys Val Arg Pro Leu Tyr Ile Asp Phe Arg
                325                 330                 335 cag gat cta ggc tgg aaa tgg gtc cac gaa cct aag ggt tac tat gcc      1056
Gln Asp Leu Gly Trp Lys Trp Val His Glu Pro Lys Gly Tyr Tyr Ala
            340                 345                 350 aac ttc tgc tca ggc cct tgc cca tac ctc cgc agc gca gac aca acc      1104
Asn Phe Cys Ser Gly Pro Cys Pro Tyr Leu Arg Ser Ala Asp Thr Thr
            355                 360                 365 cat agc acg gtg ctt gga cta tac aac acc ctg aac cca gag gcg tct      1152
His Ser Thr Val Leu Gly Leu Tyr Asn Thr Leu Asn Pro Glu Ala Ser
370                 375                 380 gcc tcg cca tgc tgc gtc ccc cag gac ctg gag ccc ctg acc atc ttg      1200
Ala Ser Pro Cys Cys Val Pro Gln Asp Leu Glu Pro Leu Thr Ile Leu
385                 390                 395                 400 tac tat gtg ggc aga acc ccc aag gtg gag cag ctg tcc aac atg gtg      1248
Tyr Tyr Val Gly Arg Thr Pro Lys Val Glu Gln Leu Ser Asn Met Val
                405                 410                 415 gtg aag tcg tgt aag tgc agc tga                                      1272
Val Lys Ser Cys Lys Cys Ser
            420
```

<210> SEQ ID NO 29
<211> LENGTH: 423
<212> TYPE: PRT
<213> ORGANISM: Artificial Sequence
<220> FEATURE:
<223> OTHER INFORMATION: Murine (Mus musculus) TGF-beta3/N+5 FLAG Fusion
      Construct

<400> SEQUENCE: 29

```
Met His Leu Gln Arg Ala Leu Val Val Leu Ala Leu Leu Asn Leu Ala
1               5                   10                  15

Thr Ile Ser Leu Ser Leu Ser Thr Cys Thr Thr Leu Asp Phe Gly His
                20                  25                  30

Ile Lys Lys Lys Arg Val Glu Ala Ile Arg Gly Gln Ile Leu Ser Lys
            35                  40                  45

Leu Arg Leu Thr Ser Pro Pro Glu Pro Ser Val Met Thr His Val Pro
        50                  55                  60

Tyr Gln Val Leu Ala Leu Tyr Asn Ser Thr Arg Glu Leu Leu Glu Glu
65                  70                  75                  80

Met His Gly Glu Arg Glu Glu Gly Cys Thr Gln Glu Thr Ser Glu Ser
                85                  90                  95

Glu Tyr Tyr Ala Lys Glu Ile His Lys Phe Asp Met Ile Gln Gly Leu
            100                 105                 110

Ala Glu His Asn Glu Leu Ala Val Cys Pro Lys Gly Ile Thr Ser Lys
        115                 120                 125

Val Phe Arg Phe Asn Val Ser Ser Val Glu Lys Asn Gly Thr Asn Leu
130                 135                 140

Phe Arg Ala Glu Phe Arg Val Leu Arg Val Pro Asn Pro Ser Ser Lys
145                 150                 155                 160

Arg Thr Glu Gln Arg Ile Glu Leu Phe Gln Ile Leu Arg Pro Asp Glu
                165                 170                 175
```

```
His Ile Ala Lys Gln Arg Tyr Ile Gly Gly Lys Asn Leu Pro Thr Arg
            180                 185                 190

Gly Thr Ala Glu Trp Leu Ser Phe Asp Val Thr Asp Thr Val Arg Glu
            195                 200                 205

Trp Leu Leu Arg Arg Glu Ser Asn Leu Gly Leu Glu Ile Ser Ile His
    210                 215                 220

Cys Pro Cys His Thr Phe Gln Pro Asn Gly Asp Ile Leu Glu Asn Val
225                 230                 235                 240

His Glu Val Met Glu Ile Lys Phe Lys Gly Val Asp Asn Glu Asp Asp
                245                 250                 255

His Gly Arg Gly Asp Leu Gly Arg Leu Lys Lys Gln Lys Asp His His
            260                 265                 270

Asn Pro His Leu Ile Leu Met Met Ile Pro Pro His Arg Leu Asp Ser
        275                 280                 285

Pro Gly Gln Gly Ser Gln Arg Lys Lys Arg Ala Leu Asp Thr Asn Asp
290                 295                 300

Tyr Lys Asp Asp Asp Lys Ala Leu Asp Thr Asn Tyr Cys Phe Arg
305                 310                 315                 320

Asn Leu Glu Glu Asn Cys Cys Val Arg Pro Leu Tyr Ile Asp Phe Arg
                325                 330                 335

Gln Asp Leu Gly Trp Lys Trp Val His Glu Pro Lys Gly Tyr Tyr Ala
            340                 345                 350

Asn Phe Cys Ser Gly Pro Cys Pro Tyr Leu Arg Ser Ala Asp Thr Thr
        355                 360                 365

His Ser Thr Val Leu Gly Leu Tyr Asn Thr Leu Asn Pro Glu Ala Ser
    370                 375                 380

Ala Ser Pro Cys Cys Val Pro Gln Asp Leu Glu Pro Leu Thr Ile Leu
385                 390                 395                 400

Tyr Tyr Val Gly Arg Thr Pro Lys Val Glu Gln Leu Ser Asn Met Val
                405                 410                 415

Val Lys Ser Cys Lys Cys Ser
            420

<210> SEQ ID NO 30
<211> LENGTH: 1284
<212> TYPE: DNA
<213> ORGANISM: Artificial Sequence
<220> FEATURE:
<223> OTHER INFORMATION: Murine (Mus musculus) TGF-beta3/N+5 HA Fusion
      Construct
<220> FEATURE:
<221> NAME/KEY: CDS
<222> LOCATION: (1)..(1284)
<223> OTHER INFORMATION: Protein coding sequence
<220> FEATURE:
<221> NAME/KEY: misc_feature
<222> LOCATION: (895)..(909)
<223> OTHER INFORMATION: Encodes amino acid residues 1-5 of TGF-beta3
<220> FEATURE:
<221> NAME/KEY: misc_feature
<222> LOCATION: (895)..(1284)
<223> OTHER INFORMATION: Encodes mature fusion protein
<220> FEATURE:
<221> NAME/KEY: misc_feature
<222> LOCATION: (910)..(945)
<223> OTHER INFORMATION: Encodes HA epitope tag

<400> SEQUENCE: 30 atg cac ttg caa agg gct ctg gta gtc ctg gcc ctg ctg aac ttg gcc     48
Met His Leu Gln Arg Ala Leu Val Val Leu Ala Leu Leu Asn Leu Ala
1               5                   10                  15
```

```
aca atc agc ctc tct ctg tcc act tgc acc acg ttg gac ttc ggc cac        96
Thr Ile Ser Leu Ser Leu Ser Thr Cys Thr Thr Leu Asp Phe Gly His
         20                  25                  30 atc aag aag aag agg gtg gaa gcc att agg gga cag atc ttg agc aag       144
Ile Lys Lys Lys Arg Val Glu Ala Ile Arg Gly Gln Ile Leu Ser Lys
         35                  40                  45 ctc agg ctc acc agc ccc cct gag cca tcg gtg atg acc cac gtc ccc       192
Leu Arg Leu Thr Ser Pro Pro Glu Pro Ser Val Met Thr His Val Pro
 50                  55                  60 tat cag gtc ctg gca ctt tac aac agc acc cgg gag ttg ctg gaa gag       240
Tyr Gln Val Leu Ala Leu Tyr Asn Ser Thr Arg Glu Leu Leu Glu Glu
 65                  70                  75                  80 atg cac ggg gag agg gag gaa ggc tgc act cag gag acc tcg gag tct       288
Met His Gly Glu Arg Glu Glu Gly Cys Thr Gln Glu Thr Ser Glu Ser
                 85                  90                  95 gag tac tat gcc aaa gag atc cat aaa ttc gac atg atc cag gga ctg       336
Glu Tyr Tyr Ala Lys Glu Ile His Lys Phe Asp Met Ile Gln Gly Leu
                100                 105                 110 gcg gag cac aat gaa ctg gcc gtc tgc ccc aaa gga att acc tct aag       384
Ala Glu His Asn Glu Leu Ala Val Cys Pro Lys Gly Ile Thr Ser Lys
            115                 120                 125 gtt ttt cgt ttc aat gtg tcc tca gtg gag aaa aat gga acc aat ctg       432
Val Phe Arg Phe Asn Val Ser Ser Val Glu Lys Asn Gly Thr Asn Leu
130                 135                 140 ttc cgg gca gag ttc cgg gtc ttg cgg gtg ccc aac ccc agc tcc aag       480
Phe Arg Ala Glu Phe Arg Val Leu Arg Val Pro Asn Pro Ser Ser Lys
145                 150                 155                 160 cgc aca gag cag aga att gag ctc ttc cag ata ctt cga ccg gat gag       528
Arg Thr Glu Gln Arg Ile Glu Leu Phe Gln Ile Leu Arg Pro Asp Glu
                165                 170                 175 cac ata gcc aag cag cgc tac ata ggt ggc aag aat ctg ccc aca agg       576
His Ile Ala Lys Gln Arg Tyr Ile Gly Gly Lys Asn Leu Pro Thr Arg
            180                 185                 190 ggc acc gct gaa tgg ctg tct ttc gat gtc act gac act gtg cgc gag       624
Gly Thr Ala Glu Trp Leu Ser Phe Asp Val Thr Asp Thr Val Arg Glu
        195                 200                 205 tgg ctg ttg agg aga gag tcc aac ttg ggt ctg gaa atc agc atc cac       672
Trp Leu Leu Arg Arg Glu Ser Asn Leu Gly Leu Glu Ile Ser Ile His
    210                 215                 220 tgt cca tgt cac acc ttt cag ccc aat gga gac ata ctg gaa aat gtt       720
Cys Pro Cys His Thr Phe Gln Pro Asn Gly Asp Ile Leu Glu Asn Val
225                 230                 235                 240 cat gag gtg atg gaa atc aaa ttc aaa gga gtg gac aat gaa gat gac       768
His Glu Val Met Glu Ile Lys Phe Lys Gly Val Asp Asn Glu Asp Asp
                245                 250                 255 cat ggc cgt gga gac ctg ggg cgt ctc aag aag caa aag gat cac cac       816
His Gly Arg Gly Asp Leu Gly Arg Leu Lys Lys Gln Lys Asp His His
            260                 265                 270 aac cca cac ctg atc ctc atg atg atc ccc cca cac cga ctg gac agc       864
Asn Pro His Leu Ile Leu Met Met Ile Pro Pro His Arg Leu Asp Ser
        275                 280                 285 cca ggc cag ggc agt cag agg aag aag agg gcc ctg gac acc aat agc       912
Pro Gly Gln Gly Ser Gln Arg Lys Lys Arg Ala Leu Asp Thr Asn Ser
    290                 295                 300 tac cca tac gac gtg cca gac tac gca tct ctg gcc ctg gac acc aat       960
Tyr Pro Tyr Asp Val Pro Asp Tyr Ala Ser Leu Ala Leu Asp Thr Asn
305                 310                 315                 320 tac tgc ttc cgc aac ctg gag gag aac tgc tgt gta cgc ccc ctt tat      1008
Tyr Cys Phe Arg Asn Leu Glu Glu Asn Cys Cys Val Arg Pro Leu Tyr
                325                 330                 335
```

```
att gac ttc cgg cag gat cta ggc tgg aaa tgg gtc cac gaa cct aag      1056
Ile Asp Phe Arg Gln Asp Leu Gly Trp Lys Trp Val His Glu Pro Lys
        340                 345                 350 ggt tac tat gcc aac ttc tgc tca ggc cct tgc cca tac ctc cgc agc      1104
Gly Tyr Tyr Ala Asn Phe Cys Ser Gly Pro Cys Pro Tyr Leu Arg Ser
            355                 360                 365 gca gac aca acc cat agc acg gtg ctt gga cta tac aac acc ctg aac      1152
Ala Asp Thr Thr His Ser Thr Val Leu Gly Leu Tyr Asn Thr Leu Asn
370                 375                 380 cca gag gcg tct gcc tcg cca tgc tgc gtc ccc cag gac ctg gag ccc      1200
Pro Glu Ala Ser Ala Ser Pro Cys Cys Val Pro Gln Asp Leu Glu Pro
385                 390                 395                 400 ctg acc atc ttg tac tat gtg ggc aga acc ccc aag gtg gag cag ctg      1248
Leu Thr Ile Leu Tyr Tyr Val Gly Arg Thr Pro Lys Val Glu Gln Leu
                405                 410                 415 tcc aac atg gtg gtg aag tcg tgt aag tgc agc tga                      1284
Ser Asn Met Val Val Lys Ser Cys Lys Cys Ser
                420                 425
```

<210> SEQ ID NO 31
<211> LENGTH: 427
<212> TYPE: PRT
<213> ORGANISM: Artificial Sequence
<220> FEATURE:
<223> OTHER INFORMATION: Murine (Mus musculus) TGF-beta3/N+5 HA Fusion
      Construct

<400> SEQUENCE: 31

```
Met His Leu Gln Arg Ala Leu Val Val Leu Ala Leu Leu Asn Leu Ala
1               5                   10                  15

Thr Ile Ser Leu Ser Leu Ser Thr Cys Thr Thr Leu Asp Phe Gly His
            20                  25                  30

Ile Lys Lys Lys Arg Val Glu Ala Ile Arg Gly Gln Ile Leu Ser Lys
        35                  40                  45

Leu Arg Leu Thr Ser Pro Pro Glu Pro Ser Val Met Thr His Val Pro
    50                  55                  60

Tyr Gln Val Leu Ala Leu Tyr Asn Ser Thr Arg Glu Leu Leu Glu Glu
65                  70                  75                  80

Met His Gly Glu Arg Glu Glu Gly Cys Thr Gln Glu Thr Ser Glu Ser
                85                  90                  95

Glu Tyr Tyr Ala Lys Glu Ile His Lys Phe Asp Met Ile Gln Gly Leu
            100                 105                 110

Ala Glu His Asn Glu Leu Ala Val Cys Pro Lys Gly Ile Thr Ser Lys
        115                 120                 125

Val Phe Arg Phe Asn Val Ser Ser Val Glu Lys Asn Gly Thr Asn Leu
    130                 135                 140

Phe Arg Ala Glu Phe Arg Val Leu Arg Val Pro Asn Pro Ser Ser Lys
145                 150                 155                 160

Arg Thr Glu Gln Arg Ile Glu Leu Phe Gln Ile Leu Arg Pro Asp Glu
                165                 170                 175

His Ile Ala Lys Gln Arg Tyr Ile Gly Gly Lys Asn Leu Pro Thr Arg
            180                 185                 190

Gly Thr Ala Glu Trp Leu Ser Phe Asp Val Thr Asp Thr Val Arg Glu
        195                 200                 205

Trp Leu Leu Arg Arg Glu Ser Asn Leu Gly Leu Glu Ile Ser Ile His
    210                 215                 220

Cys Pro Cys His Thr Phe Gln Pro Asn Gly Asp Ile Leu Glu Asn Val
```

```
                225                 230                 235                 240
His Glu Val Met Glu Ile Lys Phe Lys Gly Val Asp Asn Glu Asp Asp
                    245                 250                 255

His Gly Arg Gly Asp Leu Gly Arg Leu Lys Lys Gln Lys Asp His His
            260                 265                 270

Asn Pro His Leu Ile Leu Met Met Ile Pro Pro His Arg Leu Asp Ser
        275                 280                 285

Pro Gly Gln Gly Ser Gln Arg Lys Lys Arg Ala Leu Asp Thr Asn Ser
    290                 295                 300

Tyr Pro Tyr Asp Val Pro Asp Tyr Ala Ser Leu Ala Leu Asp Thr Asn
305                 310                 315                 320

Tyr Cys Phe Arg Asn Leu Glu Glu Asn Cys Cys Val Arg Pro Leu Tyr
                325                 330                 335

Ile Asp Phe Arg Gln Asp Leu Gly Trp Lys Trp Val His Glu Pro Lys
            340                 345                 350

Gly Tyr Tyr Ala Asn Phe Cys Ser Gly Pro Cys Pro Tyr Leu Arg Ser
        355                 360                 365

Ala Asp Thr Thr His Ser Thr Val Leu Gly Leu Tyr Asn Thr Leu Asn
    370                 375                 380

Pro Glu Ala Ser Ala Ser Pro Cys Cys Val Pro Gln Asp Leu Glu Pro
385                 390                 395                 400

Leu Thr Ile Leu Tyr Tyr Val Gly Arg Thr Pro Lys Val Glu Gln Leu
                405                 410                 415

Ser Asn Met Val Val Lys Ser Cys Lys Cys Ser
            420                 425

<210> SEQ ID NO 32
<211> LENGTH: 1349
<212> TYPE: DNA
<213> ORGANISM: Artificial Sequence
<220> FEATURE:
<223> OTHER INFORMATION: Porcine (Sus scrofa) TGF-beta1/N+5 FLAG Fusion
      Construct
<220> FEATURE:
<221> NAME/KEY: 5'UTR
<222> LOCATION: (1)..(10)
<223> OTHER INFORMATION: 5' untranslated region
<220> FEATURE:
<221> NAME/KEY: CDS
<222> LOCATION: (11)..(1222)
<223> OTHER INFORMATION: Protein coding sequence
<220> FEATURE:
<221> NAME/KEY: misc_feature
<222> LOCATION: (845)..(859)
<223> OTHER INFORMATION: Encodes amino acid residues 1-5 of TGF-beta1
<220> FEATURE:
<221> NAME/KEY: misc_feature
<222> LOCATION: (845)..(1222)
<223> OTHER INFORMATION: Encodes mature fusion protein
<220> FEATURE:
<221> NAME/KEY: misc_feature
<222> LOCATION: (860)..(883)
<223> OTHER INFORMATION: Encodes FLAG epitope tag
<220> FEATURE:
<221> NAME/KEY: 3'UTR
<222> LOCATION: (1223)..(1349)
<223> OTHER INFORMATION: 3' untranslated region

<400> SEQUENCE: 32
tggtaccgag atg gcg cct tcg ggg ctg cgg ctc ttg ccg ctg ctg ctg           49
            Met Ala Pro Ser Gly Leu Arg Leu Leu Pro Leu Leu Leu
              1               5                  10 ccg ctg ctg tgg ctg cta gtg ctg acg cct ggc cgg ccg gcc gcc gga         97
Pro Leu Leu Trp Leu Leu Val Leu Thr Pro Gly Arg Pro Ala Ala Gly
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 15  |     |     |     |     | 20  |     |     |     |     | 25  |     |     |      |
| ctg | tcc | acc | tgc | aag | acc | atc | gac | atg | gag | ctg | gtg | aag | cgg | aag | cgc | 145  |
| Leu | Ser | Thr | Cys | Lys | Thr | Ile | Asp | Met | Glu | Leu | Val | Lys | Arg | Lys | Arg |      |
| 30  |     |     |     |     | 35  |     |     |     |     | 40  |     |     |     |     | 45  |      |
| atc | gag | gcc | att | cgc | ggc | cag | att | ctg | tcc | aag | ctt | cgg | ctt | gcc | agc | 193  |
| Ile | Glu | Ala | Ile | Arg | Gly | Gln | Ile | Leu | Ser | Lys | Leu | Arg | Leu | Ala | Ser |      |
|     |     |     |     |     | 50  |     |     |     |     | 55  |     |     |     |     | 60  |      |
| ccc | ccg | agc | cag | ggg | gac | gtg | ccg | ccc | ggc | ccg | ctg | cct | gag | gca | gta | 241  |
| Pro | Pro | Ser | Gln | Gly | Asp | Val | Pro | Pro | Gly | Pro | Leu | Pro | Glu | Ala | Val |      |
|     |     |     |     | 65  |     |     |     |     | 70  |     |     |     |     | 75  |     |      |
| ctg | gct | ctt | tac | aac | agt | acc | cgc | gac | cgg | gta | gcc | ggg | gaa | agt | gtc | 289  |
| Leu | Ala | Leu | Tyr | Asn | Ser | Thr | Arg | Asp | Arg | Val | Ala | Gly | Glu | Ser | Val |      |
|     |     |     | 80  |     |     |     |     | 85  |     |     |     |     | 90  |     |     |      |
| gaa | ccg | gag | ccc | gag | cca | gag | gcg | gac | tac | tac | gcc | aag | gag | gtc | acc | 337  |
| Glu | Pro | Glu | Pro | Glu | Pro | Glu | Ala | Asp | Tyr | Tyr | Ala | Lys | Glu | Val | Thr |      |
|     |     | 95  |     |     |     |     | 100 |     |     |     |     | 105 |     |     |     |      |
| cgc | gtg | cta | atg | gtg | gaa | agc | ggc | aac | caa | atc | tat | gat | aaa | ttc | aag | 385  |
| Arg | Val | Leu | Met | Val | Glu | Ser | Gly | Asn | Gln | Ile | Tyr | Asp | Lys | Phe | Lys |      |
| 110 |     |     |     |     | 115 |     |     |     |     | 120 |     |     |     |     | 125 |      |
| ggc | acc | ccc | cac | agc | tta | tat | atg | ctg | ttc | aac | acg | tcg | gag | ctc | cgg | 433  |
| Gly | Thr | Pro | His | Ser | Leu | Tyr | Met | Leu | Phe | Asn | Thr | Ser | Glu | Leu | Arg |      |
|     |     |     |     | 130 |     |     |     |     | 135 |     |     |     |     | 140 |     |      |
| gaa | gcg | gtg | ccg | gaa | cct | gta | ttg | ctc | tct | cgg | gca | gag | ctg | cgc | ctg | 481  |
| Glu | Ala | Val | Pro | Glu | Pro | Val | Leu | Leu | Ser | Arg | Ala | Glu | Leu | Arg | Leu |      |
|     |     |     | 145 |     |     |     |     | 150 |     |     |     |     | 155 |     |     |      |
| ctg | agg | ctc | aag | tta | aaa | gtg | gag | cag | cac | gtg | gag | cta | tac | cag | aaa | 529  |
| Leu | Arg | Leu | Lys | Leu | Lys | Val | Glu | Gln | His | Val | Glu | Leu | Tyr | Gln | Lys |      |
|     |     |     | 160 |     |     |     |     | 165 |     |     |     |     | 170 |     |     |      |
| tac | agc | aat | gat | tcc | tgg | cgc | tac | ctc | agc | aac | cgg | ctg | ctg | gcc | ccc | 577  |
| Tyr | Ser | Asn | Asp | Ser | Trp | Arg | Tyr | Leu | Ser | Asn | Arg | Leu | Leu | Ala | Pro |      |
|     | 175 |     |     |     |     | 180 |     |     |     |     | 185 |     |     |     |     |      |
| agt | gac | tca | ccg | gag | tgg | ctg | tcc | ttt | gat | gtc | acc | gga | gtt | gtg | cgg | 625  |
| Ser | Asp | Ser | Pro | Glu | Trp | Leu | Ser | Phe | Asp | Val | Thr | Gly | Val | Val | Arg |      |
| 190 |     |     |     |     | 195 |     |     |     |     | 200 |     |     |     |     | 205 |      |
| cag | tgg | ctg | acc | cgc | aga | gag | gct | ata | gag | ggt | ttt | cgc | ctc | agt | gcc | 673  |
| Gln | Trp | Leu | Thr | Arg | Arg | Glu | Ala | Ile | Glu | Gly | Phe | Arg | Leu | Ser | Ala |      |
|     |     |     |     | 210 |     |     |     |     | 215 |     |     |     |     | 220 |     |      |
| cac | tct | tcc | tct | gac | agc | aaa | gat | aac | aca | ctc | cac | gtg | gaa | att | aac | 721  |
| His | Ser | Ser | Ser | Asp | Ser | Lys | Asp | Asn | Thr | Leu | His | Val | Glu | Ile | Asn |      |
|     |     |     | 225 |     |     |     |     | 230 |     |     |     |     | 235 |     |     |      |
| ggg | ttc | aat | tct | ggc | cgc | cgg | ggt | gac | ctg | gcc | acc | att | cac | ggc | atg | 769  |
| Gly | Phe | Asn | Ser | Gly | Arg | Arg | Gly | Asp | Leu | Ala | Thr | Ile | His | Gly | Met |      |
|     |     | 240 |     |     |     |     | 245 |     |     |     |     | 250 |     |     |     |      |
| aac | cgg | ccc | ttc | ctg | ctc | ctc | atg | gcc | acc | ccg | ctg | gag | agg | gcc | cag | 817  |
| Asn | Arg | Pro | Phe | Leu | Leu | Leu | Met | Ala | Thr | Pro | Leu | Glu | Arg | Ala | Gln |      |
|     | 255 |     |     |     |     | 260 |     |     |     |     | 265 |     |     |     |     |      |
| cac | ctg | cac | agc | tcc | cgg | cac | cgc | cga | gcc | ctg | gat | acc | aac | gac | tac | 865  |
| His | Leu | His | Ser | Ser | Arg | His | Arg | Arg | Ala | Leu | Asp | Thr | Asn | Asp | Tyr |      |
| 270 |     |     |     |     | 275 |     |     |     |     | 280 |     |     |     |     | 285 |      |
| aag | gat | gac | gac | gac | aag | gcc | ctg | gat | acc | aac | tac | tgc | ttc | agc | tcc | 913  |
| Lys | Asp | Asp | Asp | Asp | Lys | Ala | Leu | Asp | Thr | Asn | Tyr | Cys | Phe | Ser | Ser |      |
|     |     |     |     | 290 |     |     |     |     | 295 |     |     |     |     | 300 |     |      |
| acg | gag | aag | aac | tgc | tgc | gtg | cgg | cag | ctc | tac | att | gac | ttc | cgg | aag | 961  |
| Thr | Glu | Lys | Asn | Cys | Cys | Val | Arg | Gln | Leu | Tyr | Ile | Asp | Phe | Arg | Lys |      |
|     |     |     |     | 305 |     |     |     |     | 310 |     |     |     |     | 315 |     |      |
| gac | ctg | ggc | tgg | aag | tgg | att | cat | gaa | ccc | aag | ggc | tac | cat | gcc | aat | 1009 |
| Asp | Leu | Gly | Trp | Lys | Trp | Ile | His | Glu | Pro | Lys | Gly | Tyr | His | Ala | Asn |      |
|     |     | 320 |     |     |     |     | 325 |     |     |     |     | 330 |     |     |     |      |
| ttc | tgc | ctg | ggg | ccc | tgt | ccc | tac | atc | tgg | agc | cta | gac | act | cag | tac | 1057 |

```
                Phe Cys Leu Gly Pro Cys Pro Tyr Ile Trp Ser Leu Asp Thr Gln Tyr
                    335                 340                 345 agc aag gtc ctg gct ctg tac aac cag cac aac ccg ggc gcg tcg gcg                1105
Ser Lys Val Leu Ala Leu Tyr Asn Gln His Asn Pro Gly Ala Ser Ala
350                 355                 360                 365 gcg ccg tgc tgc gtg ccg cag gcg ctg gag cca ctg ccc atc gtg tac                1153
Ala Pro Cys Cys Val Pro Gln Ala Leu Glu Pro Leu Pro Ile Val Tyr
                370                 375                 380 tac gtg ggc cgc aag ccc aag gtg gag cag ctg tcc aac atg atc gtg                1201
Tyr Val Gly Arg Lys Pro Lys Val Glu Gln Leu Ser Asn Met Ile Val
            385                 390                 395 cgt tcc tgc aag tgc agc tga ggccccgccc cgcccacagc ccgcccacc                    1252
Arg Ser Cys Lys Cys Ser
            400 cggcaggccc ggccccaccc ccgcccgcct caccggggct gtatttaagg acatcgtgcc              1312 ccaagcccac ttgggatcga ttaaagcggc cgcgact                                       1349

<210> SEQ ID NO 33
<211> LENGTH: 403
<212> TYPE: PRT
<213> ORGANISM: Artificial Sequence
<220> FEATURE:
<223> OTHER INFORMATION: Porcine (Sus scrofa) TGF-beta1/N+5 FLAG Fusion
      Construct

<400> SEQUENCE: 33

Met Ala Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Asp Val Pro Pro Gly Pro Leu Pro Glu Ala Val Leu Ala Leu
65                  70                  75                  80

Tyr Asn Ser Thr Arg Asp Arg Val Ala Gly Glu Ser Val Glu Pro Glu
                85                  90                  95

Pro Glu Pro Glu Ala Asp Tyr Tyr Ala Lys Glu Val Thr Arg Val Leu
                100                 105                 110

Met Val Glu Ser Gly Asn Gln Ile Tyr Asp Lys Phe Lys Gly Thr Pro
            115                 120                 125

His Ser Leu Tyr Met Leu Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Ser
                180                 185                 190

Pro Glu Trp Leu Ser Phe Asp Val Thr Gly Val Val Arg Gln Trp Leu
            195                 200                 205

Thr Arg Arg Glu Ala Ile Glu Gly Phe Arg Leu Ser Ala His Ser Ser
        210                 215                 220

Ser Asp Ser Lys Asp Asn Thr Leu His Val Glu Ile Asn Gly Phe Asn
225                 230                 235                 240
```

-continued

```
Ser Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Asp Tyr Lys Asp Asp
            275                 280                 285

Asp Asp Lys Ala Leu Asp Thr Asn Tyr Cys Phe Ser Ser Thr Glu Lys
290                 295                 300

Asn Cys Cys Val Arg Gln Leu Tyr Ile Asp Phe Arg Lys Asp Leu Gly
305                 310                 315                 320

Trp Lys Trp Ile His Glu Pro Lys Gly Tyr His Ala Asn Phe Cys Leu
            325                 330                 335

Gly Pro Cys Pro Tyr Ile Trp Ser Leu Asp Thr Gln Tyr Ser Lys Val
            340                 345                 350

Leu Ala Leu Tyr Asn Gln His Asn Pro Gly Ala Ser Ala Ala Pro Cys
            355                 360                 365

Cys Val Pro Gln Ala Leu Glu Pro Leu Pro Ile Val Tyr Tyr Val Gly
    370                 375                 380

Arg Lys Pro Lys Val Glu Gln Leu Ser Asn Met Ile Val Arg Ser Cys
385                 390                 395                 400

Lys Cys Ser
```

<210> SEQ ID NO 34
<211> LENGTH: 1353
<212> TYPE: DNA
<213> ORGANISM: Artificial Sequence
<220> FEATURE:
<223> OTHER INFORMATION: Porcine (Sus scrofa) TGF-beta1/N+5 FLAG Fusion
      Construct
<220> FEATURE:
<221> NAME/KEY: 5'utr
<222> LOCATION: (1)..(14)
<223> OTHER INFORMATION: 5' untranslated region
<220> FEATURE:
<221> NAME/KEY: CDS
<222> LOCATION: (15)..(1226)
<223> OTHER INFORMATION: Protein coding sequence
<220> FEATURE:
<221> NAME/KEY: misc_feature
<222> LOCATION: (849)..(863)
<223> OTHER INFORMATION: Encodes amino acid residues 1-5 of TGF-beta1
<220> FEATURE:
<221> NAME/KEY: misc_feature
<222> LOCATION: (849)..(1226)
<223> OTHER INFORMATION: Encodes mature fusion protein
<220> FEATURE:
<221> NAME/KEY: misc_feature
<222> LOCATION: (864)..(887)
<223> OTHER INFORMATION: Encodes FLAG epitope tage
<220> FEATURE:
<221> NAME/KEY: 3'UTR
<222> LOCATION: (1227)..(1353)
<223> OTHER INFORMATION: 3' untranslated region

<400> SEQUENCE: 34

```
gatctggtac cgag atg gcg cct tcg ggg ctg cgg ctc ttg ccg ctg ctg         50
              Met Ala Pro Ser Gly Leu Arg Leu Leu Pro Leu Leu
                1               5                   10 ctg ccg ctg ctg tgg ctg cta gtg ctg acg cct ggc cgg ccg gcc gcc         98
Leu Pro Leu Leu Trp Leu Leu Val Leu Thr Pro Gly Arg Pro Ala Ala
        15                  20                  25 gga ctg tcc acc tgc aag acc atc gac atg gag ctg gtg aag cgg aag        146
Gly Leu Ser Thr Cys Lys Thr Ile Asp Met Glu Leu Val Lys Arg Lys
    30                  35                  40
```

-continued

| | | |
|---|---|---|
| cgc atc gag gcc att cgc ggc cag att ctg tcc aag ctt cgg ctt gcc<br>Arg Ile Glu Ala Ile Arg Gly Gln Ile Leu Ser Lys Leu Arg Leu Ala<br>45                           50                     55                 60 | | 194 |
| agc ccc ccg agc cag ggg gac gtg ccg ccc ggc ccg ctg cct gag gca<br>Ser Pro Pro Ser Gln Gly Asp Val Pro Pro Gly Pro Leu Pro Glu Ala<br>                  65                     70                     75 | | 242 |
| gta ctg gct ctt tac aac agt acc cgc gac cgg gta gcc ggg gaa agt<br>Val Leu Ala Leu Tyr Asn Ser Thr Arg Asp Arg Val Ala Gly Glu Ser<br>        80                     85                     90 | | 290 |
| gtc gaa ccg gag ccc gag cca gag gcg gac tac tac gcc aag gag gtc<br>Val Glu Pro Glu Pro Glu Pro Glu Ala Asp Tyr Tyr Ala Lys Glu Val<br>       95                     100                  105 | | 338 |
| acc cgc gtg cta atg gtg gaa agc ggc aac caa atc tat gat aaa ttc<br>Thr Arg Val Leu Met Val Glu Ser Gly Asn Gln Ile Tyr Asp Lys Phe<br>110                       115                  120 | | 386 |
| aag ggc acc ccc cac agc tta tat atg ctg ttc aac acg tcg gag ctc<br>Lys Gly Thr Pro His Ser Leu Tyr Met Leu Phe Asn Thr Ser Glu Leu<br>125                       130                  135                 140 | | 434 |
| cgg gaa gcg gtg ccg gaa cct gta ttg ctc tct cgg gca gag ctg cgc<br>Arg Glu Ala Val Pro Glu Pro Val Leu Leu Ser Arg Ala Glu Leu Arg<br>                   145                  150                 155 | | 482 |
| ctg ctg agg ctc aag tta aaa gtg gag cag cac gtg gag cta tac cag<br>Leu Leu Arg Leu Lys Leu Lys Val Glu Gln His Val Glu Leu Tyr Gln<br>                160                    165                170 | | 530 |
| aaa tac agc aat gat tcc tgg cgc tac ctc agc aac cgg ctg ctg gcc<br>Lys Tyr Ser Asn Asp Ser Trp Arg Tyr Leu Ser Asn Arg Leu Leu Ala<br>175                       180                  185 | | 578 |
| ccc agt gac tca ccg gag tgg ctg tcc ttt gat gtc acc gga gtt gtg<br>Pro Ser Asp Ser Pro Glu Trp Leu Ser Phe Asp Val Thr Gly Val Val<br>         190                     195                  200 | | 626 |
| cgg cag tgg ctg acc cgc aga gag gct ata gag ggt ttt cgc ctc agt<br>Arg Gln Trp Leu Thr Arg Arg Glu Ala Ile Glu Gly Phe Arg Leu Ser<br>205                       210                  215                 220 | | 674 |
| gcc cac tgt tcc tgt gac agc aaa gat aac aca ctc cac gtg gaa att<br>Ala His Cys Ser Cys Asp Ser Lys Asp Asn Thr Leu His Val Glu Ile<br>                   225                  230                 235 | | 722 |
| aac ggg ttc aat tct ggc cgc cgg ggt gac ctg gcc acc att cac ggc<br>Asn Gly Phe Asn Ser Gly Arg Arg Gly Asp Leu Ala Thr Ile His Gly<br>                   240                  245                 250 | | 770 |
| atg aac cgg ccc ttc ctg ctc ctc atg gcc acc ccg ctg gag agg gcc<br>Met Asn Arg Pro Phe Leu Leu Leu Met Ala Thr Pro Leu Glu Arg Ala<br>             255                  260                 265 | | 818 |
| cag cac ctg cac agc tcc cgg cac cgc cga gcc ctg gat acc aac gac<br>Gln His Leu His Ser Ser Arg His Arg Arg Ala Leu Asp Thr Asn Asp<br>270                       275                  280 | | 866 |
| tac aag gat gac gac gac aag gcc ctg gat acc aac tac tgc ttc agc<br>Tyr Lys Asp Asp Asp Asp Lys Ala Leu Asp Thr Asn Tyr Cys Phe Ser<br>285                       290                  295                 300 | | 914 |
| tcc acg gag aag aac tgc tgc gtg cgg cag ctc tac att gac ttc cgg<br>Ser Thr Glu Lys Asn Cys Cys Val Arg Gln Leu Tyr Ile Asp Phe Arg<br>                   305                  310                 315 | | 962 |
| aag gac ctg ggc tgg aag tgg att cat gaa ccc aag ggc tac cat gcc<br>Lys Asp Leu Gly Trp Lys Trp Ile His Glu Pro Lys Gly Tyr His Ala<br>                   320                  325                330 | | 1010 |
| aat ttc tgc ctg ggg ccc tgt ccc tac atc tgg agc cta gac act cag<br>Asn Phe Cys Leu Gly Pro Cys Pro Tyr Ile Trp Ser Leu Asp Thr Gln<br>335                       340                  345 | | 1058 |
| tac agc aag gtc ctg gct ctg tac aac cag cac aac ccg ggc gcg tcg<br>Tyr Ser Lys Val Leu Ala Leu Tyr Asn Gln His Asn Pro Gly Ala Ser<br>350                       355                  360 | | 1106 |

```
gcg gcg ccg tgc tgc gtg ccg cag gcg ctg gag cca ctg ccc atc gtg      1154
Ala Ala Pro Cys Cys Val Pro Gln Ala Leu Glu Pro Leu Pro Ile Val
365             370                 375                 380 tac tac gtg ggc cgc aag ccc aag gtg gag cag ctg tcc aac atg atc      1202
Tyr Tyr Val Gly Arg Lys Pro Lys Val Glu Gln Leu Ser Asn Met Ile
                385                 390                 395 gtg cgt tcc tgc aag tgc agc tga ggccccgccc cgcccacagc ccgcccacc      1256
Val Arg Ser Cys Lys Cys Ser
                400 cggcaggccc ggccccaccc ccgcccgcct caccggggct gtatttaagg acatcgtgcc    1316 ccaagcccac ttgggatcga ttaaagcggc cgcgact                             1353

<210> SEQ ID NO 35
<211> LENGTH: 403
<212> TYPE: PRT
<213> ORGANISM: Artificial Sequence
<220> FEATURE:
<223> OTHER INFORMATION: Porcine (Sus scrofa) TGF-beta1/N+5 FLAG Fusion
      Construct

<400> SEQUENCE: 35

Met Ala Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Asp Val Pro Pro Gly Pro Leu Pro Glu Ala Val Leu Ala Leu
65                  70                  75                  80

Tyr Asn Ser Thr Arg Asp Arg Val Ala Gly Glu Ser Val Glu Pro Glu
                85                  90                  95

Pro Glu Pro Glu Ala Asp Tyr Tyr Ala Lys Glu Val Thr Arg Val Leu
            100                 105                 110

Met Val Glu Ser Gly Asn Gln Ile Tyr Asp Lys Phe Lys Gly Thr Pro
        115                 120                 125

His Ser Leu Tyr Met Leu Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Thr Arg Arg Glu Ala Ile Glu Gly Phe Arg Leu Ser Ala His Cys Ser
    210                 215                 220

Cys Asp Ser Lys Asp Asn Thr Leu His Val Glu Ile Asn Gly Phe Asn
225                 230                 235                 240

Ser Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu His
            260                 265                 270
```

-continued

```
Ser Ser Arg His Arg Arg Ala Leu Asp Thr Asn Asp Tyr Lys Asp Asp
        275                 280                 285

Asp Asp Lys Ala Leu Asp Thr Asn Tyr Cys Phe Ser Ser Thr Glu Lys
        290                 295                 300

Asn Cys Cys Val Arg Gln Leu Tyr Ile Asp Phe Arg Lys Asp Leu Gly
305                 310                 315                 320

Trp Lys Trp Ile His Glu Pro Lys Gly Tyr His Ala Asn Phe Cys Leu
                325                 330                 335

Gly Pro Cys Pro Tyr Ile Trp Ser Leu Asp Thr Gln Tyr Ser Lys Val
                340                 345                 350

Leu Ala Leu Tyr Asn Gln His Asn Pro Gly Ala Ser Ala Ala Pro Cys
        355                 360                 365

Cys Val Pro Gln Ala Leu Glu Pro Leu Pro Ile Val Tyr Tyr Val Gly
    370                 375                 380

Arg Lys Pro Lys Val Glu Gln Leu Ser Asn Met Ile Val Arg Ser Cys
385                 390                 395                 400

Lys Cys Ser
```

<210> SEQ ID NO 36
<211> LENGTH: 1361
<212> TYPE: DNA
<213> ORGANISM: Artificial Sequence
<220> FEATURE:
<223> OTHER INFORMATION: Porcine (Sus scrofa) TGF-beta1/N+5 HA Fusion
      Construct
<220> FEATURE:
<221> NAME/KEY: 5'UTR
<222> LOCATION: (1)..(10)
<223> OTHER INFORMATION: 5' untranslated region
<220> FEATURE:
<221> NAME/KEY: CDS
<222> LOCATION: (11)..(1234)
<223> OTHER INFORMATION: Protein coding sequence
<220> FEATURE:
<221> NAME/KEY: misc_feature
<222> LOCATION: (845)..(859)
<223> OTHER INFORMATION: Encodes amino acid residues 1-5 of TGF-beta1
<220> FEATURE:
<221> NAME/KEY: misc_feature
<222> LOCATION: (845)..(1234)
<223> OTHER INFORMATION: Encodes mature fusion protein
<220> FEATURE:
<221> NAME/KEY: misc_feature
<222> LOCATION: (860)..(895)
<223> OTHER INFORMATION: Encodes HA epitope tag
<220> FEATURE:
<221> NAME/KEY: 3'UTR
<222> LOCATION: (1235)..(1361)
<223> OTHER INFORMATION: 3' untranslated region

<400> SEQUENCE: 36
tggtaccgag atg gcg cct tcg ggg ctg cgg ctc ttg ccg ctg ctg ctg        49
           Met Ala Pro Ser Gly Leu Arg Leu Leu Pro Leu Leu Leu
           1               5                   10 ccg ctg ctg tgg ctg cta gtg ctg acg cct ggc cgg ccg gcc gcc gga       97
Pro Leu Leu Trp Leu Leu Val Leu Thr Pro Gly Arg Pro Ala Ala Gly
    15                  20                  25 ctg tcc acc tgc aag acc atc gac atg gag ctg gtg aag cgg aag cgc      145
Leu Ser Thr Cys Lys Thr Ile Asp Met Glu Leu Val Lys Arg Lys Arg
30                  35                  40                  45 atc gag gcc att cgc ggc cag att ctg tcc aag ctt cgg ctt gcc agc      193
Ile Glu Ala Ile Arg Gly Gln Ile Leu Ser Lys Leu Arg Leu Ala Ser
                50                  55                  60 ccc ccg agc cag ggg gac gtg ccg ccc ggc ccg ctg cct gag gca gta      241
Pro Pro Ser Gln Gly Asp Val Pro Pro Gly Pro Leu Pro Glu Ala Val -continued

```
                65                    70                    75
ctg gct ctt tac aac agt acc cgc gac cgg gta gcc ggg gaa agt gtc      289
Leu Ala Leu Tyr Asn Ser Thr Arg Asp Arg Val Ala Gly Glu Ser Val
            80                    85                    90 gaa ccg gag ccc gag cca gag gcg gac tac tac gcc aag gag gtc acc      337
Glu Pro Glu Pro Glu Pro Glu Ala Asp Tyr Tyr Ala Lys Glu Val Thr
        95                   100                   105 cgc gtg cta atg gtg gaa agc ggc aac caa atc tat gat aaa ttc aag      385
Arg Val Leu Met Val Glu Ser Gly Asn Gln Ile Tyr Asp Lys Phe Lys
110                 115                   120                   125 ggc acc ccc cac agc tta tat atg ctg ttc aac acg tcg gag ctc cgg      433
Gly Thr Pro His Ser Leu Tyr Met Leu Phe Asn Thr Ser Glu Leu Arg
                130                   135                   140 gaa gcg gtg ccg gaa cct gta ttg ctc tct cgg gca gag ctg cgc ctg      481
Glu Ala Val Pro Glu Pro Val Leu Leu Ser Arg Ala Glu Leu Arg Leu
            145                   150                   155 ctg agg ctc aag tta aaa gtg gag cag cac gtg gag cta tac cag aaa      529
Leu Arg Leu Lys Leu Lys Val Glu Gln His Val Glu Leu Tyr Gln Lys
        160                   165                   170 tac agc aat gat tcc tgg cgc tac ctc agc aac cgg ctg ctg gcc ccc      577
Tyr Ser Asn Asp Ser Trp Arg Tyr Leu Ser Asn Arg Leu Leu Ala Pro
175                 180                   185 agt gac tca ccg gag tgg ctg tcc ttt gat gtc acc gga gtt gtg cgg      625
Ser Asp Ser Pro Glu Trp Leu Ser Phe Asp Val Thr Gly Val Val Arg
190                   195                   200                   205 cag tgg ctg acc cgc aga gag gct ata gag ggt ttt cgc ctc agt gcc      673
Gln Trp Leu Thr Arg Arg Glu Ala Ile Glu Gly Phe Arg Leu Ser Ala
                210                   215                   220 cac tct tcc tct gac agc aaa gat aac aca ctc cac gtg gaa att aac      721
His Ser Ser Ser Asp Ser Lys Asp Asn Thr Leu His Val Glu Ile Asn
            225                   230                   235 ggg ttc aat tct ggc cgc cgg ggt gac ctg gcc acc att cac ggc atg      769
Gly Phe Asn Ser Gly Arg Arg Gly Asp Leu Ala Thr Ile His Gly Met
        240                   245                   250 aac cgg ccc ttc ctg ctc ctc atg gcc acc ccg ctg gag agg gcc cag      817
Asn Arg Pro Phe Leu Leu Leu Met Ala Thr Pro Leu Glu Arg Ala Gln
255                 260                   265 cac ctg cac agc tcc cgg cac cgc cga gcc ctg gat acc aac agc tac      865
His Leu His Ser Ser Arg His Arg Arg Ala Leu Asp Thr Asn Ser Tyr
270                   275                   280                   285 cca tac gac gtg cca gac tac gca tct ctg gcc ctg gat acc aac tac      913
Pro Tyr Asp Val Pro Asp Tyr Ala Ser Leu Ala Leu Asp Thr Asn Tyr
                290                   295                   300 tgc ttc agc tcc acg gag aag aac tgc tgc gtg cgg cag ctc tac att      961
Cys Phe Ser Ser Thr Glu Lys Asn Cys Cys Val Arg Gln Leu Tyr Ile
            305                   310                   315 gac ttc cgg aag gac ctg ggc tgg aag tgg att cat gaa ccc aag ggc     1009
Asp Phe Arg Lys Asp Leu Gly Trp Lys Trp Ile His Glu Pro Lys Gly
        320                   325                   330 tac cat gcc aat ttc tgc ctg ggg ccc tgt ccc tac atc tgg agc cta     1057
Tyr His Ala Asn Phe Cys Leu Gly Pro Cys Pro Tyr Ile Trp Ser Leu
335                 340                   345 gac act cag tac agc aag gtc ctg gct ctg tac aac cag cac aac ccg     1105
Asp Thr Gln Tyr Ser Lys Val Leu Ala Leu Tyr Asn Gln His Asn Pro
350                   355                   360                   365 ggc gcg tcg gcg gcg ccg tgc tgc gtg ccg cag gcg ctg gag cca ctg     1153
Gly Ala Ser Ala Ala Pro Cys Cys Val Pro Gln Ala Leu Glu Pro Leu
                370                   375                   380 ccc atc gtg tac tac gtg ggc cgc aag ccc aag gtg gag cag ctg tcc     1201
```

-continued

```
Pro Ile Val Tyr Tyr Val Gly Arg Lys Pro Lys Val Glu Gln Leu Ser
            385                 390                 395 aac atg atc gtg cgt tcc tgc aag tgc agc tga ggccccgccc cgcccacagc   1254
Asn Met Ile Val Arg Ser Cys Lys Cys Ser
        400                 405 cccgcccacc cggcaggccc ggccccaccc ccgcccgcct caccggggct gtatttaagg   1314
acatcgtgcc ccaagcccac ttgggatcga ttaaagcggc cgcgact                 1361

<210> SEQ ID NO 37
<211> LENGTH: 407
<212> TYPE: PRT
<213> ORGANISM: Artificial Sequence
<220> FEATURE:
<223> OTHER INFORMATION: Porcine (Sus scrofa) TGF-beta1/N+5 HA Fusion
      Construct

<400> SEQUENCE: 37

Met Ala Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Asp Val Pro Pro Gly Pro Leu Pro Glu Ala Val Leu Ala Leu
65                  70                  75                  80

Tyr Asn Ser Thr Arg Asp Arg Val Ala Gly Glu Ser Val Glu Pro Glu
                85                  90                  95

Pro Glu Pro Glu Ala Asp Tyr Tyr Ala Lys Glu Val Thr Arg Val Leu
            100                 105                 110

Met Val Glu Ser Gly Asn Gln Ile Tyr Asp Lys Phe Lys Gly Thr Pro
        115                 120                 125

His Ser Leu Tyr Met Leu Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Thr Arg Arg Glu Ala Ile Glu Gly Phe Arg Leu Ser Ala His Ser Ser
    210                 215                 220

Ser Asp Ser Lys Asp Asn Thr Leu His Val Glu Ile Asn Gly Phe Asn
225                 230                 235                 240

Ser Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Ser Tyr Pro Tyr Asp
        275                 280                 285

Val Pro Asp Tyr Ala Ser Leu Ala Leu Asp Thr Asn Tyr Cys Phe Ser
    290                 295                 300
```

-continued

```
Ser Thr Glu Lys Asn Cys Cys Val Arg Gln Leu Tyr Ile Asp Phe Arg
305                 310                 315                 320

Lys Asp Leu Gly Trp Lys Trp Ile His Glu Pro Lys Gly Tyr His Ala
                325                 330                 335

Asn Phe Cys Leu Gly Pro Cys Pro Tyr Ile Trp Ser Leu Asp Thr Gln
            340                 345                 350

Tyr Ser Lys Val Leu Ala Leu Tyr Asn Gln His Asn Pro Gly Ala Ser
        355                 360                 365

Ala Ala Pro Cys Cys Val Pro Gln Ala Leu Glu Pro Leu Pro Ile Val
    370                 375                 380

Tyr Tyr Val Gly Arg Lys Pro Lys Val Glu Gln Leu Ser Asn Met Ile
385                 390                 395                 400

Val Arg Ser Cys Lys Cys Ser
                405

<210> SEQ ID NO 38
<211> LENGTH: 1361
<212> TYPE: DNA
<213> ORGANISM: Artificial Sequence
<220> FEATURE:
<223> OTHER INFORMATION: Porcine (Sus scrofa) TGF-beta1/N+5 HA Fusion
      Construct
<220> FEATURE:
<221> NAME/KEY: 5'UTR
<222> LOCATION: (1)..(10)
<223> OTHER INFORMATION: 5' untranslated region
<220> FEATURE:
<221> NAME/KEY: CDS
<222> LOCATION: (11)..(1234)
<223> OTHER INFORMATION: Protein coding sequence
<220> FEATURE:
<221> NAME/KEY: misc_feature
<222> LOCATION: (845)..(859)
<223> OTHER INFORMATION: Encodes amino acid residues 1-5 of TGF-beta1
<220> FEATURE:
<221> NAME/KEY: misc_feature
<222> LOCATION: (845)..(1234)
<223> OTHER INFORMATION: Encodes mature fusion protein
<220> FEATURE:
<221> NAME/KEY: misc_feature
<222> LOCATION: (860)..(895)
<223> OTHER INFORMATION: Encodes HA epitope tag
<220> FEATURE:
<221> NAME/KEY: 3'UTR
<222> LOCATION: (1235)..(1361)
<223> OTHER INFORMATION: 3' untranslated region

<400> SEQUENCE: 38
tggtaccgag atg gcg cct tcg ggg ctg cgg ctc ttg ccg ctg ctg ctg        49
           Met Ala Pro Ser Gly Leu Arg Leu Leu Pro Leu Leu Leu
           1               5                   10 ccg ctg ctg tgg ctg cta gtg ctg acg cct ggc cgg ccg gcc gcc gga       97
Pro Leu Leu Trp Leu Leu Val Leu Thr Pro Gly Arg Pro Ala Ala Gly
    15                  20                  25 ctg tcc acc tgc aag acc atc gac atg gag ctg gtg aag cgg aag cgc      145
Leu Ser Thr Cys Lys Thr Ile Asp Met Glu Leu Val Lys Arg Lys Arg
30                  35                  40                  45 atc gag gcc att cgc ggc cag att ctg tcc aag ctt cgg ctt gcc agc      193
Ile Glu Ala Ile Arg Gly Gln Ile Leu Ser Lys Leu Arg Leu Ala Ser
                50                  55                  60 ccc ccg agc cag ggg gac gtg ccg ccc ggc ccg ctg cct gag gca gta      241
Pro Pro Ser Gln Gly Asp Val Pro Pro Gly Pro Leu Pro Glu Ala Val
            65                  70                  75 ctg gct ctt tac aac agt acc cgc gac cgg gta gcc ggg gaa agt gtc      289
Leu Ala Leu Tyr Asn Ser Thr Arg Asp Arg Val Ala Gly Glu Ser Val
        80                  85                  90
```

```
                                                    -continued gaa ccg gag ccc gag cca gag gcg gac tac tac gcc aag gag gtc acc         337
Glu Pro Glu Pro Glu Pro Glu Ala Asp Tyr Tyr Ala Lys Glu Val Thr
 95              100                 105 cgc gtg cta atg gtg gaa agc ggc aac caa atc tat gat aaa ttc aag         385
Arg Val Leu Met Val Glu Ser Gly Asn Gln Ile Tyr Asp Lys Phe Lys
110              115                 120                 125 ggc acc ccc cac agc tta tat atg ctg ttc aac acg tcg gag ctc cgg         433
Gly Thr Pro His Ser Leu Tyr Met Leu Phe Asn Thr Ser Glu Leu Arg
                 130                 135                 140 gaa gcg gtg ccg gaa cct gta ttg ctc tct cgg gca gag ctg cgc ctg         481
Glu Ala Val Pro Glu Pro Val Leu Leu Ser Arg Ala Glu Leu Arg Leu
             145                 150                 155 ctg agg ctc aag tta aaa gtg gag cag cac gtg gag cta tac cag aaa         529
Leu Arg Leu Lys Leu Lys Val Glu Gln His Val Glu Leu Tyr Gln Lys
         160                 165                 170 tac agc aat gat tcc tgg cgc tac ctc agc aac cgg ctg ctg gcc ccc         577
Tyr Ser Asn Asp Ser Trp Arg Tyr Leu Ser Asn Arg Leu Leu Ala Pro
     175                 180                 185 agt gac tca ccg gag tgg ctg tcc ttt gat gtc acc gga gtt gtg cgg         625
Ser Asp Ser Pro Glu Trp Leu Ser Phe Asp Val Thr Gly Val Val Arg
190                 195                 200                 205 cag tgg ctg acc cgc aga gag gct ata gag ggt ttt cgc ctc agt gcc         673
Gln Trp Leu Thr Arg Arg Glu Ala Ile Glu Gly Phe Arg Leu Ser Ala
                 210                 215                 220 cac tgt tcc tgt gac agc aaa gat aac aca ctc cac gtg gaa att aac         721
His Cys Ser Cys Asp Ser Lys Asp Asn Thr Leu His Val Glu Ile Asn
             225                 230                 235 ggg ttc aat tct ggc cgc cgg ggt gac ctg gcc acc att cac ggc atg         769
Gly Phe Asn Ser Gly Arg Arg Gly Asp Leu Ala Thr Ile His Gly Met
         240                 245                 250 aac cgg ccc ttc ctg ctc ctc atg gcc acc ccg ctg gag agg gcc cag         817
Asn Arg Pro Phe Leu Leu Leu Met Ala Thr Pro Leu Glu Arg Ala Gln
     255                 260                 265 cac ctg cac agc tcc cgg cac cgc cga gcc ctg gat acc aac agc tac         865
His Leu His Ser Ser Arg His Arg Arg Ala Leu Asp Thr Asn Ser Tyr
270                 275                 280                 285 cca tac gac gtg cca gac tac gca tct ctg gcc ctg gat acc aac tac         913
Pro Tyr Asp Val Pro Asp Tyr Ala Ser Leu Ala Leu Asp Thr Asn Tyr
                 290                 295                 300 tgc ttc agc tcc acg gag aag aac tgc tgc gtg cgg cag ctc tac att         961
Cys Phe Ser Ser Thr Glu Lys Asn Cys Cys Val Arg Gln Leu Tyr Ile
             305                 310                 315 gac ttc cgg aag gac ctg ggc tgg aag tgg att cat gaa ccc aag ggc        1009
Asp Phe Arg Lys Asp Leu Gly Trp Lys Trp Ile His Glu Pro Lys Gly
         320                 325                 330 tac cat gcc aat ttc tgc ctg ggg ccc tgt ccc tac atc tgg agc cta        1057
Tyr His Ala Asn Phe Cys Leu Gly Pro Cys Pro Tyr Ile Trp Ser Leu
     335                 340                 345 gac act cag tac agc aag gtc ctg gct ctg tac aac cag cac aac ccg        1105
Asp Thr Gln Tyr Ser Lys Val Leu Ala Leu Tyr Asn Gln His Asn Pro
350                 355                 360                 365 ggc gcg tcg gcg gcg ccg tgc tgc gtg ccg cag gcg ctg gag cca ctg        1153
Gly Ala Ser Ala Ala Pro Cys Cys Val Pro Gln Ala Leu Glu Pro Leu
                 370                 375                 380 ccc atc gtg tac tac gtg ggc cgc aag ccc aag gtg gag cag ctg tcc        1201
Pro Ile Val Tyr Tyr Val Gly Arg Lys Pro Lys Val Glu Gln Leu Ser
             385                 390                 395 aac atg atc gtg cgt tcc tgc aag tgc agc tga ggccccgccc cgcccacagc     1254
Asn Met Ile Val Arg Ser Cys Lys Cys Ser
```

```
                400             405
cccgcccacc cggcaggccc ggccccaccc ccgcccgcct caccggggct gtatttaagg    1314
acatcgtgcc ccaagcccac ttgggatcga ttaaagcggc cgcgact                  1361
```

<210> SEQ ID NO 39
<211> LENGTH: 407
<212> TYPE: PRT
<213> ORGANISM: Artificial Sequence
<220> FEATURE:
<223> OTHER INFORMATION: Porcine (Sus scrofa) TGF-beta1/N+5 HA Fusion
      Construct

<400> SEQUENCE: 39

```
Met Ala Pro Ser Gly Leu Arg Leu Leu Pro Leu Leu Leu Pro Leu Leu
1

```
-continued

Asn Phe Cys Leu Gly Pro Cys Pro Tyr Ile Trp Ser Leu Asp Thr Gln
            340                 345                 350

Tyr Ser Lys Val Leu Ala Leu Tyr Asn Gln His Asn Pro Gly Ala Ser
        355                 360                 365

Ala Ala Pro Cys Cys Val Pro Gln Ala Leu Glu Pro Leu Pro Ile Val
    370                 375                 380

Tyr Tyr Val Gly Arg Lys Pro Lys Val Glu Gln Leu Ser Asn Met Ile
385                 390                 395                 400

Val Arg Ser Cys Lys Cys Ser
                405
```

FUNCTIONALIZED TGF-β FUSION PROTEINS

CROSS REFERENCE TO RELATED APPLICATION

This application claims the benefit of U.S. Provisional Application No. 60/242,292, filed Oct. 20, 2000. The provisional application is incorporated herein in its entirety.

FIELD

The disclosure is in the field of protein labeling and detection. More specifically, the disclosure relates to the use of molecular tags to identify and track recombinant molecules, such as small proteins, in a subject.

BACKGROUND

TGF-β Protein Family

Transforming growth factor-β1 (TGF-β1) is a growth factor and immunomodulatory cytokine that is secreted from cells and acts through specific binding interactions with a collection of different cell-surface localized receptors. TGF-β1 is the prototype for a large family of secreted polypeptides that includes the three mammalian TGF-β isoforms (TGF-β1, TGF-β2, and TGF-β3), bone morphogenesis proteins (BMPs), activins, and Müllerian inhibitory substance (MIS). More distantly related members of this protein family include murine nodal gene products, Drosophila decapentaplegic complex gene products, and Vg1 from Xenopus.

In general, TGF-β family proteins are homodimers, wherein each functional protein complex includes two identical, associated monomer subunits. The crystal structure of the TGF-β1 homodimer is known (Hinck el al., *Biochem.*, 35:8517–8534, 1996; Qian et al., *J. Biol. Chem.*, 271:30656–30662, 1996). TGF-β is a very compact protein, having four intramolecular disulfide bridges within each subunit, as well as one intermolecular disulfide bridge.

Each monomer of the protein is synthesized as a large (~55 kDa) precursor molecule with a long (about 278 residue) N-terminal pro-region and a much shorter (112 residue, 12.5 kDa) C-terminal active domain (the mature region). During the maturation process, two precursor molecules associate with each other; the pro-region is important for proper folding of and proper association between the two active domain monomers. The pro-region of each monomer is proteolytically cleaved from the associated active domain; in most instances however, the pro-region remains associated with the mature TGF-β fragment. The severed pro-region is referred to as the "latency-associated peptide" (LAP). LAP is responsible for blocking the correctly folded TGF-β homodimer so that it does not interact with its receptor. For an excellent discussion of TGF-β synthesis, see Khalil, *Micro. Infect.*, 1:1255–1263, 1999.

TGF-βs and their receptors are expressed in essentially all tissues, and have been found to be important in many cellular processes. These include cell growth and differentiation, immunosupression, inflammation, and the expression of extracellular matrix proteins. By way of example, in animal models TGF-β has been shown to attenuate the symptoms associated with various diseases and disorders, including rheumatoid arthritis, multiple sclerosis, wound healing, bronchial asthma, and inflammatory bowel disease, and has been used in the clinical setting to enhance wound healing.

TGF-β1 was the first identified member of the TGF-β family, and has been intensely studied for over 20 years. There are some TGF-β1 antibodies available, but their usefulness in a clinical setting is limited at least in part because they often display some degree of cross-reactivity to other TGF-β family proteins (see, e.g., U.S. Pat. No. 5,571, 714). In most experiments, TGF-β is iodinated with $^{125}$I to enable researchers to track the protein. Radioactive iodination is an expensive and hazardous process, and it usually would be inappropriate to use $^{125}$I labeled proteins for in vivo experimentation, for instance in clinical trials.

The ability to track the distribution of any exogenously administered, recombinant forms of TGF-β family proteins has been restricted by the inability to distinguish between the endogenous forms of the protein produced in treated cells or tissues. In addition, available antibodies to these proteins exhibit some degree of cross-reactivity with related family members.

There have been a few reports of TGF-β fusions in the literature, but the described molecules have been essentially biologically non-functional. In an effort to produce large quantities of easily purified TGF-β that retained activity, Nimni and co-workers expressed 6x His-tagged TGF-β fusion proteins in *Escherichia coli* (Tuan et al., *Conn. Tiss. Res.*, 34:1–9, 1996; Han et al., *Prot. Expr. Purif.*, 11:169–178, 1997). Serious difficulties were encountered in refolding the denatured fusion protein, and full biological activity was not retained using this system. In addition, the Nimni constructs cannot be used to express a tagged TGF-β in a mammalian host, since the constructs lack a part the TGF-β pro-protein (the LAP), which is essential for secretion and proper folding of the TGF-β protein. In an earlier effort, Wakefield et al. (*Growth Factors*, 5:243–253, 1991) reported attaching an endoplasmic reticulum retention signal to the C-terminus of full-length TGF-β1, in an attempt to maintain the protein in the cell (rather than secreting it to the extracellular matrix). This construct had no biological activity.

It is believed that all prior efforts to fuse a TGF-β family protein to a peptide or protein have resulted in biologically non-functional molecules. Therefore a need still exists for TGF-β family protein fusions that maintain substantial biological activity.

SUMMARY OF THE DISCLOSURE

This disclosure provides functionalized TGF-β fusion proteins that maintain substantial TGF-β biological activity. These fusion proteins are achieved by placing a functionalizing peptide between the pro- and active (mature) portions of a TGF-β protein, or at a relatively non-conserved site within the mature region of a TGF-β protein.

Encompassed herein are functional TGF-β family fusion proteins that contain a functionalizing peptide portion for detecting, quantifying or providing a specific additional function to the fusion protein and a mature TGF-β family protein, both as a monomer and in the form of a dimer (e.g., a homodimer). Also encompassed are nucleic acid molecules encoding such fusion proteins, and conservative substitutions of such molecules. This disclosure also provides methods for making and using the fusion proteins described, as well as kits.

The foregoing and other features and advantages will become more apparent from the following detailed description of several embodiments, which proceeds with reference to the accompanying figures.

BRIEF DESCRIPTION OF THE FIGURES

FIG. 4 shows the quantification and activity of functionalized TGF-β fusion proteins.

Figure 4A:
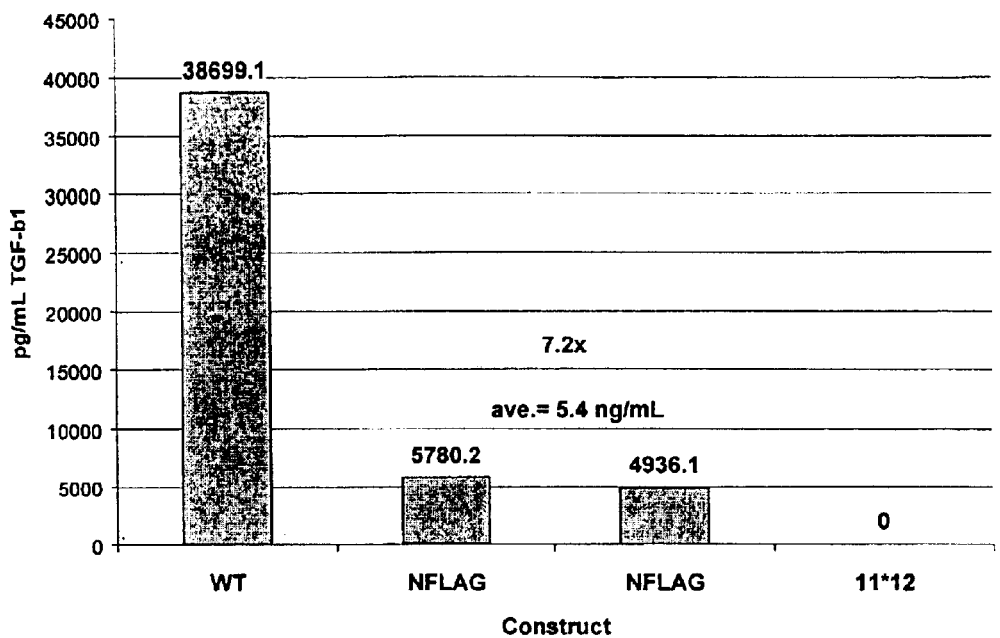
FIG. 4A is a graph showing the amount of the indicated TGF-β protein secreted into COS cell supernatants, as measured in media conditioned by COS cells using a standard ELISA kit specific for TGF-β1 (R&D Systems, Minneapolis, Minn.).
Figure 4B:
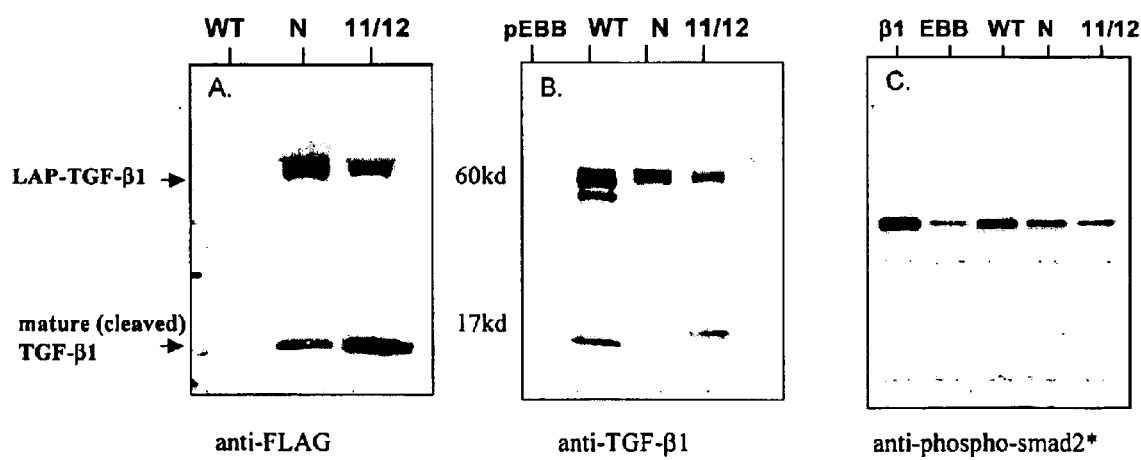
FIG. 4B is a series of Western blots; panels A (anti-TGF-β1 primary antibody) and B (anti-FLAG primary antibody) show the presence of the indicated TGF-β and TGF-β fusion proteins in mature and precursor forms.

Panel C of FIG. 4B shows a Western blot anti-phospho-smad2 primary antibody) demonstrating the induction of phosphorylation of Smad2 with media conditioned by COS cells expressing the indicated TGF-β proteins.

Figure 5:
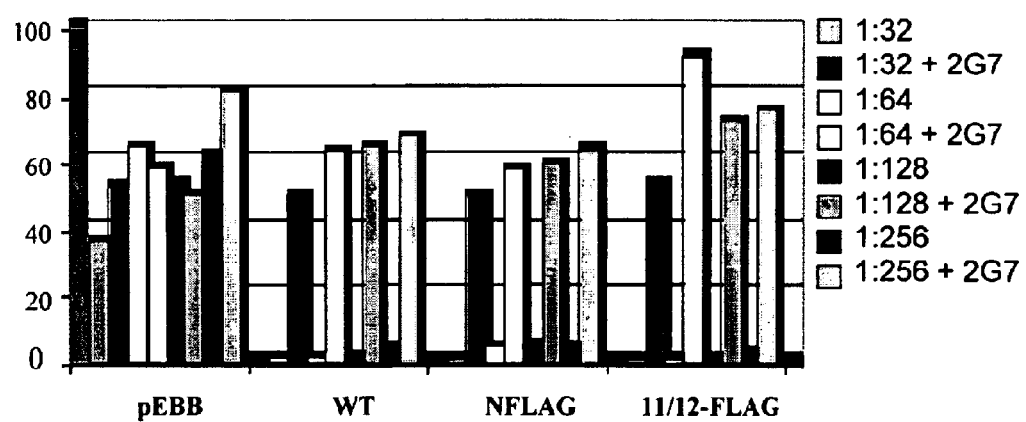

FIG. 5 is a bar graph quantifying and comparing the ability of the indicated dilutions of COS cell supernatants (pEBB, WT, NFLAG, 11/12 FLAG, differentiated by the indicated grey tones) to reversibly inhibit growth of CCL64 cells. Epitope-tagged TGF-β1 activity was present at dilutions of over 1:250, and could be neutralized with the anti-TGF-β blocking antibody, 2G7, thereby demonstrating that the inhibition was specific to the TGF-β protein or fusion protein.

FIG. 6A illustrates the design of TGF-β1 with an N-terminal FLAG tag (NFLAG-TGF-β1). The FLAG tag (boxed sequence) (SEQ ID NO: 7) was inserted immediately following the cleavage site (indicated by arrow). Amino acid sequence shown above nucleotide sequence in single letter code (corresponding to nucleic acid residues 817–954 of SEQ ID NO: 8).

FIG. 6B shows the expression levels of secreted TGF-β1 from transfected Cos1 cells (left panel). Blot probed with a rabbit polyclonal anti-human TGF-β1 antibody (Promega). For the NFLAG-TGF-β1 transfection, the ratio of cleaved, mature peptide (m) to unprocessed pro-peptide (p) is less than that for the untagged ligand (WT-TGF-β1). In the middle panel, a Western blot illustrates that anti-FLAG monoclonal antibody (clone M2) specifically detects the FLAG-tagged TGF-β1 but not the untagged ligand. Finally, the right panel of FIG. 6B illustrates that N-FLAG-TGF-β1 shows smad2 phosphorylation activity, based on the signal labeled "anti-P-smad2. rh-TGF-β1, recombinant human TGF-β1 at 2.5 ng/mL; levels of total smad 2 protein are unchanged.

FIG. 6C shows portions of the sequences of N+5FLAG-TGF-β1 (residues 815–914 of SEQ ID NO: 32) and N+5HA-TGF-β1 (residues 815–914 of SEQ ID NO: 36). Only the region in the vicinity of the cleavage site is shown, the numbering is different than in the attached sequence listing and refers to the position of the illustrated residues in the plasmid. The epitope tag sequences are boxed. Arrows indicate cleavage site that separates LAP from the mature TGF-β peptide. Note the localized concentration of basic amino acids in the region immediately upstream of the cleavage site (RHRR) residues 275–278 of both SEQ ID NOs: 33 and 37).

FIG. 6D shows the levels of secreted TGF-β1 detected by immunoblot analysis using a polyclonal anti- human TGF-β1 antibody (first four lanes) and the epitope tags (probed with anti-FLAG antibodies in the middle pair of lanes; proved with anti-HA antibodies right pair of lanes) for each of the indicated constructs. The ratio of mature to unprocessed ligand is essentially equivalent for each construct Antibodies against each of the epitope tags detect only the respective tagged ligand and not the un-tagged molecule.

Figure 7A:
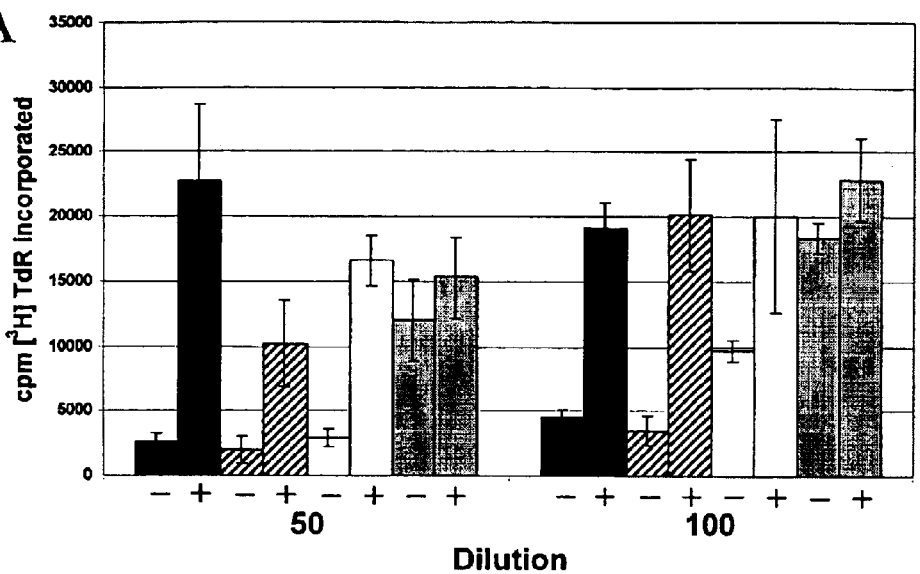

FIG. 7 illustrates activity of TGF-β fusion proteins. Mv1Lu cells were treated with conditioned medium from transfected cos-1 cells and inhibition of growth was assessed by incorporation of [$^3$H] thymidine. Results are shown in FIG. 7A. Solid bars, N+5FLAG-TGF-β1; first set of grey bars in each half of the graph, N+5HA-TGF-β1; open bars, WT-TGF-β1; second set of grey bars in each half of the graph, Empty vector. –and+indicate, respectively, absence or presence of TGF-β neutralizing antibody.

Figure 7B:
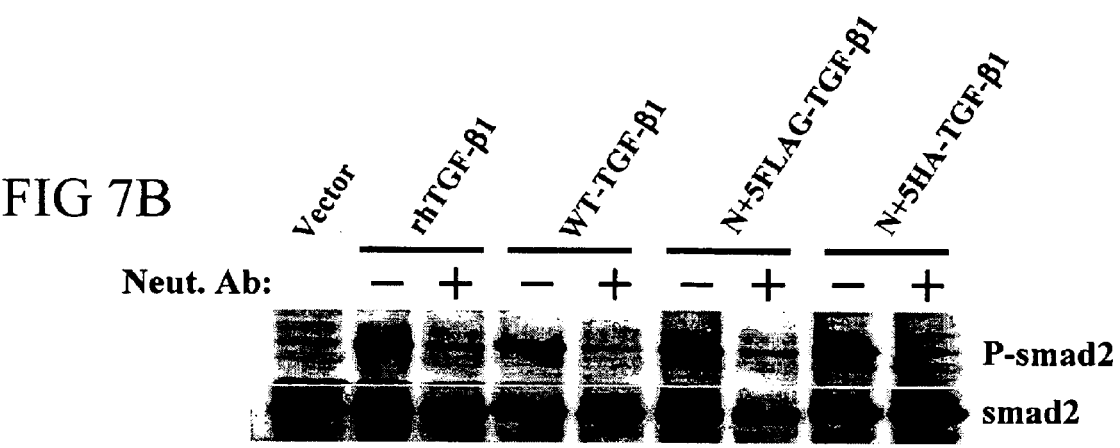

FIG. 7B is a pair of western blots illustrating levels of phospho-smad2 (upper panel) and smad2 (lower panel). Mv1Lu cells were treated with conditioned media (diluted 1:20) from Cos1 cells transfected with plasmids encoding untagged TGF-β1 (WT-TGF-β1), N+5FLAG-TGF-β1, N+5HA-TGF-β1 or empty vector. Rh-TGF-β1, recombinant human TGF-β1 (2.5 ng/mL). –and+indicate, respectively, the absence or presence of TGF-β neutralizing antibody. To generate the signals on the lower panel, the blot was stripped and re-probed using an antibody directed against smad 2.

Figure 7C:
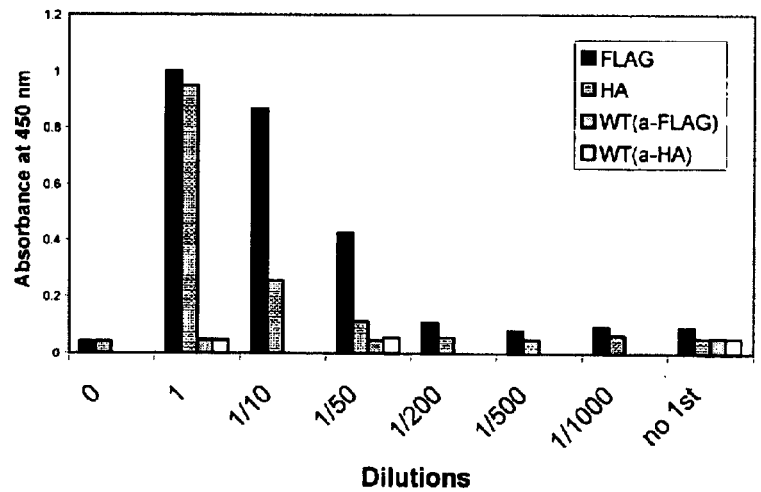

FIG. 7C illustrates the quantitative results of a sandwich ELISA to detect tagged TGF-β1 ligands in conditioned media. Solid bars, FLAG-tagged TGF-β1; stippled bars, HA-tagged TGF-β1; gray bars, untagged (WT) TGF-β1 in a FLAG-TGF-β1 SELISA; open bars, untagged (WT) TGF-β1 in a HA-TGF-β1 SELISA. "No 1 st," negative control where primary antibody (anti-FLAG or anti-HA) was omitted. Dilutions refer to dilutions of conditioned media.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 show the nucleic acid sequences of the flanking primers used to introduce the FLAG epitope tag into TGF-β1 using 2-step PCR mutagenesis technique.

SEQ ID NOs: 3 and 4 show the nucleic acid sequences of the primers used to construct the N-terminally tagged-TGF-β1 fusion (FLAG-β1).

SEQ ID NOs: 5 and 6 show the nucleic acid sequences of the primers used to insert the FLAG peptide tag between amino acids 11 and 12 of the mature TGF-β1.

SEQ ID NO: 7 shows the amino acid sequence of the FLAG peptide tag.

SEQ ID NO: 8 shows the nucleotide and amino acid sequences of the precursor of the NFLAG-FLAG-β1 fusion.

SEQ ID NO: 9 shows the amino acid sequence of the precursor of the N FLAG-β1 fusion. The cleavage site for maturation of the fusion is between amino acid residues 278 and 279, resulting in a mature NFLAG-TGF-β1 fusion of 120 amino acid residues.

SEQ ID NO: 10 shows the nucleic acid sequence of the mature NFLAG-β1 fusion.

SEQ ID NO: 11 shows the amino acid sequence of the mature NFLAG-β1 fusion.

SEQ ID NO: 12 shows the nucleotide and amino acid sequences of the precursor of the fusion with the FLAG peptide tag between amino acids 11 and 12 of the mature TGF-β1.

SEQ ID NO: 13 shows the amino acid sequence of the precursor of the fusion with the FLAG peptide tag between amino acids 11 and 12 of the mature TGF-β1. The cleavage site for maturation of the fusion is between amino acid residues 278 and 279, resulting in a mature 11/12FLAG-β1 fusion of 120 amino acid residues.

SEQ ID NO: 14 shows the nucleic acid sequence of the mature 11/12FLAG-β1 fusion.

SEQ ID NO: 15 shows the amino acid sequence of the mature 11/12FLAG-β1 fusion.

SEQ ID NO: 16 shows the nucleic acid and deduced amino acid sequence of the precursor murine N+5FLAG TGF-β1 (N+5FLAG-β1) fusion.

SEQ ID NO: 17 shows the amino acid sequence of the precursor murine N+5FLAG TGF-β1 (N+5FLAG-β1) fusion.

SEQ ID NOs: 18 and 19 show forward and reverse primers (respectively) used in construction of the N+5FLAG TGF-β1 (N+5FLAG-β1) fusion.

SEQ ID NO: 20 shows the nucleic acid and deduced amino acid sequence of the precursor N+5HA-TGF-β1 (N+5HA-β1) construct.

SEQ ID NO: 21 shows the amino acid sequence of the precursor N+5HA-TGF-β1 (N+5HA-β1) fusion.

SEQ ID NOs: 22 and 23 show forward and reverse primers (respectively) used in construction of the N+5HA-TGF-β1 (N+5HA-β1) fusion.

SEQ ID NO: 24 shows the nucleic acid and deduced protein sequence of the precursor murine N+5FLAG TGF-β2 (MN5FLAGb2) fusion.

SEQ ID NO: 25 shows the amino acid sequence of the precursor N+5FLAG-TGF-β2 (MN5FLAGb2) fusion.

SEQ ID NO: 26 shows the nucleic acid and deduced protein sequence of the precursor murine N+5HA TGF-β2 (MN5HAb2) fusion.

SEQ ID NO: 27 shows the amino acid sequence of the precursor N+5HA-TGF-β2 (MN5HAb2) fusion.

SEQ ID NO: 28 shows the nucleic acid and deduced protein sequence of the precursor murine N+5FLAG TGF-β3 (MN5FLAGb3) fusion.

SEQ ID NO: 29 shows the amino acid sequence of the precursor N+5FLAG-TGF-β3 (MN5FLAGb3) fusion.

SEQ ID NO: 30 shows the nucleic acid and deduced protein sequence of the precursor murine N+5HA TGF-β3 (MN5HAb3) fusion.

SEQ ID NO: 31 shows the amino acid sequence of the precursor N+5HA-TGF-β3 (MN5HAb3) fusion.

SEQ ID NO: 32 shows the nucleic acid and deduced protein sequence of the precursor porcine active N+5FLAG TGF-β1 (actN5FLAGb1) fusion.

SEQ ID NO: 33 shows the amino acid sequence of the precursor porcine active N+5FLAG-TGF-β1 (actN5FLAGb1) fusion.

SEQ ID NO: 34 shows the nucleic acid and deduced protein sequence of the precursor porcine latent N+5FLAG TGF-β1 (latN5FLAGb1) fusion.

SEQ ID NO: 35 shows the amino acid sequence of the precursor porcine latent N+5FLAG-TGF-β1 (latN5FLAGb1) fusion.

SEQ ID NO: 36 shows the nucleic acid and deduced protein sequence of the precursor porcine active N+5HA TGF-β1 (actN5HAb1) fusion.

SEQ ID NO: 37 shows the amino acid sequence of the precursor N+5HA-TGF-β1 (actN5HAb1) fusion.

SEQ ID NO: 38 shows the nucleic acid and deduced protein sequence of the precursor porcine latent N+5HA TGF-β1 (latN5HAb1) fusion.

SEQ ID NO: 39 shows the amino acid sequence of the precursor N+5HA-TGF-β1 (latN5HAb1) fusion.

DETAILED DESCRIPTION OF THE DISCLOSURE

I. Abbreviations

| | |
|---|---|
| LAP: | latency associated peptide |
| NMR: | nuclear magnetic resonance |
| DTT: | dithiothreitol |
| ELISA: | enzyme linked immunoassay |
| SELISA: | sandwich ELISA |
| TGF: | transforming growth factor |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); A. D. Smith et al. (eds.), *Oxford Dictionary of Biochemistry and Molecular Biology*, published by Oxford Univ. Press, 1997 (ISBN 0-19-854768-4); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanations of terms are provided:

Associating: A process of reversibly bringing two chemical entities (such as biological macromolecules, e.g., proteins) together to form a complex, usually where the association involves specific interactions between the macromolecules. Two biological macromolecules may associate with each other automatically, for instance during synthesis of the molecules, or may require one or more chaperon-like molecules to mediate the association process.

Cleaving: To split a chemical bond, such as a chemical linkage between the subunits of a biopolymer. Thus, breaking a peptide bond in a oligo- or polypeptide (e.g., in a protein) is a cleavage event. Cleaving may be relatively non-specific, for instance though a purely chemical process of acidic hydrolysis. In some instances, cleavages are mediated by a biochemical or biological process, for instance through the process of an enzyme such as a protease (in the case of a peptide cleavage) or a nuclease (in the case of cleavage of a poly-nucleotide). As will be recognized by those of ordinary skill in the art, enzyme-based cleavage is often a specific event, and for instance may be influenced by the primary and/or secondary structure of the molecule (e.g., biopolymer) that is being cleaved.

A specific class of cleavage events are those involved in maturation of precursor proteins, for instance the proteolytic cleavage ("removal) of a pro-region portion of a precursor (e.g., a latent) protein.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Examples of useful epitope tags include FLAG, T7, HA (hemagglutinin) and myc. The FLAG tag (DYKDDDDK) was used in some particular examples disclosed herein because high quality reagents are available to be used for its detection. Epitope tags can of course have one or more additional functions, beyond recognition by an antibody.

Functionalized: To add a function to a molecule, such as a protein, that is not a native function of that molecule. A functionalizing peptide portion is a portion of a protein (e.g., a peptide or protein domain), for instance a part of a fusion protein, that provides a non-native function to the fusion. Functions that can be added in this manner include (but are not limited to) identification (particularly distinction from the native subject protein), targeting, translocation, and distinct biological function (such as addition of an active protein domain).

Fusion protein: A protein comprising two amino acid sequences that are not found joined together in nature. Functionalized TGF-β fusion proteins specifically comprise at least (1) a sequence of a mature region of a TGF-β family protein and (2) a functionalizing peptide portion placed at either end of or within the coding region of the mature TGF-β family protein. Such functionalized TGF-β fusion proteins can additionally include other protein elements, such as one or more additional functionalizing peptide portion, a pro-region of a TGF-β family protein (which may assist in folding, assembly, and/or secretion of the fusion protein), and/or a linker between any of such protein portions ("domains").

Injectable composition: A pharmaceutically acceptable fluid composition comprising at least one active ingredient, e.g., a functionalized TGF-β family protein fusion. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

Isolated: An "isolated" biological component (such as a nucleic acid molecule, protein or organelle) has been substantially separated or purified away from other biological components in the cell of the organism in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell, as well as chemically synthesized biopolymers.

Linker: A peptide, usually between two and about 150 amino acid residues in length, that serves to join two protein domains in a multi-domain (multi-part) fusion protein. Examples of specific linkers can be found, for instance, in Hennecke et al. (*Protein Eng.* 11:405–410, 1998); and U.S. Pat. Nos. 5,767,260 and 5,856,456.

Linkers may be repetitive or non-repetitive. One classical repetitive linker used in the production of fusion proteins is the $(Gly_4Ser)_3$ (or $(GGGGS)_3$ or $(G_4S)_3$) linker. More recently, non-repetitive linkers have been produced, and methods for the random generation of such linkers are known (Hennecke et al., *Protein Eng.* 11:405–410, 1998). In addition, linkers may be chosen to have more or less secondary character (e.g., helical character, U.S. Pat. No. 5,637,481) depending on the conformation desired in the final fusion protein. The more secondary character a linker possesses, the more constrained the structure of the final fusion protein will be. Therefore, substantially flexible linkers that are substantially lacking in secondary structure allow flexion of the fusion protein at the linker.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, usually between about 6 and about 300 nucleotides in length. The term "oligonucleotide analog" refers to moieties that function similarly to oligonucleotide but have non-naturally occurring portions. For example, oligonucleotide analogs can contain altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 300 nucleotides in length, for example a sequence (such as DNA or RNA) that is at least 6 bases, for example at least 8, 10, 15, 20, 25, 30, 35, 40, 45, 50, 100, 200, or even 300 bases long, or from about 6 to about 100 bases, for example about 10–50 bases, such as 12, 15, 20, 30, or 40 bases.

Open reading frame: A series of nucleotide triplets (codons) coding for amino acids without any internal termination codons. These sequences are usually translatable into a peptide.

Operably linked nucleic acid: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide: Any compound containing two or more amino-acid residues joined by amide bonds, formed from the carboxyl group of one residue and the amino group of the next. The broad term "peptide" includes oligopeptides, polypeptides, and proteins.

Peptide Nucleic Acid (PNA): An oligonucleotide analog with a backbone comprised of monomers coupled by amide (peptide) bonds, such as amino acid monomers joined by peptide bonds.

Peptide tag: A peptide sequence that is attached (for instance through genetic engineering) to another peptide or a protein, to provide a function to the resultant fusion. Peptide tags are usually relatively short in comparison to a protein to which they are fused; by way of example, peptide tags are four or more amino acids in length, such as, 5, 6, 7, 8, 9, 10, 15, 20, or 25 or more amino acids. Usually a peptide tag will be no more than about 100 amino acids in length, and may be no more than about 75, no more than about 50, no more than about 40, or no more than about 30.

In preferred embodiments, the addition of the functionalizing peptide tag will not substantially reduce a native function of the TGF-β molecule to which it is attached. Thus, in particular examples, the addition of a functionalizing peptide tag will reduce a function of the TGF-β molecule by no more than about 50%, about 40%, about 30%, about 20%, or about 10%. In certain specific examples, the activity of the so-modified TGF-β molecule will be reduced by no more than about 5%, about 3%, about 1%, or may in fact not be reduced at all. Native TGF-β activity can be measured using any of various known.

Peptide tags confer one or more different functions to a fusion protein (thereby "functionalizing" that protein), and such functions can include (but are not limited to) antibody binding (an epitope tag), purification, translocation, targeting, and differentiation (e.g., from a native protein). In addition, a recognition site for a protease, for which a binding antibody is known, can be used as a specifically cleavable epitope tag. The use of such a cleavable tag can provide selective cleavage and activation of a protein (e.g., by replacing the cleavage site in TGF-β1 with that for pro-caspase 3. Alternatively the system developed by in the Dowdy laboratory (Vocero-Akbani et al, *Nat Med*. 5:29–33, 1999) could be use to provide specificity of such cleavage and activation.

Detection of the tagged molecule can be achieved using a number of different techniques. These include: immunohistochemistry, immunoprecipitation, flow cytometry, immunofluorescence microscopy, ELISA, immunoblotting ("western"), and affinity chromatography.

Epitope tags add a known epitope (antibody binding site) on the subject protein, to provide binding of a known and often high-affinity antibody, and thereby allowing one to specifically identify and track the tagged protein that has been added to a living organism or to cultured cells. Examples of epitope tags include the myc, T7, GST, GFP, HA (hemagglutinin) and FLAG tags. The first four examples are epitopes derived from existing molecules. In contrast, FLAG is a synthetic epitope tag designed for high antigenicity (see, e.g., U.S. Pat. Nos. 4,703,004 and 4,851,341).

Purification tags are used to permit easy purification of the tagged protein, such as by affinity chromatography. A well-known purification tag is the hexa-histidine (6x His) tag, literally a sequence of six histidine residues. The 6x His protein purification system is available commercially from QIAGEN (Valencia, Calif.), under the name of QIAexpress®.

One representative translocation/transduction peptide (which serves to facilitate translocation of a protein into a cell) is the $Tat_{49-57}$ fragment from the human immunodeficiency virus (HIV). See, for instance, Vecero-Akbani et al. (*Methods Enzymol*. 322:508–521, 2000); Falnes et al. (*Biochem*. 40:4349–4358, 2001); and Becker-Hapak et al. (*Method* 24:247–256,2001). Antibodies are available and can be produced that recognize this peptide, and so it can be viewed as a multi-functional peptide.

A single tag peptide can serve more than one purpose; any attached tag, for instance, will increase the molecular weight of the fusion protein and thereby permit differentiation between the tagged and native proteins. Antibodies specific for an "epitope tag" can be used to construct an immunoaffinity column, thus permitting an epitope tag to be used for purification of the tagged protein. Likewise, in some instances monoclonal antibodies specific for a purification tag are available (e.g., anti-6x His peptide monoclonal antibodies, which are available through QIAGEN or CLONTECH, Palo Alto, Calif.).

Pharmaceutically acceptable carriers: The pharmaceutically acceptable carriers useful in the disclosed compositions and methods are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmacodynamics is the branch of pharmacology dealing with the effects of drugs on the body, i.e., with the physiological, therapeutic, and toxicological responses to drugs with particular regard to the extent, mechanism, and time course of such effects on living organisms (see, Goodman and Gilman, "*The Pharmacological Basis of Therapeutics*," Macmillan Publ. Co., 1985, LC #85-15356, Chapter 2, pages 34–65). The study of pharmacodynamics may include measurement or determination of the cellular site of drug action, dose-response relationship(s), structure-activity relationship(s), or quantitation of drug-receptor interactions, for example.

Pharmacokinetics is the branch of pharmacology dealing quantitatively with the movement of drugs (e.g., proteins) within the body, i.e., with the absorption (uptake into the system), bioavailability (fraction of the drug absorbed as such into systemic circulation), distribution (movement around the available volume of the body), metabolism (conversion of the drug into non-active form(s)), and elimination/clearance (the ability of a body to eliminate the drug from the system) of drugs. Each of these factors influence the magnitude of a drug effect(s), and how much of the drug found at sites at different times after its application to a system (see, Levine, "*Pharmacology: Drug*

Actions and Reactions," Little, Brown and Co., Ltd., 1983, ISBN 0-316-5222-8, Chapter 10, pages 211–247, and Goodman and Gilman, "The Pharmacological Basis of Therapeutics," Macmillan Publ. Co., 1985, LC #85-15356, Chapter 1, pages 3–34).

Pharmacological properties of a drug: The properties of a drug (any non-food chemical agent, such as a protein, that affects a living organism) in a subject, in particular as relates to the use of drugs to treat, cure, prevent, diagnose, or prognose disease. Pharmacological properties include the pharmacodynamic and pharmacokinetic properties, for instance.

Polymorphism: Variant in a sequence of a gene. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased gene product. The term polymorphism may be used interchangeably with allele or mutation, unless context clearly dictates otherwise.

Polymorphisms can be referred to, for instance, by the nucleotide position at which the variation exists, by the change in amino acid sequence caused by the nucleotide variation, or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth).

Probes and primers: A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (*In Molecular Cloning: A Laboratory Manual*, CSHL, New York, 1989) and Ausubel et al. (*In Current Protocols in Molecular Biology*, John Wiley & Sons, New York, 1998).

Primers are short nucleic acid molecules, for instance DNA oligonucleotides about 6 nucleotides or more in length. Longer DNA oligonucleotides may be about 10, 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art. Other examples of amplification include, but are not limited to, strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (*In Molecular Cloning: A Laboratory Manual*, CSHL, New York, 1989), Ausubel et al. (ed.) (*In Current Protocols in Molecular Biology*, John Wiley & Sons, New York, 1998), and Innis et al. (PCR Protocols, *A Guide to Methods and Applications*, Academic Press, Inc., San Diego, Calif., 1990). Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of a TGF-$\beta$-encoding nucleotide or flanking region thereof (such as a "TGF-$\beta$1 primer" or "TGF-$\beta$1 probe") will anneal to a target sequence with a higher specificity than a corresponding primer of only 15 nucleotides. Thus, in order to obtain greater specificity, probes and primers can be selected that comprise at least 20, 25, 30, 35, 40, 45, 50 or more consecutive nucleotides of the target nucleotide sequences.

Protein: A biological molecule expressed by an encoding nucleic acid molecule (e.g., a gene) and comprised of amino acids. Proteins are a subset of the broader molecular class "peptide."

Purified: The term purified does not require absolute purity; rather, it is intended as a relative term. Thus, for example, a "purified" fusion protein preparation is one in which the fusion protein is more enriched than the protein is in its generative environment, for instance within a cell or in a biochemical reaction chamber. Preferably, a preparation of fusion protein is purified such that the fusion protein represents at least 50% of the total protein content of the preparation.

Recombinant nucleotide: A recombinant nucleic acid molecule is one that has a sequence that is not naturally occurring or has a sequence that is made by an artificial combination of two otherwise separated segments of sequence. This artificial combination can be accomplished by chemical synthesis or, more conmmonly, by the artificial manipulation of isolated segments of nucleic acids, e.g., by genetic engineering techniques.

Similarly, a recombinant protein is one encoded for by a recombinant nucleic acid molecule.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS. USA* 85: 2444, 1988); Higgins and Sharp (*Gene*, 73: 237–244, 1988); Higgins and Sharp (CABIOS 5: 151–153, 1989); Corpet et al. (*Nuc. Acids Res.* 16: 10881–10890, 1988); Huang et al. (*Comp. Appls Biosci.* 8: 155–165, 1992); and Pearson et al. (*Meth. Mol. Biol.* 24: 307–31, 1994). Altschul et al. (*Nature Genet.*, 6: 119–129, 1994) presents a detailed consideration of sequence alignment methods and homology calculations.

The alignment tools ALIGN (Myers and Miller, CABIOS 4:11–17,1989) or LFASTA (Pearson and Lipman, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J Mol. Biol*. 215:403–410, 1990; Gish. & States, *Nature Genet*. 3:266–272, 1993; Madden et al. *Meth. Enzymol*. 266:131–141, 1996; Altschul et al., *Nucleic Acids Res*. 25:3389–3402, 1997; and Zhang & Madden, *Genome Res*. 7:649–656, 1997.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10–20 amino acids, and may possess sequence identities of at least 85%, at least 90%, at least 95%, or at least 99%. depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (*In Molecular Cloning: A Laboratory Manual*, Cold Spring Harbor, N.Y., 1989) and Tijssen (*Laboratory Techniques in Biochemistry and Molecular Biology* Part I, Ch. 2, Elsevier, N.Y., 1993). Nucleic acid molecules that hybridize under stringent conditions to the disclosed bispecific fusion protein sequences will typically hybridize to a probe based on either the entire fusion protein encoding sequence, an entire binding domain, or other selected portions of the encoding sequence under wash conditions of 0.2 x SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specific binding agent: An agent that binds substantially only to a defined target. Thus a peptide-specific binding agent binds substantially only the defined peptide, or a peptide region within a protein, such as a fusion protein. As used herein, the term "[X] specific binding agent," where [X] refers to a specific protein or peptide, includes anti-[X] antibodies (and functional fragments thereof) and other agents (such as soluble receptors) that bind substantially only to [X].

Antibodies may be produced using standard procedures described in a number of texts, including Harlow and Lane (*Antibodies, A Laboratory Manual*, CSHL, New York, 1988). The determination that a particular agent binds substantially only to the target protein or peptide may readily be made by using or adapting routine procedures. One suitable in vitro assay makes use of the Western blotting procedure (described in many standard texts, including Harlow and Lane, *Antibodies, A Laboratory Manual*, CSHL, New York, 1988). Western blotting may be used to determine that a given protein binding agent, such as an anti-TGF-β family protein monoclonal antibody, binds substantially only to the specified TGF-β family protein.

Shorter fragments of antibodies can also serve as specific binding agents. For instance, FAbs, Fvs, and single-chain Fvs (SCFvs) that bind to a protein or peptide [X] would be [X]-specific binding agents. These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb')$_2$, the fragment of the antibody obtained by treating whole antibody with the enzyme pepsin without subsequent reduction; (4) F(Ab')2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

TGF-β family of proteins: A family of secreted signaling molecules involved in a number of cellular and developmental processes in eukaryotic cells, including inflammation, immune surveillance, and neoplasia. Members of the TGF-β family of proteinsinclude, but are not limited to: TGF-β2, TGF-β3, TGF-β1, TGF-β4 (chicken), TGF-β5 (Xenopus), GDF-9 (mouse/human), BMP-16/nodal (mouse), Fugacin (Xenopus), BMP3, Sumitomo-BIP/GDF-10 (mouse), ADMP (Xenopus), BMP-9, Dorsalin-1 (Chicken), BMP-10, BMP-13/GDF-6 (mouse), Radar (Zebrafish), GDF-1/CDMP-1 (mouse/human), BMP-12/

Figure 1:
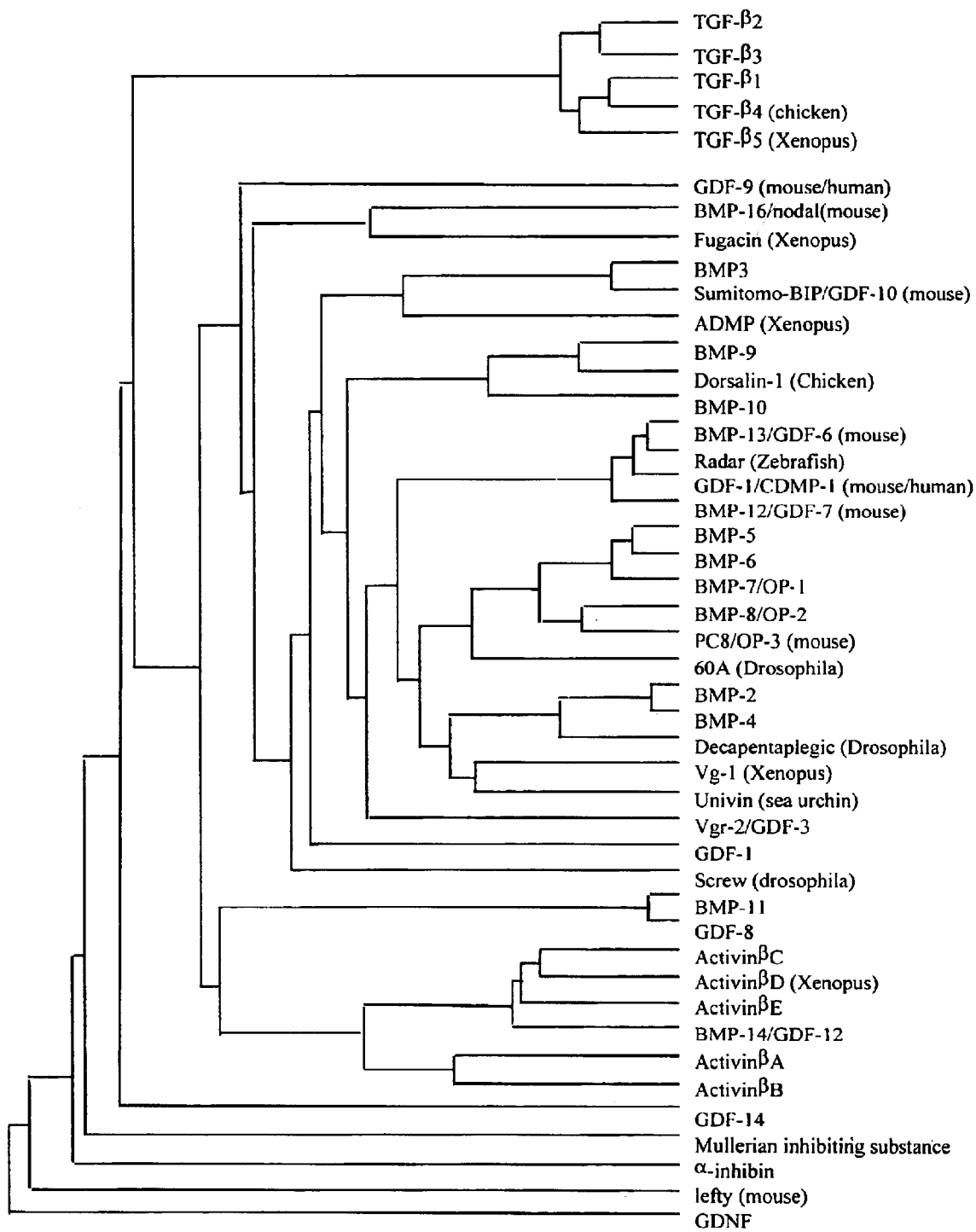
FIG. 1 shows a phylogenetic tree illustrating the relatedness of several members of the TGF-β superfamily of proteins.

GDF-7 (mouse), BMP-5, BMP-6, BMP-7/OP-1, BMP-8/OP-2, PC8/OP-3 (mouse), 60A (Drosophila), BMP-2, BMP4, Decapentaplegic (Drosophila), Vg-1 (Xenopus), Univin (sea urchin), Vgr-2/GDF-3, GDF-1, Screw (Drosophila), BMP-11, GDF-8, ActivinβC, ActivinβD (Xenopus), ActivinβE, BMP-14/GDF-12, ActivinβA, ActivinβB, GDF-14, Mullerian inhibiting substance, and α-inhibin. The phylogenetic relationship between these proteins is shown in FIG. 1.

The term "TGF-β family protein function" includes all functions that are associated with a TGF-β family protein, including for instance secondary folding of each TGF-β monomer, tertiary association between the members of the multimeric (e.g., homodimeric) TGF-β complex, maturation by cleavage and/or removal of the pro-region (LAP), secretion of the protein from the cell in which it was translated, specific receptor binding, and down-stream activities that result from the binding of a TGF-β family ligand protein with its cognate receptor(s). Such downstream activities include (depending on the TGF-β family member examined and the system used), for instance, regulation of cell growth (proliferation), stimulation of cell growth or proliferation, stimulation of cell differentiation, inhibition of cell growth or proliferation, regulation of cytokine production, induction of cellular differentiation, cell cycle inhibition, control of adhesion molecule expression, stimulation of angiogenesis, induction of leukocyte chemotaxis, induction of apoptosis, suppression of lymphocyte activation, suppression of inflammation, enhances wound healing by mechanisms including, stimulation of synthesis of matrix proteins, regulation of immunoglobulin production, including isotype switch recombination, and suppression of tumorigenesis.

Fusions of the current disclosure maintain substantial TGF-β biological activity, by which it is meant that the fusion protein maintains at least one biological activity at a level of at least approximately 50% of the native equivalent TGF-β protein. In specific embodiments, the fusion protein will maintain a greater level of one or more specific TGF-β biological activities, such as at least 60%, at least 70%, at least 80%, or at least 90% or more of the native activity. In certain embodiments, a functionalized TGF-β fusion protein of the disclosure will display a specific TGF-β biological activity equal to or greater than that observed with the equivalent native TGF-β protein, for instance at least 100% of the native activity, or 105%, 110%, 120%, or even 150% of native (non-fused) TGF-β.

Different members of the TGF-β family have different biological specificities and activities. Specificities of the listed TGF-β family proteins are known to one of ordinary skill in the art. See, for instance, Doetschman, *Lab.Anim.Sci.* 49:137–143, 1999; Letterio and Roberts, *Annu. Rev. Immunol.* 16:137–61:137–161, 1998; Wahl, *J. Exp. Med.* 180:1587–1590, 1994; Letterio and Roberts, *J. Leukoc. Biol.* 59:769–774, 1996; Piek et al., FASEB J. 13:2105–2124, 1999; Heldin et al., *Nature* 390:465–471, 1979; and De Caestecker et al., *J. Nat'l. Cancer Inst.*, 92:1388–1402, 2000.

Therapeutically effective amount of a protein: A quantity of a protein sufficient to achieve a desired effect in a subject being treated. For instance, when referring to a functionalized TGF-β family protein fusion this can be the amount necessary to induce a dose-dependent tissue specific effect. Examples of clinically relevant TGF-β functionality include:

the amount of TGF-β that, when applied topically to mucosal surfaces, can inhibit cycling of basal epithelial cells;

the amount of TGF-β that, when administered topically to the epidermis, can enhance collagen deposition and promote accelerated wound healing; and the amount of TGF-β that can suppress local inflammatory reactions when administered locally at various sites.

An effective amount of a protein (such as a fusion protein of the disclosure) may be administered in a single dose, or in several doses, for example daily, during a course of treatment. However, the effective amount of protein will be dependent on the protein applied, the subject being treated, the severity and type of the affliction, and the manner of administration of the protein. For example, a therapeutically effective amount of a fusion protein can vary from about 0.01 mg/kg body weight to about 1 g/kg body weight.

The fusion proteins disclosed herein have equal application in medical and veterinary settings. Therefore, the general term "subject being treated" is understood to include all animals (e.g. humans, apes, dogs, cats, horses, and cows).

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known to those of ordinary skill in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the compositions and methods herein, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

This disclosure provides functionalized TGF-β fusion proteins that maintain substantial TGF-β biological activity. These fusion proteins are achieved by placing a functionalizing peptide between the pro- and active (mature) portions of a TGF-β protein, or at a relatively non-conserved site within the mature region of a TGF-β protein, or within a few residues (for instance within 15 or fewer amino acid residues) of the maturation cleavage site between the pro- and active (mature) portions of the TGF-β protein.

Encompassed herein are functional TGF-β family fusion proteins that contain a functionalizing peptide portion for detecting, quantifying or providing a specific additional function to the fusion protein and a mature TGF-β family protein, both as a monomer and in the form of a dimer (e.g., a homodimer). Also encompassed are nucleic acid molecules encoding such fusion proteins, and conservative substitutions of such molecules.

Optionally, functionalized fusion proteins disclosed herein can also include a pro-region (latency associated peptide) of a TGF-β family protein, which for instance can be located to provide targeting and/or assembly and/or processing of the fusion protein. In certain embodiments, the pro-region is located at the N-terminal region of the fusion protein.

Also encompassed herein are fusion proteins in which the TGF-β family member portion of the fusion protein is a functional variant of a naturally occurring TGF-β family protein.

TGF-β family proteins useful for providing portions of the encompassed fusions proteins include TGF-β2, TGF-β3, TGF-β1, TGF-β4 (chicken), TGF-β5 (Xenopus), GDF-9 (mouse/human), BMP-16/nodal (mouse), Fugacin (Xenopus), BMP3, Sumitomo-BIP/GDF-10 (mouse), ADMP (Xenopus), BMP-9, Dorsalin-1 (Chicken), BMP-10, BMP-13/GDF-6 (mouse), Radar (Zebrafish), GDF-1/CDMP-1 (mouse/human), BMP-12/GDF-7 (mouse), BMP-5, BMP-6, BMP-7/OP-1, BMP-8/OP-2, PC8/OP-3 (mouse), 60A (Drosophila), BMP-2, BMP4, Decapentaplegic (Drosophila), Vg-1 (Xenopus), Univin (sea urchin), Vgr-2/GDF-3, GDF-1, Screw (Drosophila), BMP-11, GDF-8, ActivinβC, ActivinβD (Xenopus), ActivinβE, BMP-14/GDF-12, ActivinβA, ActivinβB, GDF-14, Mullerian inhibiting substance, and α-inhibin. Specific examples of disclosed fusions contain mature and/or pro-regions from TGF-β1, TGF-β2, or TGF-β3. The mature and pro-region contained with a single fusion are not necessarily derived from the same TGF-β family protein, though in some embodiments the mature and pro-regions will be derived from the same native TGF-β family protein.

Dimers formed from the functional TGF-β family fusion proteins can be made, for instance, by methods that include expressing a nucleic acid molecule in a eukaryotic cell to produce a monomer fusion protein. The monomers can then be associated together to form a dimer. Such nucleic acid molecules can include a sequence encoding a functionalizing peptide portion of the functional TGF-β family fusion protein, a sequence encoding the desired mature TGF-β family protein, and a sequence encoding a pro-region (latency associated peptide) of a TGF-β family protein. In certain embodiments, the pro-region (latency associated peptide) is located to provide targeting and/or assembly and/or processing of the fusion protein encoded for by the nucleic acid. This will often be at or near the N-terminal end of the overall fusion protein construct. Thus, the sequence encoding the pro-region may be located upstream to both the sequence encoding the functionalizing peptide portion and the sequence encoding the mature TGF-β family protein.

In certain embodiments, the pro-region (latency associated peptide) is cleaved from the functionalized TGF-β fusion protein monomers disclosed herein. Likewise, in certain embodiments the pro-region is cleaved from one or both of the monomers in dimers disclosed herein. Methods are provided for actively cleaving the pro-region from the monomers, for instance through the addition of a protease to a sample of the monomer. Alternatively, the pro-region in some instances is removed through the expression of the monomer construct in a cell or system that contains such a protease.

In specific embodiments, the functionalizing peptide portion of a disclosed TGF-β fusion protein is at the N-terminus of the mature TGF-β family protein portion of the fusion. Such a fusion protein is exemplified by NFLAG-TGF-β1; nucleic acid and/or amino acid sequences related to this fusion are shown in SEQ ID NOs: 8–11.

In other specific embodiments, the functionalizing peptide portion is inserted within the mature functional TGF-β family protein. Such insertion can be, for instance, at a position of relatively low sequence conservation within the TGF-β super family. In examples of such fusion proteins, the functionalizing peptide portion is inserted between about residues 11 and 12 of the mature TGF-β family protein. Such a fusion protein is exemplified by 11/12FLAG-TGF-β1; nucleic acid and/or amino acid sequences related to this fusion are shown in SEQ ID NOs: 12–15.

In other examples of fusion proteins in which the functionalizing peptide is inserted within the mature TGF-β family protein, a portion of the TGF-β family protein may be repeated both before and after the inserted peptide. For instance, in some specific examples, the peptide is inserted after five amino acid residues of the mature TGF-β family protein, and these five amino acids are then repeated after the peptide (such that the entire TGF-β mature protein occurs in the fusion after the peptide). Such a fusion protein is exemplified by N+5FLAG-TGF-β1 (SEQ ID NOs: 16 & 17); N+5HA-TGF-β1 (SEQ ID NOs: 20 & 21); N+5FLAG TGF-β2 (SEQ ID NOs: 24 & 25); N+5HA TGF-β2 (SEQ ID NOs: 26 & 27); N+5FLAG TGF-β3 (SEQ ID NOs: 28 & 29); N+5HA TGF-β3 (SEQ ID NOs: 30 & 31); N+5FLAG TGF-β1 (SEQ ID NOs: 32 & 33); N+5FLAG-TGF-β1 (SEQ ID NOs: 34 & 35); N+5HA TGF-β1 (SEQ ID NOs: 36 & 37); and N+5HA TGF-β1 (SEQ ID NOs: 38 & 39). Though these illustrated fusions have the peptide inserted after five amino acids of the mature TGF-β family protein, it could be inserted after a different number of amino acids, for instance, after one, after two, after three, after four, after six, after seven, or after eight amino acids. In this particular class of constructs, the amino acid residues of the mature TGF-β family protein that are located before (amino-terminal to) the functionalizing peptide are usually also repeated after the peptide, though they need not all be repeated.

The functionalizing peptide portion of disclosed functional TGF-β fusion proteins may be any amino acid sequence that confers a functionality to the fusion protein. Thus, a functionalizing peptide portion can be a tag, a targeting moiety, or a biologically active protein domain. By way of example, a targeting moiety may include a domain of a cell surface binding protein. Biologically active protein domains may include a toxin, an enzyme, or a fluorescent peptide, for instance. Examples of tags include generally epitope tags, purification tags, and identification tags. Specific examples of peptide tags include a FLAG tag, a c-myc tag, a 6x His tag, a HA tag, a Tat tag, a T7 tag, a GFP peptide, and a GST peptide.

Exemplary nucleic acid molecules encoding functionalized and functional TGF-β fusion proteins include the sequences show in SEQ ID NOs: 8, 10, 12, 14, 16, 20, 24, 26, 28, 30, 32, 34, 36, and 38, for instance, and conservative substitutions thereof. Also encompassed herein are recombinant nucleic acid molecule that include a promoter sequence operably linked to an isolated nucleic acid molecule encoding a functionalized and functional TGF-β fusion protein described herein. Transgenic cells (such as bacterial or eukaryotic cells, for instance yeast or mammalian cells) containing such a recombinant nucleic acid molecule are also encompassed, as are transgenic organisms containing such a transgenic cell.

Further embodiments are methods of adding a non-native functionality to a mature biologically active TGF-β family protein. Such methods involve inserting a functionalizing peptide portion (such as a tag, a targeting moiety, or a biologically active protein domain) between a TGF-β pro-region and a TGF-β mature protein, or at a relatively non-conserved site within the mature region of a TGF-β family protein. Representative TGF-β family proteins that can be used to construct such fusions include TGF-β2, TGF-β3, TGF-β1, TGF-β4 (chicken), TGF-β5 (Xenopus), GDF-9 (mouse/human), BMP-16/nodal (mouse), Fugacin (Xenopus), BMP3, Sumitomo-BIP/GDF-10 (mouse), ADMP (Xenopus), BMP-9, Dorsalin-1 (Chicken), BMP-10, BMP-13/GDF-6 (mouse), Radar (Zebrafish), GDF-1/CDMP-1 (mouse/human), BMP-12/GDF-7 (mouse), BMP-5, BMP-6, BMP-7/OP-1, BMP-8/OP-2, PC8/OP-3 (mouse), 60A (Drosophila), BMP-2, BMP4, Decapentaplegic (Drosophila), Vg-1 (Xenopus), Univin (sea urchin), Vgr-2/GDF-3, GDF-1, Screw (Drosophila), BMP-11, GDF-8, ActivinβC, ActivinβD (Xenopus), ActivinβE, BMP-14/GDF-12, ActivinβA, ActivinβB, GDF-14, Mullerian inhibiting substance, and α-inhibin.

Further embodiments include methods using TGF-β fusion proteins disclosed herein to treat a disease that responds to administration of a TGF-β family protein, or assess a pharmalogic property of the protein. Such methods involve administering a therapeutically sufficient amount of a disclosed fusion protein to a subject. In certain of such methods, the functionalizing peptide portion of the fusion is for detection or quantifying the fusion protein, and specific examples of such methods further involve detecting and/or quantifying the fusion protein. A pharmacokinetic or pharmacodynamic calculation can be performed on data generated using such methods. Such calculation can involve a pharmacodynamic calculation of cellular site of protein action, dose-response relationship(s), structure-activity relationship(s), or quantitation of protein-receptor interaction(s). Alternatively, such calculations can involve a pharmacokinetic calculation of absorption, bioavailability, distribution, metabolism, or elimination/clearance of the protein.

IV. Functionalized TGF-β Family Protein Fusions

The current disclosure provides TGF-β fusion proteins that can be expressed in mammalian cells while maintaining physiological function(s) of the fusion, and in particular the TGF-β family functionality of the fusion protein. The TGF-β family protein is genetically fused with a functionalizing peptide, such as a peptide tag or a targeting or other functional domain. Representative molecules constructed using the disclosed method comprise an epitope tag (such as the FLAG tag) fused to TGF-β1 near the amino-terminus of the mature protein. This placement of the functionalizing peptide places it effectively in the middle of the TGF-β precursor protein, between the pro-region and the mature region or near this juncture. The tagged protein can then be expressed with the pro-region attached to enable proper folding of the TGF-β homodimer.

Tagging or otherwise generating a fusion of a TGF-β protein is complicated by the fact that proteins in the TGF-β family are initially synthesized as inactive, latent precursors (Roberts, *Annu. Rev. Immunol.* 16:137–61:137–161, 1998) that contain a relatively large N-terminal pro-region, also referred to as the latency associated peptide (LAP). LAP is required for both proper folding and secretion of TGF-β family proteins. Removal of LAP from the mature region prior to expression results in a loss of biological activity.

Previous attempts to add epitope tags to TGF-β1 resulted in biologically inactive fusions (Wakefield et al. *Growth Factors*, 5:243–253, 1991). The TGF-β family fusion proteins described herein overcome the difficulties encountered by previous constructs, particularly low bio-activity and poor folding, because the functionalizing peptide portion of the fusion is placed at the pro-mature junction of the TGF-β family protein, or at a relatively unconserved position within the mature portion of the protein. This permits the LAP to provide folding, assembly, and targeting activity while still producing a mature fusion with the functionalizing peptide intact.

Two representative functionalized TGF-β fusion proteins described herein are FLAG-TGF-β1 (wherein the FLAG epitope tag is inserted immediately before the N-terminus of mature TGF-β1) and 11/12FLAG (wherein the FLAG epitope tag is inserted between amino acid residues 11 and 12 of the mature TGF-β1). Each of these fusions is demonstrated to be functional, based on in vitro and in vivo biological and biochemical analyses. Although the amount of FLAG-tagged molecules secreted was lower than un-tagged control TGF-β1, even dilutions of the FLAG-TGF-β1 culture supernatants as great as 1:256 were still as effective as supernatants from cells transfected with WT TGF-β1 in inhibiting cell growth. This indicates that the functionalized TGF-β fusions may have higher specific activity than does native TGF-β.

With the provision herein of functionalized TGF-β fusion proteins, and in particular the description of specific fusions, the construction of other TGF-β fusions that maintain native bio-activity while having an addition function conveyed by a functionalizing peptide (such as a tag, a targeting moiety, or a biologically active protein), is now enabled. The construction of such additional molecules will now be described.

A. Selection of Fusion Components.

The choice of appropriate protein domains and/or peptides for incorporation into the disclosed functionalized TGF-β fusion proteins will be dictated by the desired specificity (or lack of specificity) of the TGF-β portion and the desired added function (e.g., identification or isolation of the fusion protein, targeting of the fusion, and so forth).

Fusion proteins of this disclosure include at least a functional portion of a TGF-β family protein. Representative members of the TGF-β family of proteins include: TGF-β2, TGF-β3, TGF-β1, TGF-β4 (chicken), TGF-β5 (Xenopus), GDF-9 (mouse/human), BMP-β16/nodal (mouse), Fugacin (Xenopus), BMP3, Sumitomo-BIP/GDF-10 (mouse), ADMP (Xenopus), BMP-9, Dorsalin-1 (Chicken), BMP-β10, BMP-13/GDF-6 (mouse), Radar (Zebrafish), GDF-1/CDMP-1 (mouse/human), BMP-12/GDF-7 (mouse), BMP-5, BMP-6, BMP-7/OP-1, BMP-8/OP-2, PC8/OP-3 (mouse), 60A (Drosophila), BMP-2, BMP-4, Decapentaplegic (Drosophila), Vg-1 (Xenopus), Univin (sea urchin), Vgr-2/GDF-3, GDF-1, Screw (Drosophila), BMP-11, GDF-8, ActivinβC, ActivinβD (Xenopus), ActivinβE, BMP-14/GDF-12, ActivinβA, ActivinβB, GDF-14, Mullerian inhibiting substance, and α-inhibin. Any of the listed TGF-β family proteins, and any other proteins identified as belonging to the TGF-β family (or "superfamily") can be used to construct fusions. Different members of the family can be selected depending on, for instance, the biological system in which the fusion is intended to function (e.g., mammalian) and/or the desired biological specificity of TGF-β activity. Specificities of the listed TGF-β family proteins are known to one of ordinary skill in the art. See, for instance, Doetschman, *LabAnim.Sci.* 49:137–143, 1999; Letterio and Roberts, *Annu. Rev. Immunol.* 16:137–61:137–161, 1998; Wahl, *J. Exp. Med.* 180:1587–1590, 1994; Letterio, Roberts, *J. Leukoc. Biol.* 59:769–774, 1996; Piek et al., FASEB J. 13:2105–2124, 1999; Heldin et al., *Nature* 390:465–471, 1979; and De Caestecker et al., *J. Nat'l Cancer Inst.,* 92:1388–1402, 2000. Also, see Roberts and Sporn, *Mol. Reprod. Dev.* 32:91–98, 1992; Roberts et al., *Ciba. Found. Symp.* 157:7–15, 1991; Kingsley, Genes Dev. 8:133–146, 1994; Roberts and Sporn, "The transforming growth factors-β" In: *Peptide Growth Factors and their Receptors.* (Sporn and Roberts, eds.), 95:419–472, 1990.

The pro-region of a TGF-β family protein can be included in the functionalized fusion protein. Such inclusion is advantageous for the correct folding, dimerization, and secretion of the fusion protein in eukaryotic cell systems, and may in some instances be necessary to achieve maximal TGF-β biological activity in the resultant fusion. The pro-region is usually placed upstream (towards the amino-terminus) of the mature portion of the TGF-β protein, and may be cleaved off during production of the protein. In most instances, removal of the pro-region is necessary for complete activity of the fusion protein, since it is effective at blocking binding of the TGF-β protein at its receptor(s). Though the detailed examples herein describe constructs in which the pro-region and mature regions are selected from the same TGF-β protein, it is believed that this is not necessary for the function of the disclosed fusion proteins.

Likewise, selection of a functionalizing peptide portion for a fusion protein of the current disclosure will depend on the purpose of the fusion. Functionalizing peptide portions can be short peptides (such as tags), or longer peptide molecules or protein domains or proteins (such as targeting domains or enzymatically active proteins). Merely by way of example, functionalizing peptide tags that can be used in fusions according to this disclosure include epitope tags (such as myc, T7, GST, HA, or FLAG), translocation/transduction tags (such as Tat), purification tags (such as the hexa-histidine tag) and other peptide labels, such as green fluorescent protein (GFP). An epitope tag can be added to a TGF-β fusion protein in order to allow the resultant fusion protein to be identified through the use of an antibody that recognizes the epitope. A purification tag can be added to a TGF-β fusion protein in order to allow the resultant fusion protein to be purified, for instance through column chromatography.

The fusion proteins as provided herein also can be functionalized through the addition of a cell-targeting protein domain or protein. Such domains can be used to specifically target the TGF-β fusion to a specific cell type, tissue type, or organ (the "target" of that fusion protein). Targeting of TGF-β fusion proteins to specific tissues (cells, organs, etc.) may reduce undesirable side effects of systemic administration of such proteins, including the activity of the fusion proteins in a spectrum of tissues throughout the subject. Cell-targeting domains/proteins include, but are not limited to proteins (or domains of proteins) that bind to specific cell-surface receptors, including receptors found on only specific cell types, at specific developmental stages, under specific environmental or clinical conditions, or in particular disease states. Given the ability of TGF-β to inhibit T-cells, antigens that are specifically associated with T-cell activation might be particularly useful, including CD40 ligand and CTLA4. Each are expressed at high levels on activated T-cells, but not on the resting T-cell. More importantly the receptor for CD40 and ligand for CTLA4 have been defined and could potentially be used to target TGF-β fusion proteins to T cells. The selection of a targeting portion of a TGF-β fusion protein will be influenced by the desired target (cell, tissue, organ, etc.) to which the fusion is intended to bind; one of ordinary skill in the relevant are will know which targeting portions are appropriate for directing the fusion to specific targets. Targeting portions of the subject fusions can serve additional purposes (provide additional functions) within the same fusion protein, for instance identification (e.g., through an epitope of the targeting portion, or an increase in molecular weight) and/or purification of the fusion.

The functionalizing portion of fusions also can be a protein or domain that has a function independent of tagging or targeting, for instance an enzymatic, catalytic, or other biological function, or as a stabilizing influence that renders the fusion less prone to proteolysis or other removal from the system.

The choice of appropriate linker, if any linker is used, also will be influenced by the function of the two portions of the molecule, and whether these two portions can or must interact or should or can be held apart from each other. In general, a linker used in a functionalized TGF-β fusion will be of a length and secondary character sufficient to permit the functionalizing portion of the fusion to perform its function without hindering the activity of the TGF-β portion. Linkers can be a simple as a few amino acids that are included to facilitate construction of the fusion, for instance by the addition of one or more restriction endonuclease sites in the corresponding recombinant nucleic acid fusion molecule.

B. Assembly.

The construction of fusion proteins from domains of known proteins, or from whole proteins or proteins and peptides, is well known. In general, a nucleic acid molecule that encodes the desired protein and/or peptide portions are joined using genetic engineering techniques to create a single, operably linked fusion oligonucleotide. Appropriate molecular biological techniques may be found in Sambrook et al. (1989). Examples of genetically engineered multi-domain proteins, including those joined by various linkers, and those containing peptide tags, can be found in the following patent documents:

U.S. Pat. No. 5,994,104 ("Interleukin-12 fusion protein");

U.S. Pat. No. 5,981,177 ("Protein fusion method and construction");

U.S. Pat. No. 5,914,254 ("Expression of fusion polypeptides transported out of the cytoplasm without leader sequences");

U.S. Pat. No. 5,856,456 ("Linker for linked fusion polypeptides");

U.S. Pat. No. 5,767,260 ("Antigen-binding fusion proteins");

U.S. Pat. No. 5,696,237 ("Recombinant antibody-toxin fusion protein");

U.S. Pat. No. 5,587,455 ("Cytotoxic agent against specific virus infection");

U.S. Pat. No. 4,851,341 ("Immunoaffinity purification system");

U.S. Pat. No. 4,703,004 ("Synthesis of protein with an identification peptide"); and WO 98/36087 ("Immunological tolerance to HIV epitopes").

The placement of the functionalizing peptide portion within the subject fusion proteins is influenced by the activity of the functionalizing peptide portion and the need to maintain at least substantial TGF-β biological activity in the fusion. Two methods for placement of a functionalizing peptide are illustrated in the detailed examples: between the pro-region and the mature region of the TGF-β family protein portion of the fusion, and at a location within the mature TGF-β family protein portion that exhibits either low sequence conservation or amenability to insertions. Though these are not the only locations in which functionalizing peptides can be inserted, they serve as good examples, and will be used as illustrations. Other appropriate insertion locations can be identified by inserting test peptide encoding sequences (e.g., a sequence encoding the FLAG peptide) into a TGF-β construct at different locations, then assaying the resultant fusion for TGF-β biological activity and functionalizing peptide activity, using assays that are appropriate for the specific portions used to construct the fusion. The activity of TGF-β family proteins can be measured using any of various known techniques, including those method described herein (see, e.g., section V, below, and Example 2).

C. Expression.

One skilled in the art will understand that there are myriad ways to express a recombinant protein such that it can subsequently be purified. In general, an expression vector carrying the nucleic acid sequence that encodes the desired protein will be transformed into a microorganism for expression. Such microorganisms can be prokaryotic (bacteria) or eukaryotic (e.g., yeast). One appropriate species of bacteria is *Escherichia coli* (*E. coli*), which has been used extensively as a laboratory experimental expression system. A eukaryotic expression system will be preferred where the protein of interest requires eukaryote-specific post-translational modifications such as glycosylation. Also, protein can be expressed using a viral (e.g., vaccinia) based expression system.

Protein can also be expressed in animal cell tissue culture, and such a system will be appropriate where animal-specific protein modifications are desirable or required in the recombinant protein. Such expression is particularly appropriate where native assembly and export of the TGF-β fusion protein is desirable, since the activity of TGF-β family proteins is influenced by native dimerization (folding and assembly) and secretion from the cell.

The expression vector can include a sequence encoding a targeting peptide positioned in such a way as to be fused to the coding sequence of the functionalized TGF-β fusion protein. One such "targeting" peptide is the precursor region of the TGF-β protein itself, which is important in native export of the TGF-β family protein from the cell. Targeting peptides/domains included in the fusion can be in addition to another functionalizing peptide (such as a tag). Targeting domains may allow the fusion protein to be targeted to specific extra-cellular locations, or simply to be secreted from the cell, and may be removed during or soon after synthesis of the fusion protein. In addition, multiple targeting peptides can be included in a single fusion, for instance a peptide/domain that directs the fusion protein to be secreted, and another peptide/domain that directs the secreted protein to a target (cell, tissue, organ, etc.). Various appropriate prokaryotic and eukaryotic targeting peptides, and nucleic acid molecules encoding such, are known to one of ordinary skill in the art. Through the use of a eukaryotic secretion-type signal sequence, the functionalized TGF-β fusion protein can be expressed in a transgenic animal (for instance a cow, pig, or sheep) in such a manner that the fusion protein is secreted into the milk of the animal. Targeting protein portions also may be used to ensure that a transgenically expressed fusion protein is secreted into the circulatory system of the transgenic animal, thereby permitting the fusion protein to be transported to a target (cell, tissue, organ, etc.).

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter is preferred. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits are produced commercially. See, for instance, the QIAexpress™ expression system from QIAGEN (Chatsworth, Calif.) and various expression systems provided by INVITROGEN (Carlsbad, Calif.). Depending on the details provided by the manufactures, such kits can be used for production and purification of the disclosed functionalized TGF-β fusion proteins.

D. Purification.

One skilled in the art will understand that there are myriad ways to purify recombinant polypeptides, and such typical methods of protein purification may be used to purify the disclosed functionalized TGF-β fusion proteins. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused to the protein and used to facilitate polypeptide purification (e.g., in addition to another functionalizing portion of the fusion, such as a targeting domain or another tag). A specific proteolytic site, for instance a thrombin-specific digestion site, can be engineered into the protein between the tag and the remainder of the fusion to facilitate removal of the tag after purification, if such removal is desired.

Commercially produced protein expression/purification kits provide tailored protocols for the purification of proteins made using each system. See, for instance, the QIAexpress™ expression system from QIAGEN (Chatsworth, Calif.) and various expression systems provided by INVITROGEN (Carlsbad, Calif.). Where a commercial kit is employed to produce a functionalized TGF-β fusion protein, the manufacturer's purification protocol is a preferred protocol for purification of that protein. For instance, proteins expressed with an amino-terminal hexa-histidine tag can be purified by binding to nickel-nitrilotriacetic acid (Ni-NTA) metal affinity chromatography matrix (*The QIAexpressionist*, QIAGEN, 1997).

More generally, the binding specificities of either the TGF-β or a functionalizing peptide domain, or both, of the disclosed fusion protein may be exploited to facilitate specific purification of the proteins. A preferred method of performing such specific purification would be column chromatography using column resin to which a target molecule, or an appropriate epitope or fragment or domain of the target molecule, has been attached.

If the functionalized TGF-β fusion protein is produced in a secreted form, e.g. secreted into the milk of a transgenic animal, purification can be from the secreted fluid. Alternatively, purification may be unnecessary if it is appropriate to apply the fusion protein directly to the subject in the secreted fluid (e.g. milk).

V. Variation of Functionalized TGF-β Fusion Protein(s)

A. Sequence Variants

Certain functional characteristics of the fusion proteins disclosed herein lie not in the precise amino acid sequence of the proteins, but rather in the three-dimensional structure inherent in the amino acid sequences encoded by the DNA sequences. It is possible to recreate the functional characteristics of the fusion proteins or protein domains by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a functionalized TGF-β fusion protein. Such substitutions, however, may not produce functional variants of the disclosed fusion proteins if the substitutions are made at essential amino acid positions, for instance, binding-specificity essential residues within TGF-β family proteins (see, e.g., Huang et al., *J. Biol. Chem.*, 274:27754–27758, 1999), epitope-structural residues of functionalizing epitope tags, or targeting or enzymatically essential residues within other functionalizing protein portions. Thus, it is useful to assay the activity of variant fusion proteins (or the appropriate portion of the variant fusion proteins) using available protocols, including for instance those described herein.

Variant TGF-β fusion proteins include proteins that differ in amino acid sequence from the disclosed sequences, and sequence constructed from the disclosed protein portions, but that share structurally significant sequence homology with such proteins. Variation can occur in any single domain of the fusion protein (e.g. the functionalizing domain, the TGF-β family protein domain, or the linker if such is present in the fusion). Variation can also occur in more than one of such domains in any particular variant protein. Such variants may be produced by manipulating the nucleotide sequence of the, for instance a FLAG-TGF-β-encoding sequence, using standard procedures, including site-directed mutagenesis or mutagenic nucleic acid amplification (e.g., using PCR). The simplest modifications involve the substitution of one or more amino acids for amino acids having similar biochemical properties. These so-called "conservative" substitutions are likely to have minimal impact on the activity of the resultant protein, especially when made outside of the binding site of each domain. Table 1 shows amino acids that may be substituted for an original or native amino acid in a protein, and which are regarded as conservative substitutions.

TABLE 1

| Original Residue | Conservative Substitutions |
|---|---|
| Ala | ser |
| Arg | lys |
| Asn | gln; his |
| Asp | glu |

TABLE 1-continued

| Original Residue | Conservative Substitutions |
|---|---|
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein structure may be obtained by selecting one or more amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or prolie is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant TGF-β domain or fusion proteinencoding sequences may be produced by standard DNA mutagenesis techniques, for example, M13 primer mutagenesis. Details of these techniques are provided in Sambrook (Ch. 15, In *Molecular Cloning: A Laboratory Manual*, CSHL, New York, 1989). By the use of such techniques, variants may be created which differ in minor ways from native TGF-β encoding sequences (such as those encoding the proteins listed in FIG. 1). DNA molecules and nucleotide sequences which are derivatives of native TGF-β encoding sequences and that differ from such sequence by the deletion, addition, or substitution of nucleotides while still encoding a protein that has TGF-β biological activity (either of the same specificity as the original TGF-β family member, or the specificity of another family member), are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed fusion sequences. For example, because of the degeneracy of the genetic code, four nucleotide codon triplets—(GCT, GCG, GCC and GCA)—code for alanine. The coding sequence of any specific alanine residue within a subject fusion protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode a neutralizing bispecific fusion protein, but which vary from the disclosed nucleic acid sequences by virtue of the degeneracy of the genetic code.

Some variant TGF-β superfamily proteins previously have been identified or generated (see, e.g., U.S. Pat. No. 4,886,747; Yamada et al., *J. Bone Miner. Res.*, 15:415–420, 2000; Huang et al., *J. Biol. Chem.*, 274:27754–27758, 1999; Pociot et al., *J. Am. Soc. Nephrol.*, 9:2302–2307, 1998; and Wharton et al., *Genetics*, 142:493–505, 1996).

B. Peptide Modifications

The present disclosure includes biologically active molecules that mimic the action of the functionalized TGF-β fusion proteins provided herein, and specifically that maintain a TGF-β family protein activity and the desired additional functionality (e.g., targeting, recognition by a specific antibody (through an epitope), ease of purification, enzymatic functionality, and so forth) depending on the functionalizing portion that is fused to the TGF-β portion. The proteins of the disclosure include synthetic embodiments of fusion proteins described herein, as well as analogues molecules (non-peptide organic molecules), derivatives (chemically functionalized protein molecules obtained starting with the disclosed peptide sequences) and variants (homologs) of these proteins that specifically maintain at least one TGF-β specific biological activity (e.g., binding to a specific TGF-β receptor) and at least one additional function provided by the "functionalizing" portion of the fusion (which function will be dependent on the portion chosen). Each protein of the disclosure is comprised of a sequence of amino acids, which may be either L- and/or D-amino acids, naturally occurring and otherwise.

Proteins may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_6$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, malcic, tartaric and other organic salts, or may be modified to $C_1$–$C_{16}$ alkyl or dialkyl amino or further converted to an amide.

Hydroxyl groups of the protein side chains may be converted to $C_1$–$C_{16}$ alkoxy or to a $C_1$–$C_{16}$ ester using well-recognized techniques. Phenyl and phenolic rings of the protein side chains may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the protein side chains can be extended to homologous $C_2$–$C_4$ alkylenes. Thiols can be protected with any one of a number of well-recognized protecting groups, such as acetamide groups. Those skilled in the art will also recognize methods for introducing cyclic structures into the proteins provided herein to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three-dimensional arrangement of the protein backbone and component amino acid side chains in a functionalized TGF-β fusion protein, resulting in such peptido- and organomimetics of the proteins of this disclosure having at least one TGF-β biological activity and an additional function (conveyed by the "functionalizing" portion of the molecule, such as a tag or targeting portion, as discussed herein). For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165–174 and Principles of pharmacology Munson (ed.) 1995, Ch. 102, for descriptions of techniques used in CADD. Also included within the scope of the disclosure are mimetics prepared using such techniques that produce biologically active, functionalized TGF-β fusion proteins.

C. Domain Length Variation.

It will be appreciated that the protein/peptide domains of the current disclosure may be combined to produce fusion protein molecules without necessarily splicing the components in the same place. It is believed to be possible to use shorter or longer fragments of each component domain. Such variation in length can be caused by the inclusion of longer or short functionalizing portions in the fusion, including for instance a linker portion. It is, however, in some instances not beneficial to use so short a portion of a tag or targeting peptide that the tag or targeting peptide is no longer functional (and therefore cannot provide an additional function to the fusion protein).

D. Functionalizing Peptide Location in the Fusion.

The placement of the functionalizing peptide portion within the subject fusion proteins is influenced by the activity of the functionalizing peptide portion and the need to maintain at least substantial TGF-β biological activity in the fusion (as described herein). However, within these limitations, variants of the described functionalized TGF-β fusion molecules can be constructed by altering the placement of the functionalizing peptide. Such variants include moving the peptide insertion point a few (e.g., one to about 10) amino acid residues towards the amino-or carboxy-terminal end of the fusion protein (e.g., inserting a FLAG or other tag between residues 12 and 13 instead of 11 and 12 of TGF-β1, or between residues 21 and 22, or between residues 10 and 11, for instance). Likewise, a peptide tag could be inserted between any pair of adjacent residues between about residue 1 and about residue 22 of the mature portion of a TGF-β family protein. In some specific examples, such insertion within the TGF-β family protein is accompanied by the removal of one or more of the TGF-β family protein amino acid residues. For instance, an peptide tag (such as the FLAG tag) could be inserted between residues 10 and 12, replacing residue 11 of the TGF-β family protein.

VI. Activity of Functionalized TGF-β Family Fusion Proteins

It is important to assess the chemical, physical and biological activity of the disclosed fusion proteins. Among other uses, such assays permit optimization of the domains chosen, optimization of the placement of the functionalizing portion within the fusion protein, optimization of the length and conformation of the linkers used to connect portions of the fusion, and determination of the effect(s) of variant amino acid changes in the fusion proteins. Appropriate control molecules can be included in each activity assay. Such controls molecules can include individual domains used to construct the fusion (e.g., a part or all of the mature or precursor TGF-β family protein), composite domains expressed as separate molecules and mixed in the reaction, for instance in a 1:1 molar ratio, or fusions that include only one portion of the functionalized TGF-β fusion coupled to another protein or peptide (e.g., a different tag on the same TGF-β protein, or the same tag on a different subject protein, either another member of the TGF-β family or another protein).

A. TGF-β Family Protein Activity

The biological activity of a TGF-β family protein portion of a subject fusion protein can be assayed using any various different known TGF-β activity assays, including those described in detail herein. TGF-β biological activities that may be displayed by the subject fusion proteins include, but are not limited to, activities linked to the mature region of the protein (e.g., binding to one or more cell surface receptors, mediation of a cellular response, etc.) and activities linked to the TGF-β pro-region (e.g., secondary folding and tertiary assembly of the TGF-β homodimer, processing, secretion from the cell, etc.). Each of these functions can be measured in a fusion protein, either alone or in some instances in combination.

Binding of a TGF-β fusion protein can be measured in competitive binding assays (as described herein and elsewhere, e.g., in Qian et al., *J. Biol. Chem.*, 271:30656–30662, 1996; The activity of the mature region of a TGF-β protein (including the TGF-β fusions of this disclosure) also can be measured by assaying one or more downstream effects of the protein in a biological system. Such effects include phosphorylation of one or more smad proteins (such as smad2, as described below), and growth inhibition (e.g., inhibition of CCL64 mink lung epithelial cells, as described below). Other assays for TGF-β activities are described, for instance, in Gray and Mason, *Science*, 247:1328–1330, 1990; Tuan et al., *Conn. Tiss. Res.*, 34:1–9, 1996; Wakefield et al., *Growth Factors*, 5:243–253, 1991; Danielpour and Roberts, *J. Immunol Methods* 180:265–272, 1995; Danielpour, *J. Immunol Methods*. 158:17–25, 1993; Danielpour et al., *Growth Factors* 2:61–71, 1989; Randall el al., *Immunol. Methods* 164:61–67, 1993; Danielpour et al., *J. Cell Physiol.* 138:79–86, 1989.

The pro-region is important for correct folding, assembly, and secretion of a TGF-β protein; thus, activity of a pro-region that is included in a fusion protein of this disclosure can be measured by assaying for these functions of the fusion protein. Pro-region activity has been examined previously (see, e.g., Dubois et al., *J. Biol. Chem.*, 270:10618–10624,1995; Gray and Mason, *Science*, 247:1328–1330, 1990; Murphy-Ullrich and Poczatek, *Cytokine Growth Factor Rev.* 11:59–69,2000; Barcellos-Hoff, *J. Mammary Gland Biol. Neoplasia* 1:353–363, 1996; Hellmich et al., Metabolism 49:353–359, 2000; Saharinen el al., *Cytokine Growth Factor Rev.*, 10:99–117, 1999, and the methods described in these references are appropriate for measuring the activity of a pro-region in the subject fusions.

B. Activity of a Functionalizing Peptide

The biological activity of a functionalizing peptide that is fused to a TGF-β protein portion to form a fusion can be assayed independently of the TGF-β biological activity(s) of the fusion. The appropriate assay(s) for measuring functionalizing peptide activity will be dictated largely by the functionalizing peptide.

The functionality of an epitope tag can be tested by detecting the fusion protein using an antibody (or antibody derivative) known to bind to the epitope, for instance in an immunoblot ("western"), ELISA, or other assay system; such techniques are well known. Other identification tags can be tested for functionality based on their intended method of identification—e.g., based on differential mobility or other added function. The functionality of a purification tag can be tested by using it to purify the fusion protein, for instance using column chromatography or other conventional techniques.

The effective functionality of a targeting domain within a fusion protein can be tested by examining the targeting of the fusion protein in an experimental or clinical system. Such targeting can be examined using conventional techniques, for instance fractionation, in situ hybridization, or through cell or tissue-specific biological effects that result from the targeting of the fusion protein (e.g., TGF-β mediated effects caused by the delivery of the fusion protein).

Other passenger proteins can be assayed based on the native or expected function of the passenger protein. Assays appropriate for any particular passenger protein will be specific to that passenger, and will be known to those of ordinary skill in the art.

VII. Incorporation of Fusion Proteins into Pharmaceutical Compositions

Pharmaceutical compositions that comprise at least one functionalized TGF-β fusion protein as described herein as an active ingredient will normally be formulated with an appropriate solid or liquid carrier, depending upon the particular mode of administration chosen. The pharmaceutically acceptable carriers and excipients useful with compositions in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, for instance anti-proliferative agents, anti-infectives, or anti-cancer agents, also may be included.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutical compositions that comprise functionalized TGF-β fusion protein(s) can be formulated in unit dosage form, suitable for individual administration of precise dosages. Possible unit dosages may contain, for instance, approximately 1.0 µg to approximately 100 µg of protein. The amount of active compound administered will be dependent on the subject being treated, the severity of the affliction, and the manner of administration, and is best left to the judgment of the prescribing clinician. Within these bounds, the formulation to be administered will contain a quantity of the active component(s) in an amount effective to achieve the desired effect in the subject being treated.

VIII. Uses of Functionalized TGF-β Fusion Proteins

The functionalized TGF-β fusion proteins described herein can be used in a number of systems in place of native TGF-β molecules, including: (1) detection of tagged ligand in transfected cells; (2) detection of cell surface expression of TGF-β receptor complexes by flow cytometry; and (3) measurement of cell surface levels of receptor complexes in non-radioactive cross-linking assays. The functionalized TGF-β fusion proteins are safer, faster and cheaper alternatives to the use of [$^{125}$I] radiolabeled TGF-β molecules and expands the repertoire of techniques that can be used to look at TGF-β receptor expression levels.

Because the subject functionalized TGF-β fusion proteins can be distinguished from native TGF-β, a clinically/experimentally administered, functionalized TGF-β molecule can be traced within a subject or experimental system. This permits determination of the distribution (cellular, tissue, etc.), half-life, elimination, and circulating levels of the administered protein, as differentiated from any endogenous TGF-β, permitting the clinician to more finely tune dosages and administration regimes.

The tagged protein also can be used to study TGF-β receptor expression levels, for instance in different tissues or at different times (e.g., after different clinical or experimental treatments). In addition to being useful in prognosis and diagnosis of disease states (see below), this makes the fusion proteins useful for testing possible drug or other therapeutic treatments, or other regimens that might intentionally or unintentionally alter the expression level (or stability) of a TGF-β receptor.

In the clinic, trials employing a TGF-β family protein (such as TGF-β1) to look at amelioration of disease symptoms in, for instance, arthritis, multiple sclerosis, colitis or in other diseases, can now use a functionalized TGF-β fusion protein (such as FLAG-TGF-β1). This allows the clinician to follow bio-availability of the TGF-β family ligand and to accurately quantify the level that is exogenously administered.

The functionalized TGF-β fusion proteins provided herein may be administered to humans, or other animals on whose cells they are effective, in various manners such as topically, orally, intravenously, intramuscularly, intraperitoneally, intranasally, intradermally, intrathecally, and subcutaneously. The particular mode of administration and the dosage regimen will be selected by the attending clinician, taking into account the particulars of the case (e.g., the subject, the disease, the disease state involved, and whether the treatment is prophylactic or post-infection). Treatment may involve daily or multi-daily doses of fusion protein(s) over a period of a few days to months, or even years.

If treatment is through the direct administration of cells expressing the functionalized TGF-β fusion protein to the subject, such cells (e.g. transgenic pluripotent or hematopoietic stem cells or B cells) may be administered at a dose of between about $10^6$ and $10^{10}$ cells, on one or several occasions. The appropriate number of cells will depend on the patient, as well as the fusion protein and cells chosen to express the protein.

A general strategy for transferring genes into donor cells is disclosed in U.S. Pat. No. 5,529,774. Generally, a gene encoding a protein having therapeutically desired effects is cloned into a viral expression vector, and that vector is then introduced into the target organism. The virus infects the cells, and produces the protein sequence in vivo, where it has its desired therapeutic effect. See, for example, Zabner et al., Cell 75:207–216, 1993. As an alternative to adding the sequences encoding the functionalized TGF-β fusion protein or a homologous protein to the DNA of a virus, it is also possible to introduce such a gene into the somatic DNA of infected or uninfected cells, by methods that are well known in the art (Sambrook et al. (In Molecular Cloning. *A Laboratory Manual*, CSHL, New York, 1989). These methods can be used to introduce the herein disclosed fusion proteins to human cells to provide long-term production of the fusion protein.

Fusion proteins disclosed herein can be used for the detection of TGF-β receptor expression in tissues or cells of patients with cancer and immune disorders. In this instance, the ability of the epitope-tagged ligand to bind to receptors on fresh specimens or fixed tissues can be coupled with quantitative analysis of cell-bound epitope tag. This can be accomplished either by direct visualization with immunohistochemical analyses, or through the use of Fluorescence Activated Cell Sorting (FACS) to detect the presence of a fluorochrome-antibody conjugate raised specifically to the epitope tag.

The presence of an epitope tag in functional TGF-β fusion proteins will allow for accurate assessment of the delivery, distribution, and elimination following systemic, topical, or enteral administration of the fusion TGF-β protein. This is impossible to do with the native protein, as the production of TGF-β via the endogenous gene cannot be distinguished from the administered exogenous protein. Thus, this fusion protein will provide a handle for an unambiguous assessment of the pharmacodynamics of TGFβ in the setting of clinical trials. This is also an important consideration for any future gene therapy approaches based on the delivery of a TGF-β expression system. The use of a tagged TGF-β in such vectors will allow one to follow production, both local and systemic, in a quantitative fashion, over time. Examples of specific applications include:

6651—topical therapy of cutaneous wounds for the acceleration of wound healing;
  6652—topical application to oral mucosa to prevent chemotherapy-induced mucositis;
  6653—systemic administration of TGF-β to prevent chemotherapy-induced myelosuppression;
  6654—aerosolized administration of TGF-β for the treatment of reactive airway diseases such as allergen-induced asthma;
  6655—topical treatment of inflammatory dermatitis;
  6656—intranasal administration of cDNA expression vector encoding FLAG-TGF-β for the prevention and/or treatment of colitis (Kitani, et al., *J. Exp. Med.* 192:41–52, 2000).

IX. Experimental Animal Systems

The teaching of adding a functionalizing peptide or protein or peptide portion to a functional TGF-β family protein now makes it possible to engineer TGF-β family protein "knock-ins" to examine whether a specific TGF-β (e.g., TGF-β1) can rescue the phenotype of TGF-β specific "knock-out" mice (such as TGF-β2 or TGF-β3 knock-outs) without the complications caused by cross reactivity of species-specific or isoform-specific antibodies.

The essential question that "knock-in" studies aim to address is whether there is substantial redundancy between the individual isoforms of the TGF-β family expressed in mammals. While they have a great deal of similarity at the amino acid level, it is not clear whether one isoform can sufficiently replace the other in vivo or can compensate for the absence of another in vivo. To determine this, we can now replace each TGF-β locus with either the same isoform or with one of the immediate or distant family members with the epitope tag inserted. The tag allows identification of when and where the specific cytokine is expressed. More importantly, we can determine whether (for example) TGF-β2, when expressed where and when TGF-β1 is normally expressed, can exert the appropriate functions necessary to maintain homeostasis.

X. Diagnosis and Prognosis

The development and/or progression of many pathologic conditions, including cancer and immune disorders, is often associated with loss of expression of TGF-β family protein receptors. The functionalized fusion proteins of the disclosure provide tools for quantitative, real-time measurement of receptor expression in tissues and cells by virtue of the ability of these fusions to bind to TGF-β receptors, and be identified (e.g., by the presence of an epitope tag or other identifiable protein or peptide portion). These molecules can be used to diagnose and/or determine progression of diseases associated with receptor loss.

Specific examples of diseases or other pathologic conditions that can be diagnosed or prognosed using the subject fusions proteins include: cancer (see Reiss, *Microb. Infect.*, 1:1327–1347, 1999; De Caestecker et al., *J. Nat'l Cancer Inst.* 92:1388–1402, 2000; Kim et al., Cyto. *Growth Factor Rev.* 11:159–169, 2000; and Taketo et al., Cyto. *Growth Factor Rev.* 11:147–159,2000); sound healing (Ashcroft and Roberts, Cyto. *Growth Factor Rev.* 11:125–133, 2000; Roberts and Sporn, "Transforming growth factor-β." In: *The molecular and cellular biology of wound repair*. Clark (Ed.), New York: Plenum Press,.p275–308, 1996; and Beck et al., *J. Clin. Invest.* 92:2841–2849; 1993); atherosclerosis (McCaffery, Cyto. *Growth Factor Rev.* 11:103–114, 2000); kidney disease (Sharma and McGowan, Cyto. *Growth Factor Rev.* 11:115–125, 2000); and hereditary hemorrhagic telangiectasia (Johnson et al., *Nat. Genetics* 13:189–195, 1996; and McAllister, et al., *Nat. Genetics* 8:345–351, 1994). More generally, see Blobe et al. (NEJM 342:1350–1358, 2000).

In each of these situations, an appropriate functionalized (e.g., epitope tagged) TGF-β fusion protein can be applied to a cell sample from a subject, and the amount of binding of the fusion protein to the target TGF-β receptor can be determined and compared to the amount found in a control sample. The level of ligand binding to the receptor is indicative of the level of the receptor in that sample. An altered receptor level (such as a reduced receptor level) is indicative of the indicated associated disease or pathologic condition.

XI. Kits

Kits are provided that contain at least one functionalized TGF-β fusion protein, or a nucleic acid molecule (e.g., a vector) that encodes such a protein, or both, in one or more contains. The provided kits may also include written instructions. The instructions can provide calibration curves or charts to compare with the determined (e.g., experimentally measured) values. Included are kits that can be used for diagnosis or prognosis of a disease or other condition associated with a change (decrease or increase) in the level of cell surface expression of a TGF-β receptor.

The invention is further illustrated by the following non-limiting Examples.

EXAMPLES

Example 1

Construction and Expression of FLAG-TGF-β1 and 11/12FLAG-TGF-β1

This example describes the construction and expression of two biologically functional TGF-β fusion proteins, each comprising the FLAG epitope tag near the N-terminus of the mature TGF-β protein. The disclosed epitope-tagged TGF-β differs fundamentally from earlier attempts to tag TGF-β in that the inventors have succeeded in expressing epitope-tagged biologically active TGF-β in a mammalian host.

Expression of the FLAG-TGF-β fusions described in this example is driven by the human elongation factor 1-alpha (EF1-α) gene promoter, a strong promoter capable of driving expression in virtually any type of cell. Two FLAG-tagged TGF-β1 constructs, differing only in the location of insertion of the FLAG tag, are described. In one, the FLAG tag is inserted immediately following the cleavage site (N-terminal in the mature, processed TGF-β1 molecule). In the second construct, FLAG is inserted between amino acids 11 and 12 of the mature TGF-β1 molecule. Each plasmid has successfully been transfected into mammalian cells, and the FLAG-TGF-β1 protein product is detectable in cell culture supernatants using sandwich ELISA and western blots (with antibodies raised against either the FLAG epitope tag or TGF-β1). Cells transfected with the fusions described in this example secrete biologically active TGF-β1 as measured by a number of different methods (see below).

Construction of FLAG-tagged TGF-β1.

The FLAG epitope tag was introduced into the FLAG-β1 sequence using a 2-step PCR mutagenesis technique. Flanking primers were:

(5'-primer) 5'-ggagagatctggtaccgagatggcgcct-3 (SEQ ID NO: 1); and (3'-primer) 5'-ataagaattgcggccgctaatcgatcccaagtgggcttgg-3' (SEQ ID NO: 2).

Two sets of FLAG mutagenesis primers were used. For constructing the N-terminally tagged-TGF-β1, the following primers were employed:

(5'-primer)
5'-gactacaaggatgacgacgacaaggccctggataccaactactgcttc-3' (SEQ ID NO: 3); and (3'-primer)
5'-cttgtcgtcgtcatccttgtagtctcggcggtgccgggagctgtg-3' (SEQ ID NO: 4).

For the insertion of FLAG between amino acids 11 and 12 of the mature TGF-β1 peptide, the following mutagenesis primers were used:

(5'-primer)
5'-gactacaaggatgacgacgacaggagaagaactgctgcgtgcggc-3' (SEQ ID NO: 5);

(3'-primer)
5'-cttgtcgtcgtcatccttgtagtctcggcggtgccgggagctgtg-3' (SEQ ID NO: 6).

The PCR template was full length active porcine TGF-β1, where two cysteine residues at 223 and 225 in the LAP portion of the molecule have been mutated to serines, disrupting two disulfide bonds that form between LAP and TGF-β1 (and which keep TGF-β1 in a latent form), and where the second residue has been changed from a proline to an alanine to improve translation. The final PCR products had 5'-Bgl II and 3'-Not I restriction sites. The PCR products were purified away from the primers using a QIAquick Gel Extraction kit (QIAGEN, Valencia, Calif.) after separation on an agarose gel. Purified PCR products were digested overnight and purified using a QIAGEN QIAquick PCR Purification kit prior to ligation into BamHI, NotI digested, gel purified pEBB vector (Mayer et al., *Curr. Biol.*, 5:296–305, 1995; provided by Colin Duckett, NIH). This vector contained the human elongation factor-1α promoter, which drives expression of the cloned cDNA.

Transfection of Cos1 Cells.

Cos1 cells were transiently transfected with each of the following: (1) pEBB vector alone; (2) WT (active) TGF-β1 in pEBB (WT); (3) N-terminally FLAG-tagged TGF-β1 (NFLAGβ); and (4) TGF-β1 with FLAG inserted between amino acids 11 and 12 of the mature TGF-β1 peptide (11/12FLAG-β). Two micrograms of plasmid were transfected into cos 1 cells in serun-free DMEM medium (Life Technologies, Rockville, Md.) containing ITS+ supplement (Collaborative Biomedical Products, Bedford, Mass.) in 10 cm dishes using the Fugene 6 reagent and manufacturer's protocol (Roche, Indianapolis, Ind.). The total volume of media in each 10 cm dish was 5 mL. Supernatants were collected after 48 hours, and any contaminating cells were removed by brief centrifugation before storing supernatants at −80° C.

a Sandwich ELISA for Active TGF-β1.

Levels of active TGF-β1 were quantified using a Quantikine TGF-β1 sandwich ELISA kit from R&D Systems (Minneapolis, Minn.) following the instructions provided by the manufacturer.

Antibodies and Western Blots.

All western blots were performed using Novex Tris-Glycine gels and the Novex blotting system (Novex, San Diego, Calif.). Protein was transferred onto nitrocellulose membranes, blocked with blocking buffer (TBST+4% BSA) and incubated with the indicated antibodies in blocking buffer overnight at 4° C. Secondary antibodies were conjugated to horseradish peroxidase (HRP) and purchased from Jackson Immunobiology. TGF-β1 protein levels were measured using a rabbit polyclonal antibody (Cat. # G1221) purchased from Promega (Madison, Wis.). The anti-FLAG monoclonal antibody (M2) was purchased from Upstate Biotechnology (Waltham, Mass.). The anti-smad2 antibody was purchased from Zymed (Cat # 51-1300, San Francisco, Calif.); and the anti-phospho-smad2 antibody was purchased from Upstate Biotechnology (Cat # 06-829).

Design of FLAG-tagged TGF-β.

Figure 2A:
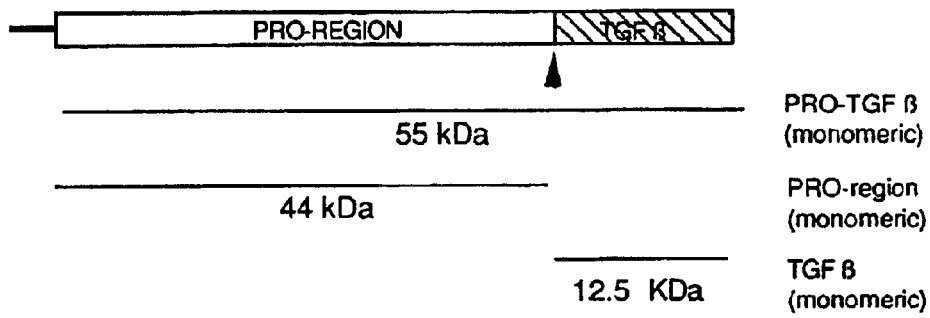
FIG. 2 is a series of schematic drawings depicting (FIG. 2A) the structure of a native generic TGF-β protein, and (FIG. 2B) the design of two examples of functionalized TGF-β fusion proteins, NFLAG and 11/12FLAG, showing the points of insertion of the FLAG tag.
Figure 2B:
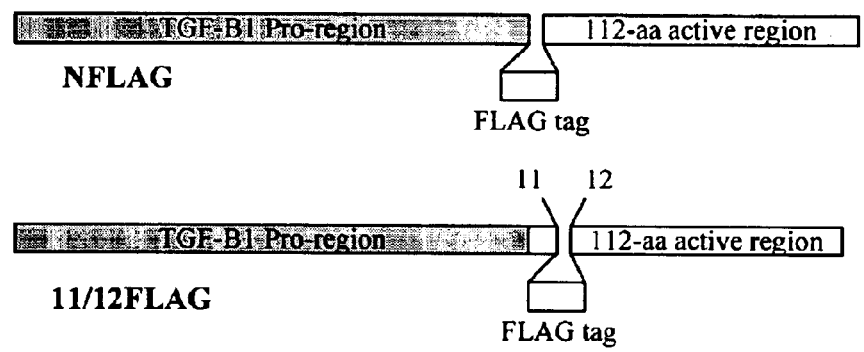
Figure 3A:
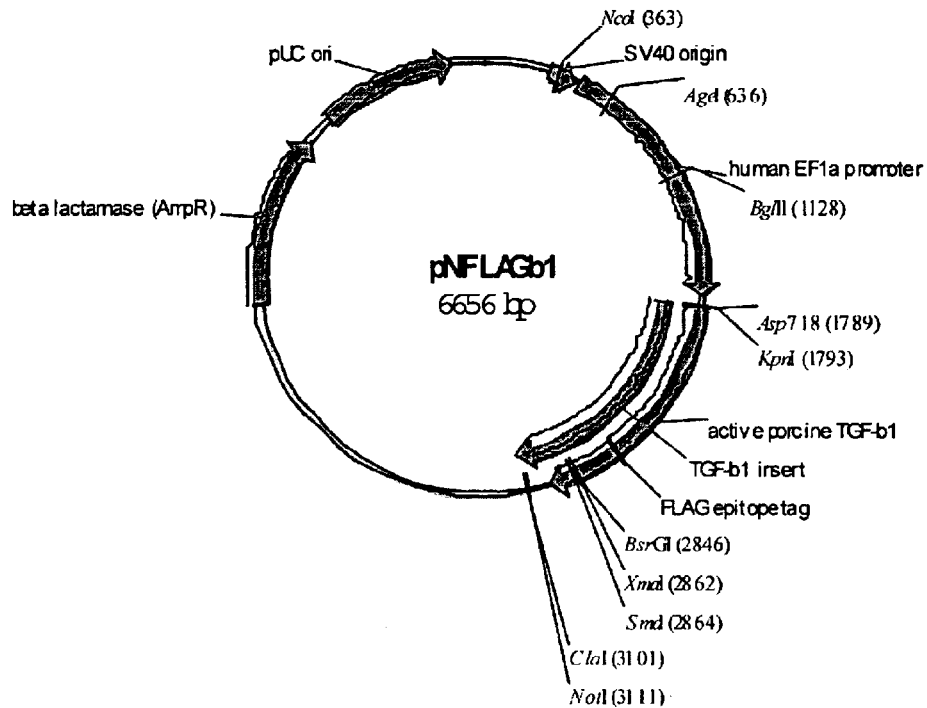
FIG. 3 shows the graphical maps of plasmids encoding the NFLAG and 11/12FLAG fusions. The respective plasmids pNFLAGb1 (FIG. 3A) and p11/12FLABb1 (FIG. 3B) are derived from the pEBB plasmid (Mayer et al., *Curr. Biol.*, 5:296–305, 1995).
Figure 3B:
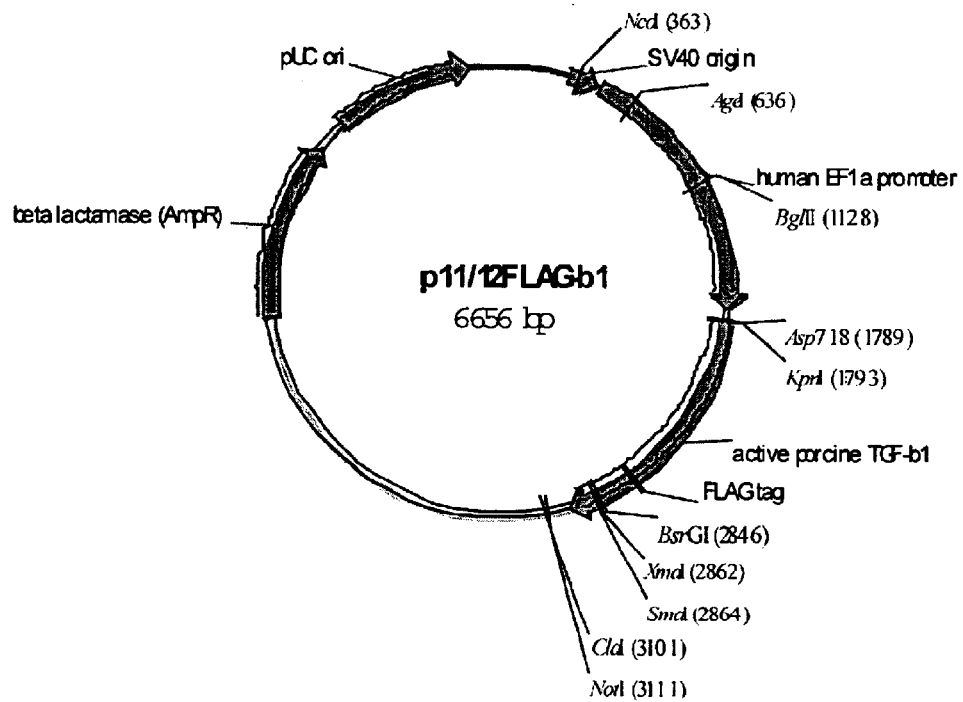

The FLAG tag was inserted into two positions (FIG. 2B) in different fusion constructs. In the first, FLAG was inserted immediately following the proteolytic cleavage site, which would make the tag N-terminal in the mature, processed TGF-β1 molecule. In the second construct, FLAG was inserted between amino acids 11 and 12 of the mature TGF-β peptide. This site was selected because, in one TGF-β family member, TGF-β4, there is an insertion of an additional two amino acids—a phenomenon that does not affect biological activity of the native molecule.

FLAG-tagged TGF-β1is Processed and Secreted

Sandwich ELISA (SELISA) revealed that cells transfected with un-tagged TGF-β1 (WT) secreted large amounts of the ligand into the medium (FIG. 4A). Less ligand was secreted in the case of the NFLAG construct although the levels (5 ng/ml) are well in excess or the minimum concentration of ligand needed to inhibit cell growth (10–15 pg/mL). In the case of the 11/12FLAG construct, SELISA was unable to detect secreted TGF-β1. It is possible that insertion of the FLAG sequence delays or impairs the production and/or secretion of TGF-β1. However, we cannot rule out differences in transfection efficiencies at this time. Western blot analysis revealed that the un-tagged TGF-β1 (WT) was indeed expressed to higher levels than were the FLAG-tagged constructs (FIG. 4B). However, significant levels of both the NFLAG and 11/12FLAG proteins were secreted into the medium as revealed with both the anti-TGF-β1 antibody (panel A) and the anti-FLAG antibody (panel B). Consistent with the SELISA findings, levels of NFLAG-β1 were higher than those of 11/12FLAG-β1. Interestingly, the accumulation of the lower molecular weight, mature cleaved TGF-β1 was lower in the case of cells transfected with NFLAG-β1 than in cells transfected with the 11/12FLAG-β1 or WT constructs. It is possible that insertion of the FLAG sequence, which carries a strong net negative charge, interferes with cleavage of the pro-protein after the two positively charged arginine residues.

Example 2

Biological Activity of FLAG-TGF-β1 and 11/12FLAG-TGF-β1

This example provides assays that can be used to test the biological activity of TGF-β fusion molecules. In particular, this example demonstrates that representative functionalized TGF-β fusion proteins have TGF-β biological activity at least as great as native TGF-β, in spite of the addition of the FLAG epitope tag. Biological activity is demonstrated by two independent methods: (1) growth inhibition of CCL64 cells; and (2) phosphorylation of smad 2 in NMuMG cells.

Smad2 Phosphorylation Studies.

NmuMG cells were plated in 60-cm dishes, incubated in medium containing 0.5% FBS for three hours. COS cell supernatants from cells transfected with various TGF-β1 plasmids were added to these cells (after first washing extensively with PBS). The cells were then incubated with the supernatants for 30 minutes. Cells were washed with PBS and scraped off the dishes. Cell pellets were dissolved in NP-40 lysis buffer containing 50 mM Tris-Cl pH 7.4, 150 mM NaCl, 50 mm NaF, 0.5% NP-40, 1 mM Dr, 1 mM sodium orthovanadate plus proteinase inhibitors (proteinase inhibitor cocktail tablets, one tablet per 10 mL buffer-Boehringer-Mannheim, Cat # 1836153, Indianapolis, Ind.). Thirty micrograms of total protein were applied to each lane of a 10% Novex Tris-Glycine gel.

Growth Inhibition Assays.

CCL64 mink lung epithelial cells were plated onto 6-well plates. Various dilutions of recombinant human TGF-β1 standard or transfected Cos cell supernatants were added to the wells. CCL64 cells were pulsed for two hours with $^3$H-thymidine, after 48 hours of incubation with TGF-β standard or conditioned medium. Cells were trypsinized and harvested using a cell harvester and [$^3$H] counts measured as described previously.

FLAG-tagged TGF-β1 Retains Full Biological Activity

Supernatants from transfected COS cells were evaluated for biological activity by the ability to inhibit growth of and mink lung epithelial cell line, CCL64. Addition of recombinant human TGF-β1 to these cells revealed that maximal inhibition was observed at about 35 pg/mL (~97 pg/mL for WT); 50% inhibition was observed at about 2.4 pg/mL (~19 pg/mL for WT). Comparison of the supernatants from COS cells transfected with WT (un-tagged), NFLAG and 11/12 FLAG revealed that the FLAG-tagged ligands were at least as efficient as the wild type molecule in inhibiting cell growth (FIG. 5).

Exposure of cells to TGF-β1 leads to rapid and transient phosphorylation of smad 2 and smad 3. As a biochemical assay to measure TGF-β1 activity, we looked at levels of smad 2 phosphorylation. NMuMG cells were treated with supernatants from transfected COS cells. After 30 minutes, the cells were washed extensively with PBS, scraped off the plates and the cell pellets were lysed in NP-40 lysis buffer. Smad 2 phosphorylation and total smad 2 level were examined by western blot analysis (FIG. 4B, panel C). NMuMG cells incubated with supernatants from untransfected COS cells or from Cos cells transfected with vector alone (pEBB) showed no elevation in phosphorylated smad 2. However, cells incubated with supernatants from COS cells transfected with WT-TGF-β1, NFLAG-β1 and 11/12FLAG-β1 all showed significant elevations in the amount of smad 2 phosphorylated (FIG. 4B, panel C). Comparison of total smad 2 levels showed no significant differences between the samples. Thus, using two independent assays, one biological and the second biochemical, it is herein demonstrated that insertion of the FLAG epitope tag does not lead to significant loss of activity.

Example 3

Use of FLAG-TGF-β1 and 11/12FLAG-TGF-β1 in Experimental Systems.

This example demonstrates that the functionalizing peptide portion of the subject fusion proteins is functional in biological and test systems. FLAG-TGF-β1 has been successfully used in a number of different assays. FLAG-TGF-β1 was used to (1) detect expression of tagged ligand in transfected cells; (2) detect cell surface expression of TGF-β receptor complexes by flow cytometry; and (3) measure cell surface levels of receptor complexes in a non-radioactive cross-linking assay. The tagged ligand is a safer, faster and cheaper alternative to the use of [$^{125}$I] radiolabeled TGF-β1 ligand and expands the repertoire of techniques that can be used to look at TGF-β receptor expression levels.

A. Flow Cytometry: Detection of receptor Molecule TβRI Using FLAG-TGF-β1

Cells were incubated with FLAG-TGF-β1 in FACS buffer. Next, cells were incubated with a FITC-conjugated goat anti-mouse secondary antibody. This approach demonstrated that cell surface expression of TGF-β type II/type I receptor complexes was detectable using the subject fusion proteins.

B. Immunocytochemistry: Detection of FLAG-tagged TGF-β1

COS cells were transiently transfected with FLAG-tagged TGF-β1 for 24 hours. Cells were then washed extensively with PBS and then fixed with buffered paraformaldehyde. Anti-TGF-β1 or anti-FLAG monoclonal antibody was used, followed by a secondary goat anti-mouse antibody conjugated to FITC, to detect intracellular expression FLAG-TGF-β1 (FIG. 4A, panels A and B respectively). The results clearly show that both epitope-tagged TGF-β fusion molecules easily can be detected in over-expressing cells.

C. Quantification of TGF-β Receptor Cell Surface Expression.

Cross-linking studies aimed at detecting cell surface expression of TGF-β receptors typically employ [$^{125}$I]-labeled TGF-β1. As a safer and more economical alternative, FLAG-TGF-β1 was examined to determine if it could be used in cross-linking assays. Cells were incubated with FLAG-TGF-β1 in either the absence or presence of an excess of un-tagged TGF-β1 ligand and cross-linking was performed as previously described using DSS (Cheifetz et al., *J. Bio. Chem.*, 261:9972–9978, 1986). Clarified cell lysates were first immunoprecipitated with a rabbit polyclonal antibody against the TGFP type II receptor (TβRII) (C-16, Santa Cruz). After extensive washing of the immune complexes, the samples were resuspended in 1X Laemmli buffer and resolved on a Novex 10% Tris-glycine gel. The blot was then probed with an anti-FLAG monoclonal antibody. Both FLAG-TGF-51 ligands were effective in detecting cell surface TGF-β type I and type II receptor complexes. Detection of these complexes was abrogated by the addition of a 10-fold molar excess of un-tagged ligand. Film exposure times were in the range of two to four seconds, making this method of detection much faster than methods employing radiolabeled ligand, which typically takes up to two weeks to develop.

Example 4

Additional Fusion Constructs

Additional functionalized TGF-β fusion proteins have been constructed using different TGF-β isoforms (e.g., TGF-β2 and TGF-β3) and different functionalizing peptide portions (e.g., haemagglutanin (HA) and Green Fluorescent protein (GFP)), as well as placing the tag in slightly different positions than at the N-terminus or between residues 11 and 12. In particular examples of such fusion constructs, the tag has been introduced between amino acid 5 and 6 of mature TGF-β1, or optionally at the front of the mature protein with a short amino acid sequence (e.g., ten or fewer, for instance five amino acids) from the mature TGF-β family protein duplicated before the functionalizing peptide.

This example provides descriptions of some of the preparation and/or characterization of additional fusion constructs.

Methods and Materials:

Construction of Fusion Protein Constructs: For construction of the plasmid containing the N+5FLAG TGF-β1 (N+5FLAG-⊕1) construct (SEQ ID NO: 16), the following mutagenesis primers were used:

(forward)
5'-gccctggataccaacgactacaaggatgacgacgacaaggccctgg-ataccaactactgcttcag-ctccacgg-3' (SEQ ID NO: 18);

(reverse)
5'-cttgtcgtcgtcatccttgtagtcgttatccagggctcggcggtggtgcc-gggagctgtgcaggt-gctgggc-3' (SEQ ID NO: 19).

For construction of the plasmid containing the N+5HA-TGF-β1 (N+5HA-β1) construct (SEQ ID NO: 20), the following primer pairs were used:

(forward:
5'-gccctggataccaacagctacccatacgacgtgccagactacgcatct-ctggccctggataccaact-actgcttcagctccacggagaagaactgctgcgtgcggcag-3' (SEQ ID NO: 22);

(reverse)
5'-cagagatgcgtagtctggcacgtcgtatgggtagctgttggtatccagg-gctcggcggtgccggga-gctgtgc-3' (SEQ ID NO: 23).

The same pair of flanking primers as those employed for construction of the N-FLAG-β1 construct (Example 1) was used. The gel purified PCR products were cloned into the mammalian expression vector pEF6-V5/His-TOPO (In Vitrogen, Carlsbad, Calif.). The presence of a stop codon in the porcine cDNA ensured that the c-terminal V5 and 6x His tags in the vector were not translated.

Transfection of Cos1 cells. Cos1 cells were transiently transfected with pEBB or pEF6V5/His-TOPO vector alone; WT (active) TGF-β1 in pEBB or PEF6-V5/His-TOPO (WT); N-terminally FLAG-tagged TGF-β1 (NFLAGβ); N+5FLAG-TGFβ1; or N+5 HA-TGFβ1. Two micrograms of plasmid were transfected into Cos1 cells in serum-free DMEM medium containing ITS+ supplement (Collaborative Biomedical Products) in 10 cm dishes using the Fugene 6 reagent and manufacturer's protocol (Roche). The total volume of media in each 10 cm dish was 5 mL. Supernatants were collected after 48 hours, and any contaminating cells were removed by brief centrifugation before storing supernatants at −80° C.

Sandwich ELISA for active epitope-tagged TGF-β1. Levels of FLAG- and HA-tagged TGF-β1 were measured using a sandwich ELISA. A flat 96-well plate (Falcon) was used; each well was coated with 50 µl of the first antibody (mouse-anti-FLAG M2, or mouse-anti-HA, each at 20 µg/ml in PBS). Uncoated surfaces of the wells were blocked by addition of 250 µl per well of blocking buffer (PBS+3% BSA) for 30 minutes. The conditioned media were used in serial dilutions, starting at 1X. As a secondary antibody we used 50 µl of anti-TGF-β1-antibody-conjugate (R&D SYSTEMS, Quantikine ELISA kit). Equal amounts of stabilized hydrogen peroxide and stabilized chromogen (tetramethylbenzidine) (both R&D SYSTEMS) were added. After 20 minutes of incubation stop solution (R&D SYSTEMS) was added. The optical density of each well was determined using a microplate reader, set to 450 nm.

Antibodies and western blots. All western blots were performed using Novex Tris-Glycine gels and the Novex blotting system. Protein was transferred onto nitrocellulose membranes, blocked with blocking buffer (TBST+4% BSA) and incubated with the indicated antibodies in blocking buffer overnight at 4° C. Secondary antibodies were conjugated to HRP and purchased from Jackson Immunolabs. After 5 washes with deionized water, blots were incubated for 1 hour with secondary antibody diluted 1:10,000 in blocking buffer. Blots were then washed four times for 5 minutes each in deionized water, followed by a 15 minutes wash in TBS+0.1% Tween 20 and a final series of four washes in deionized water (5 minutes per wash). Membranes were blotted to remove excess water and incubated with substrate solution (SuperSignal West Pico, Pierce) according to the manufacturer's instructions. After blotting the membranes to remove excess solution, the blots were exposed to x-ray film (Bio-Max MR, Kodak). TGF-β1 protein levels were measured using a rabbit polyclonal antibody (Cat# G1221) purchased from Promega. The anti-FLAG monoclonal antibody (M2) was purchased from Upstate Biotechnology. The anti-smad2 antibody was purchased from Zymed (Cat # 51-1300); and the anti-phospho-smad2 antibody was purchased from Upstate Biotechnology (Cat # 06-829).

Smad2 phosphorylation studies. Mv1Lu cells were plated onto 6-well plates, in DMEM medium containing 0.2% FBS. Twenty-four hours later, conditioned media from Cos1 cells transfected with various TGF-β1 plasmids were diluted twenty-fold and added to these cells (after first washing extensively with PBS). The cells were then incubated with the conditioned media for 30 minutes. Cells were washed with PBS and harvested. Cell pellets were dissolved in NP-40 lysis buffer containing 50 mM Tris-Cl pH 7.4, 150 mM NaCl, 50 mm NaF, 0.5% NP-40, 1 mM DTT, 1 mM sodium orthovanadate plus proteinase inhibitors (proteinase inhibitor cocktail tablets, 1 tablet per 10 mL buffer-Boehringer-Mannheim, Cat # 1836153). Thirty micrograms of total protein were applied to each lane of a 10% Novex Tris-Glycine gel.

Growth inhibition assays. Mv1Lu mink lung epithelial cells ($5 \times 10^5$ cells per well) were plated onto 96-well plates in DMEM containing 0.2% FBS. Various dilutions of recombinant human TGF-β1 standard or transfected Cos cell supernatants were added to the wells. After 24 hours, cells were pulsed with 1 µCi of [$^3$H]thymidine for 4 hours. Cells were trypsinized and harvested using a Packard Bioscience cell harvester and [$^3$H]-thymidine counts measured by liquid scintillation spectrometry.

Flow cytometry. Mv1Lu cells were harvested using CellStripper™, a non-enzymatic dissociation solution. Cells were counted and $3 \times 10^6$ cells were transferred to 5 mL FACS tubes. Cells were washed with PBS and fixed with 4% buffered paraformaldehyde on ice, for 5 minutes. The paraformaldehyde (8%) was added dropwise to cells in an equal volume of PBS with gentle vortexing to avoid clumping of cells. Cell pellets were then washed with 4 mL of cold PBS. Cells were permeabilized by the addition of 1 mL of −20° C. methanol with vortexing and incubated on ice for 2 minutes. Cells were washed with PBS and then treated for 5 minutes at room temperature with 50 mM glycine in PBS (to quench auto-fluorescence). After washing with PBS, cells were pelleted and 200 µl of blocking buffer plus 20 µl of conditioned medium containing N+5FLAG- or N+5HA-TGF-β1 ligand were added. Cells were incubated with ligand for 2.5 hours at 4° C. Following incubation with ligand, cells were washed two times with ice-cold PBS and once with blocking buffer. Cells were then incubated with blocking buffer for 30 minutes at room temperature prior to addition of 200 µl of blocking buffer containing primary antibody (anti-FLAG, anti-HA monoclonal or anti-KLH isotype control) diluted 1:1000 (approximately 0.4 µg in 200 µL). Incubation with primary antibody was carried out at 4° C. overnight. The following day, samples were washed twice with ice-cold PBS and once with blocking buffer. Samples were then incubated for one hour with TRITC-conjugated goat anti-mouse (Jackson Immunolabs) at 1:100 in blocking buffer. After washing twice with PBS and once with. FACS buffer (PBS+1.0% heat-inactivated FBS), samples were resuspended in 400 µl of FACS buffer and analyzed by flow cytometry using a FACSCalibur (Beckton Dickinson).

Confocal immunofluorescence microscopy. To confirm intracellular detection Cos1 cells were split on coverslips and transfected with either WT TGF-β1, FLAG- or HA-tagged TGF-β1 or WT-TGF-β1 and one of the tagged TGF-β1 plasmids. The next day the cells were fixed with 3.5% paraformaldehyde in PBS and permeabilized with methanol (−20° C.). Glycine (50 mM in PBS) was used to quench auto-fluorescence (5 minutes at room temperature). Non-specific binding sites were blocked with 10% normal goat serum in PBS and the cells were then incubated overnight with the primary antibody; mouse-anti-FLAG, mouse-anti-HA or rabbit-anti-TGF-β1. As secondary antibodies, FITC-conjugated goat-anti-rabbit and TRITC-conjugated goat-anti-mouse were used. Coverslips were mounted on slides, using mounting medium with DAPI (Vector Labs) and analyzed using confocal immunofluorescence microscopy.

Results

Design of FLAG-tagged TGF-β.

Initially, we chose to insert the FLAG tag immediately following the proteolytic cleavage site, which would make the tag N-terminal in the mature, processed molecule (FIG. 6A).

FLAG-tagged TGF-β1 is Processed and Secreted

Immunoblot analyses revealed that cells transfected with un-tagged TGF-β1 (WT) secreted large amounts of the ligand into the medium (FIG. 6B). Less ligand was secreted in the case of the NFLAG, although the levels, as determined by TGF-β sandwich ELISA (5 ng/ml) were well in excess of the minimum concentration of ligand (78 pg/mL) needed to maximally inhibit cell growth in these experiments according to a standard curve using recombinant human TGF-β1. Indeed, this N-terminally tagged TGF-β1 ligand is biologically active as it induces significant phosphorylation of smad 2, a TGF-β signaling intermediate (FIG. 6B). Levels of total smad 2 were equivalent in all treatments.

There was less accumulation of the lower molecular weight, mature cleaved TGF-β1 in the case of the FLAG-tagged molecule, relative to the un-tagged ligand. The cleavage site that separates LAP from the mature TGF-β peptide is preceded by a region of positively charged amino acids. Without meaning to be limited to one possible explanation, it is hypothesized that insertion of the FLAG epitope sequence, which carries a strong net negative charge, interferes with efficient cleavage of the pro-protein.

The reduced cleavage efficiency in the NFLAG protein was further analyzed by placing the FLAG tag further downstream of the cleavage site. Additional constructs were generated in which the FLAG or HA tag was inserted after the first five amino acids downstream of the cleavage site (N+5FLAG and N+5HA constructs). In addition, immediately following the tags, the first five amino acids of the mature peptide were re-iterated, followed by the remaining sequence of the mature peptide (FIG. 6C). These re-designed molecules appear to exhibit cleavage efficiencies comparable to that of the un-tagged molecule (FIG. 6D). In addition, the levels of secreted TGF-β1 appear equivalent for tagged and un-tagged molecules. FLAG- and HA-tagged TGFβ1 retain biological activity Comparison of the supernatants from Cos1 cells transfected with WT (un-tagged), N+5FLAG- and N+5HA-TGF-β1 revealed that the FLAG- and HA-tagged ligands were as efficient as the wild type molecule in inhibiting cell growth (FIG. 7A). Inhibition of growth was reversed by inclusion of a TGF-β neutralizing antibody, indicating a specific effect due to active TGF-β. No inhibition of growth was seen for media from Cos1 cells transfected with empty vector, suggesting that any endogenous TGF-β from Cos1 cells must be below the limits of detection in our assays.

TGF-β1 treatment leads to rapid and transient phosphorylation of smad 2 and smad 3. As a biochemical assay to measure TGF-β1 activity, we looked at levels of smad 2 phosphorylation (FIG. 7B). Mv1Lu cells incubated with conditioned medium from Cos1 cells transfected with vector alone showed no elevation in phosphorylated smad 2. However, cells incubated with media containing WT-TGF-β1, N+5FLAG-β1 and N+5HA-TGF-β1 showed significant elevations in the amount of phosphorylated smad 2. The accumulation of phospho-smad 2 was abrogated by the presence of TGF-β neutralizing antibody, indicating that phosphorylation was indeed specific to TGF-β treatment. Comparison of total smad 2 protein levels showed no significant differences between the samples. Thus, using two independent assays, one biological and the second biochemical, we have shown that insertion of the FLAG and HA epitope tags does not lead to loss of activity. Specific detection of FLAG- and HA-tagged TGF-β1 by sandwich ELISA (SELISA).

A particularly important application of the herein provided, newly designed TGF-β ligands is their use as therapeutics, with the ability to track the distribution of the administered cytokine with tag-specific reagents. To exploit this new use, a sandwich ELISA assay was developed to specifically detect epitope-tagged TGF-β1. Epitope-tagged ligand was captured by antibody immobilized onto the wells of a 96 well plate. Detection was facilitated by the use of the TGF-β1 conjugate, a polyclonal antibody against TGF-β1 conjugated to horse radish peroxidase (HRP) supplied in the human TGF-β1 Quantikine ELISA kit (R&D Systems). This assay was able to specifically detect FLAG- or HA-tagged TGF-β1 ligand in conditioned medium from transfected Cos-1 cells (FIG. 7C).

Detection of the FLAG-tagged molecule was possible at a dilution of 1:50, whereas specific detection of the HA-tagged ligand was achievable up to a 1:10 dilution. The inability to detect the HA-tagged ligand at lower concentrations may have been a result of lower levels of ligand in conditioned medium from this particular batch of conditioned medium. This again could be explained by variable transfection efficiencies between experiments. Alternatively, it is possible that the anti-HA monoclonal used here has a lower binding efficiency to plastic. FLAG-tagged TGF-β1 can be detected by immunofluorescence confocal microscopy The utility of the tagged ligands was next tested in an immunocytochemical application. Cos-1 cells grown on glass coverslips were transfected with WT TGF-β1 only, the WT- and N+5FLAG-tagged TGF-β1 or both the WT- and HA-tagged TGF-β1. A FITC-conjugated goat anti-rabbit antibody was used to bind and detect TGF-β1 and a TRITC-conjugated goat anti-mouse antibody was used to bind and detect either the FLAG or the HA-epitope. Antibodies directed against either of the epitope tags do not detect the untagged TGF-β1 molecule; whereas, the anti-TGF-β1 antibody is able to clearly detect both the untagged as well as the tagged molecules. Antibodies directed against either FLAG or HA were able to detect the appropriate tagged TGF-β1. Both untagged and epitope-tagged molecules show a high degree of co-localization.

Use of FLAG- and HA-Tagged TGF-β1 to Detect Cell Surface and Cytoplasmic Expression of TβRII by Flow Cytometry In addition to their potential as therapeutic reagents, the herein provided tagged ligands can serve as valuable diagnostic reagents for probing the pattern and level of TGF-β receptor expression in vivo. To demonstrate this, the FLAG- and HA-tagged TGF-β1 fusion proteins were used to detecting cell surface and cytoplasmic expression of TΔRII by flow cytometry.

Mv1lu cells were harvested using a non-enzymatic cell dissociation solution to avoid proteolysis of surface receptor complexes. Cells were fixed and permeabilized to examine total levels of TGF-β receptors (surface+intracellular), or fixed only (without permeabilization) to permit specific detection of surface receptor only. Cells were incubated with blocking buffer (10% goat serum in PBS) followed by incubation with blocking buffer containing a 1:100 dilution of conditioned medium containing epitope-tagged ligand. After washing, the primary antibody directed against the epitope tag was added and detection was facilitated using a TRITC-conjugated goat anti-mouse IgG. Labeling with FLAG-TGF-β1 results in a shifted peak relative to isotype control (mouse anti-KLH) indicating the presence TGF-β receptor complexes (surface+intracellular) and a smaller shift in the case of no non-permeabilized cells (cell surface receptor). Similar results were observed for the HA-TGF-β1 ligand. A greater shift in fluorescence intensity was consistently observed for fixed and permeabilized cells, a result consistent with previous studies showing that the majority of TGF-β receptor molecules are localized intracellularly and not on the cell surface (Zwaagstra et al., *Exp. Cell Res.*, 121–134, 2000).

Examples 3 and 4 demonstrates that several TGF-β fusions successfully used in a number of different assays, including:

(1) detection of expression of tagged ligand in transfected cells;

(2) detection of expression of TGF-β receptor complexes by flow cytometry; and (3) measurement of levels of tagged ligand in tissue culture supernatants.

It is believed that the flow cytometry assay described here represents a safer, faster, and cheaper alternative to the use of [$^{125}$I] radiolabeled TGF-β1 ligand, and expands the repertoire of techniques that can be used to look at TGF-β receptor expression levels. These tagged ligands will circumvent the complications due to cross reactivity of certain isoform-specific TGF-β antibodies. Finally, reagents will prove important in developing new transgenic models in which epitope-tagged TGF-β isoforms can be expressed in a spatially and/or temporally restricted manner.

Example 5

Further TGF-β Fusions

Additional functionalized TGF-β fusion proteins have been constructed in a manner essentially similar to the methods described in Examples 3 and 4. Specific examples of additional functionalized fusions include:

murine N+5FLAG TGF-β2 (MN5FLAGb2; SEQ ID NO: 24 and 25);

murine N+5HA TGF-β2 (MN5HAb2; SEQ ID NO: 26 and 27);

murine N+5FLAG TGF-β3 (MN5FLAGb3; SEQ ID NO: 28 and 29);

murine N+5HA TGF-β3 (MN5HAb3; SEQ ID NO: 30 and 31);

porcine active N+5FLAG TGF-β1 (actN5FLAGb1; SEQ ID NO: 32 and 33);

porcine latent N+5FLAG TGF-β1 (latN5FLAGb1; SEQ ID NO: 34 and 35) (made latent by mutations at positions 682 and 688 of SEQ ID NO: 34);

porcine active N+5HA TGF-51 (actN5HAb1; SEQ ID NO: 36 and 37); and porcine latent N+5HA TGF-β1 (latN5HAb1; SEQ ID NO: 38 and 39) (made latent by mutations at positions 678 and 684 of SEQ ID NO: 38).

Additional characteristics of each of these fusions, as well as N+5FLAG-TGF-β1 (SEQ ID NOs: 16 and 17) and N+5HA-TGF-β1 (SEQ ID NO: 20 and 21) fusions, are provided in Table 2.

TABLE 2

| Fusion name and SEQ ID NOs. | 5'UTR | CDS | 3'UTR | AA 1–5 of mature TGF-β | Epitope tag | Mature fusion |
|---|---|---|---|---|---|---|
| N+5FLAG-TGF-β1 (NOs: 16 & 17) | 1–347² | 348–1559 (1–404) | 1560–1612 | 1182–1196 (279–283) | 1197–1220 (284–291) | 1182–1559 (279–404) |
| N+5HA-TGF-β1 (NOs: 20 & 21) | 1–347 | 347–1571 (1–408) | 1572–1624 | 1182–1196 (279–283) | 1197–1232 (284–295) | 1182–1571 (279–408) |
| N+5FLAG-TGF-β2 (NOs: 24 & 25) | N/A | 1–1284 (1–428) | N/A | 907–921 (303–307) | 922–945 (308–315) | 907–1284 (303–428) |
| N+5HA-TGF-β2 (NOs: 26 & 27) | 1–7 | 8–1303 (1–432) | N/A | 914–928 (303–307) | 929–964 (308–319) | 914–1303 (303–432) |
| N+5FLAG-TGF-β3 (NOs: 28 & 29) | N/A | 1–1272 (1–424) | N/A | 895–909 (299–303) | 910–933 (304–311) | 895–1272 (299–424) |
| N+5HA-TGF-β3 (NOs: 30 & 31) | N/A | 1–1284 (1–428) | N/A | 895–909 (299–303) | 910–945 (304–315) | 895–1284 (299–428) |
| N+5FLAG-TGF-β1 (NOs: 32 & 33) | 1–10 | 11–1222 (1–404) | 1223–1349 | 845–859 (279–283) | 860–883 (284–291) | 845–1222 (279–404) |
| N+5FLAG-TGF-β1 (NOs: 34 & 35) | 1–14 | 15–1226 (1–404) | 1227–1253 | 849–863 (279–283) | 864–887 (284–291) | 849–1226 (279–404) |
| N+5HA-TGF-β1 (NOs: 36 & 37) | 1–10 | 11–1234 (1–408) | 1235–1361 | 845–859 (279–283) | 860–895 (284–295) | 845–1234 (279–408) |
| N+5HA-TGF-β1 (NOs: 38 & 39) | 1–10 | 11–1234 (1–408) | 1335–1361 | 845–859 (279–283) | 860–895 (284–295) | 845–1234 (279–408) |

[1]Refers to the nucleic acid sequence and amino acid sequence for the listed fusion.
[2]Residue positions correspond to the position in the nucleic acid sequence.
[3]residues within parentheses correspond to the positions in the amino acid sequence.

This disclosure provides methods for producing functionalized small molecules, including peptide-tagged TGF-β family proteins and other cytokines. The disclosure further provides such functionalized molecules, and methods of using these molecules in the clinical setting, as diagnostic and prognostic tools, therapy monitors, and so forth. It will be apparent that the precise details of the methods described may be varied or modified without departing from the spirit of the described invention. We claim all such modifications and variations that fall within the scope and spirit of the claims below.

What is claimed is:

1. A TGF-β family fusion protein, comprising:
   a N-terminal region consisting of an amino acid sequence of a pro-region (latency associated peptide) of a TGF-β1,
   a functionalizing peptide tag of no more than about 100 amino acids; and
   an amino acid sequence consisting of the mature portion of the TGF-β1;
   wherein the functionalizing peptide tag is inserted between a pair of adjacent residues between about residues 1 and 22 of the mature portion of the TGF-β1;
   and wherein the portion of the fusion protein comprising the mature portion of the TGF-β1 and the functionalized peptide tag has TGF-β1 activity that is reduced by no more than 50% as compared to the mature TGF-β1 alone.

2. A functional TGF-β1 fusion protein, comprising:

a functionalizing peptide tag of no more than about 100 amino acids for detecting, quantifying, or providing a specific additional function to the fusion protein; and a mature TGF-β1 comprising residues 279–283 and 296–408 of SEQ ID NO: 37, or an amino acid sequence that has at least 95% sequence identity with residues 279–283 and 296–408 of SEQ ID NO: 37 and which retains TGF-β1 activity;

wherein the functionalizing peptide tag is inserted between a pair of adjacent residues between about positions 1 and 22 of the mature TGF-β1;

and wherein the activity of the TGF-β1 fusion protein is reduced by no more than 50% as compared to the mature TGF-β1.

3. A functional TGF-β1 dimer formed by the association of two of the fusion proteins of claim 2.

4. The dimer of claim 3, wherein the dimer is a homodimer.

5. The dimer of claim 3, made by a process comprising:

expressing a nucleic acid molecule in a eukaryotic cell to produce a monomer fusion protein, wherein the nucleic acid molecule comprises:

a sequence encoding the functionalizing peptide tag;

a sequence encoding the mature TGF-β1; and a sequence encoding a pro-region (latency associated peptide) of the TGF-β1, located to provide targeting and/or assembly and/or processing of the fusion protein encoded for by the nucleic acid.

6. The dimer of claim 5, wherein the process further comprises:

associating two monomer fusion proteins to form the dimer.

7. The dimer of claim 5, wherein the sequence encoding the pro-region is located upstream to both the sequence encoding the functionalizing peptide tag and the sequence encoding the mature TGF-β1.

8. The dimer of claim 5, wherein the process further comprises:

cleaving the pro-region (latency associated peptide) from at least one fusion monomer.

9. The dimer of claim 5, wherein the process further comprises:

cleaving the pro-region (latency associated peptide) from both fusion monomers.

10. The fusion protein of claim 2, wherein the functionalizing peptide tag is inserted downstream of residue five of the M-nature TGF-β1.

11. The fusion protein of claim 2, where the protein comprises the amino acid sequence as in the mature portion for SEQ ID NO: 37.

12. The fusion protein of claim 2, further comprising a pro-region (latency associated peptide) of the TGF-β1 located to provide targeting and/or assembly and/or processing of the fusion protein.

13. The fusion protein of claim 12, wherein the pro-region is located at the N-terminal region of the fusion protein.

14. An isolated nucleic acid molecule encoding the fusion protein of claim 12, comprising SEQ ID NO: 8, 12, 32 or 38.

15. The fusion protein of claim 2, wherein the tag is an epitope tag, a purification tag, or an identification tag.

16. The fusion protein of claim 2, wherein the lag comprises a FLAG tag, a c-myc tag, a 6x His tag, a HA tag, a Ta1 tag, a T7 tag, a GFP peptide, or a GST peptide.

17. An isolated nucleic acid molecule encoding the fusion protein of claim 2, comprising residues 845–1234 of SEQ ID NO: 36.

18. The isolated nucleic acid molecule of claim 17, further comprising a sequence encoding a TGF-β pro-region.

19. The isolated nucleic acid molecule of claim 18, comprising SEQ ID NO: 36.

20. A recombinant nucleic acid molecule comprising a promoter sequence operably linked to the isolated nucleic acid molecule according to claim 17.

21. An isolated transgenic cell comprising a recombinant nucleic acid molecule according to claim 20.

22. The transgenic cell of claim 21, wherein the cell is a bacterial cell or an eukaryotic cell.

23. The eukariotic cell of claim 22, wherein the cell is a yeast cell or a mammalian cell.

24. An isolated nucleic acid molecule encoding the fusion protein of claim 2, comprising residues 835–1197 of SEQ ID NO: 8, SEQ ID NO: 10, residues 835–1197 of SEQ ID NO: 12, SEQ ID NO: 14, residues 845–1222 of SEQ ID NO: 32, residues 849–1226 of SEQ ID NO: 34, or residues 845–1234 of SEQ ID NO: 38.

* * * * *

UNITED STATES PATENT AND TRADEMARK OFFICE
CERTIFICATE OF CORRECTION

PATENT NO. : 6,756,215 B1                               Page 1 of 5
DATED      : June 29, 2004
INVENTOR(S) : Wolfraim et al.

It is certified that error appears in the above-identified patent and that said Letters Patent is hereby corrected as shown below:

Title page,
Item [56], References Cited, OTHER PUBLICATIONS,
"Brunner et al." reference, "Growt" should read -- Growth --.
"Oda, et al. al." should read -- Oda, et al. --; and "Glycosylphosphatidylinosito-l-Anchored" should read -- Glycosylphosphatidylinositol-Anchored --.

Column 1,
Line 34, "el al." should read -- et al. --.

Column 3,
Line 8, "p11/12FLABb1" should read -- p11/12FLAGb1 --.
Line 27, "11/12 FLAG" should read -- 11/12
                                      FLAG --.
Line 53, " "anti-P-smad2." should read -- "anti-P-smad2." --.
Line 66, "residues" should read -- (residues --.

Column 4,
Line 5, "proved" should read -- probed --.
Line 12, "cos-1" should read -- Cos1 --.
Line 27, "smad 2" should read -- smad2 --.
Line 63, "N FLAG-ß1" should read -- NFLAG-ß1 --.

Column 6,
Line 66, "("removal)" should read -- ("removal") --.

Column 9,
Line 31, "various known." should read -- various known assays. --.
Line 43, "use" should read -- used --.

Column 10,
Line 4, "Vecero" should read -- Vocero --.

Column 13,
Line 39, "99%." should read -- 99% --.

Column 14,
Line 61, "proteinsinclude" should read -- proteins include --.

Column 15,
Line 3, "BMP4" should read -- BMP-4 --.

UNITED STATES PATENT AND TRADEMARK OFFICE
CERTIFICATE OF CORRECTION

PATENT NO. : 6,756,215 B1
DATED : June 29, 2004
INVENTOR(S) : Wolfraim et al.

It is certified that error appears in the above-identified patent and that said Letters Patent is hereby corrected as shown below:

Column 17,
Line 18, "fusions proteins" should read -- fusion proteins --.
Line 22, "BMP3" should read -- BMP-3 --.
Line 27, "BMP4" should read -- BMP-4 --.

Column 18,
Line 57, "show" should read -- shown --.
Line 60, "molecule" should read -- molecules --.

Column 19,
Line 13, "BMP3" should read -- BMP-3 --.
Line 17, "BMP4" should read -- BMP-4 --.

Column 20,
Line 47, "BMP-ß16" should read -- BMP-16 --.
Line 48, "BMP3" should read -- BMP-3 --.
Line 50, "BMP-ß10 should read -- BMP-10 --.

Column 22,
Line 3, "are" should read -- art --.

Column 23,
Line 25, "a" should read -- as --.
Line 18, "method" should read -- methods --.

Column 24,
Line 28, "manufactures" should read -- manufacturers --.

Column 26,
Line 30, "prolie" should read -- proline --.
Line 37, "proteinencoding" should read -- protein-encoding --.

Column 27,
Line 50, "malcic" should read -- maleic --.

Column 28,
Line 20, "pharmacology Munson" should read -- Pharmacology, Munson --.
Line 59, "an" should read -- a --.

UNITED STATES PATENT AND TRADEMARK OFFICE
CERTIFICATE OF CORRECTION

PATENT NO. : 6,756,215 B1
DATED : June 29, 2004
INVENTOR(S) : Wolfraim et al.

It is certified that error appears in the above-identified patent and that said Letters Patent is hereby corrected as shown below:

Column 29,
Line 8, "controls" should read -- control --.
Line 35, "1996;" should read -- 1996). --.
Line 48, "el al." should read -- et al. --.
Line 62, "1999," should read -- 1999), --.

Column 32,
Line 17, "et al. (In" should read -- et al., In --.
Line 17, "Cloning." should read -- Cloning: --.
Line 42, "TGFß" should read -- TGF-ß --.

Column 33,
Line 41, "159,2000" should read -- 159, 2000 --.
Line 45, ",.p275" should read -- , pp. 275 --.

Column 34,
Line 43, "FLAG-ß1" should read -- TGF-ß1 --.
Line 48, "ataagaattgcggccgctaatcgatcccaagtgggcttgg" should read
-- ataagaattgcggccgctttaatcgatcccaagtgggcttgg --.

Column 35,
Line 24, "cos 1" should read -- Cos1 --.
Line 24, "serun" should read -- serum --.
Line 33, "a Sandwich" should read -- Sandwich --.
Lines 51 and 54, "Cat" should read -- Cat. --.
Line 65, "TGF-ß1is" should read -- TGF-ß1 is --.
Line 65, "Secreted" should read -- Secreted. --.

Column 36,
Line 3, "or" should read -- of --.
Line 37, "smad 2" should read -- smad2 --.
Line 47, "mm" should read -- mM --.
Line 47, "Dr" should read -- DTT --.
Line 50, "Cat" should read -- Cat. --.
Line 62, "Activity" should read -- Activity. --.
Line 64, "and" should read -- a --.

Column 38,
Line 9, "TGFP" should read -- TGF-ß --.
Line 42, "⊕" should read -- ß --.

UNITED STATES PATENT AND TRADEMARK OFFICE
CERTIFICATE OF CORRECTION

PATENT NO. : 6,756,215 B1
DATED : June 29, 2004
INVENTOR(S) : Wolfraim et al.

It is certified that error appears in the above-identified patent and that said Letters Patent is hereby corrected as shown below:

Column 41,
Line 38, "TGFß1" should read -- TGF-ß 1 --.
Lines 38-39, "FLAG- and HA-tagged TGF-ß1 retain biological activity" should be the heading for the immediately following paragraph.

Column 41, line 67 through Column 42, line 2,
"Specific detection of FLAG- and HA-tagged TGF-ß1 by sandwich ELISA (SELISA)" should be the heading for the immediately following paragraph.

Column 42,
Line 16, "Cos-1" should read -- Cos1 --.
Lines 27-29, "FLAG-tagged TGF-ß 1 can be detected by immunofluorescence confocal microscopy" should be the heading for the immediately following paragraph.
Line 32, "Cos-1" should read -- Cos1 --.
Line 56, "Mv1lu" should read -- Mv1Lu --.

Column 44,
Line 23, "51" should read -- ß1 --.
Table 2, "(NOs: 16 & 17)      (1-404)" should read
-- (NOs: 16 & 17)[1]      (1-404)[3] --.
Table 2, "[3]residues" should read -- [3]Residues --.

Column 122,
Line 37, "M-nature" should read -- mature --.
Line 40, "for" should read -- of --.
Line 51, "lag" should read -- tag --.
Line 52, "Tal" should read -- Tat --.

Column 123,
Line 1, "eukariotic" should read -- eukaryotic --.

UNITED STATES PATENT AND TRADEMARK OFFICE
CERTIFICATE OF CORRECTION

PATENT NO. : 6,756,215 B1
DATED : June 29, 2004
INVENTOR(S) : Wolfraim et al.

It is certified that error appears in the above-identified patent and that said Letters Patent is hereby corrected as shown below:

<u>Column 124</u>,
Line 4, add:
    25. The fusion protein of claim 2, where the protein comprises the amino acid sequence as in the mature portion of SEQ ID NO: 9, 11, 13, 15, 33 or 39.

Signed and Sealed this

Eighteenth Day of April, 2006

JON W. DUDAS
*Director of the United States Patent and Trademark Office*